US005447862A

United States Patent [19]

Heim et al.

[11] Patent Number: 5,447,862

[45] Date of Patent: Sep. 5, 1995

[54] PECTIN LYASE GENES OF *ASPERGILLUS NIGER*

[75] Inventors: Jutta Heim, Ramlinsburg; Bernd Meyhack, Magden; Christof Gysler, Blonay, all of Switzerland; Jacob Visser, Wageningen; Hermanus C. M. Kester, Druten, both of Netherlands

[73] Assignee: Ciba-Geigy Corporation, Ardsley, N.Y.

[21] Appl. No.: 723,002

[22] Filed: Jun. 28, 1991

Related U.S. Application Data

[63] Continuation-in-part of Ser. No. 150,880, Jan. 29, 1988, abandoned, and a continuation-in-part of Ser. No. 384,898, Jul. 24, 1989, abandoned.

[30] Foreign Application Priority Data

Feb. 4, 1987 [GB] United Kingdom ................. 8702475
Jul. 28, 1988 [GB] United Kingdom ................. 8818046
Jun. 26, 1989 [GB] United Kingdom ................. 8914666

[51] Int. Cl.[6] ......................... C12N 1/21; C12N 1/15; C12N 15/60; C12N 15/80

[52] U.S. Cl. ............................ 435/252.3; 435/252.33; 435/254.3; 435/320.1; 536/23.2; 536/23.74; 536/24.1

[58] Field of Search ............... 435/183, 232, 243, 254, 435/320.1, 913, 917, 252.3, 252.33, 254.3; 536/232, 23.2, 23.74, 24.1

[56] References Cited

U.S. PATENT DOCUMENTS 4,935,349 6/1990 McKnight et al. ................ 435/69.5

FOREIGN PATENT DOCUMENTS 0184438 6/1986 European Pat. Off. .
0191221 8/1986 European Pat. Off. .
0225078 6/1987 European Pat. Off. .
0238023 9/1987 European Pat. Off. .
0249350 12/1987 European Pat. Off. .
0278355 8/1988 European Pat. Off. .
WO87/04464 7/1986 WIPO .
WO86/06097 10/1986 WIPO .

OTHER PUBLICATIONS

F. E. A. von Houdenhoven, Ph D., Thesis, Agricultural University Wageningen, Netherlands In: Communicate Agricultural University Wageningen, 75-13 (1975).
J. Tilburn et al., Gene 26, 205, 221 (1983).
D. J. Ballance et al., Biochem. Biophys. Res. Commun. 112, 284-289 (1983).
D. J. Ballance et al., Gene 36, 321-331 (1983).
F. P. Burton et al., Gene 37, 207-214 (1985).
D. Cullen et al., Abstract No. 20 of the 203rd Meeting of Genetical Society London, K.K. 15/16. Nov. 1985.
J. A. Rambosek et al., Am. Soc. Microbiol. 86th Meeting, Washington D.C. 23-28 Mar., 1986, Abstr. No. H-10, p. 129.

(List continued on next page.)

*Primary Examiner*—Richard A. Schwartz
*Assistant Examiner*—James Ketter
*Attorney, Agent, or Firm*—James Scott Elmer

[57] ABSTRACT

Recombinant DNA molecules coding for pectin lyase (PL) expression systems and derivatives thereof, such as the structural genes of PLA, PLB, PLC, PLD, PLE and PLF, and corresponding regulatory sequences, e.g. promoter, signal and terminator sequences, and hybrid vectors comprising corresponding DNAs, including hybrid vectors with DNA coding for homologous or heterologous polypeptides, hosts, especially filamentous fungi, e.g. Aspergillus hosts, transformed by said vectors, methods for the preparation of said recombinant DNA molecules and said hosts and the use of the recombinant DNA molecules for the preparation of new expression systems. A further objective is the preparation of polypeptides by means of said DNAs and said hosts.

49 Claims, 22 Drawing Sheets

OTHER PUBLICATIONS

A. Kos et al., Gene 39, 231–238 (1985).

W. V. Hartingsveldt et al., Mol. Gen. Genet. 206, 71–75 (1987).

T. Goosen et al., Curr. Genet. 11, 499–503 (1987) published Mar. 1987.

Tsuyumu et al, Symbosis, vol. 2 pp. 103–110 (1986).

Linhardt et al, Applied Chemistry and Biotechnology vol. 12 pp. 135–176 (1986).

Ballance et al, Molec. Gen. Genet. vol. 202 pp. 271–275 (1986).

J. M. Mattern et al., Conference Abstract of the 14th International Congress of Microbiology (Microbe 86), 07–13 Sep. 1986, Manchester, U.K. Abstract from Derwent Abstract, Biotechnology Abstracts, No. 88–00666.

Patent Abstracts of Japan, vol. 12, No. 405(C–539) (3252).

Gwynne et al., Bio/Technology, 5:713–719 (1987).

Dean et al., *The Plant Cell,* 1:275–284 (1989).

Tamaki et al., *J. of Bacteriol.,* 170:3468–3478 (1988).

Kelly et al., Mol. Gen. Genet., 222:323–328 (1990).

Collmer et al., *J. Bacteriol.,* 161(3):913–920 (1985).

Suggs et al., PNAS USA, 78:6613–6617 (1981).

Liersch et al., *Chemical Abstracts,* 105:220 (1986).

Sakai et al., *Mol. Cell. Biol.,* 4:651–656 (1984).

pUN121 vector DNA

DNA insert

ATG signal sequence of PLI promoter sequence of PLI structural gene coding for PLI

Fig. 6
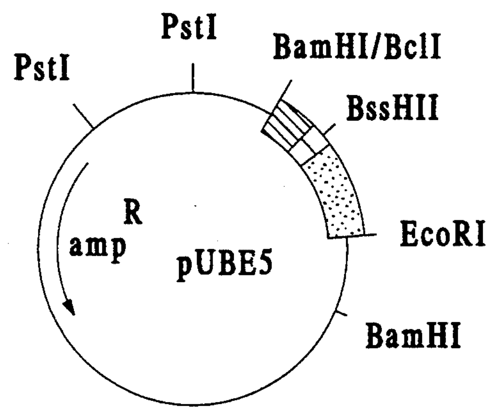
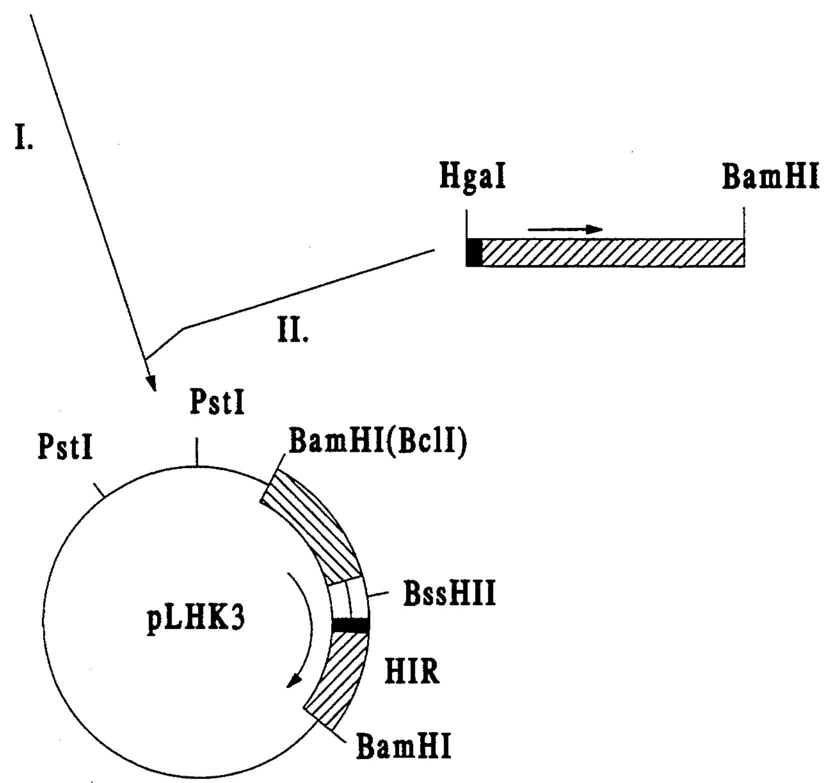
signal sequence of PLI
partial promoter sequence of PLI, without TATAA
BssHII-HgaI linker
structural gene coding for PLI
desulfatohirudin gene A. niger N400 DNA 55 1 1 3 4 5
pel A
EcoRI
SphI
XhoI
XbaI
KpnI
HindIII
PvuI, 1
XhpI, 113
SalI, 338
EcoRX, 161
PvuII, 387
BamHI 447
ClaI, 1502
PstI, 1416
ClaI, 1510
KpnI, 1506
KpnI, 1019
SalI, 1473
ClaI, 3170
HindIII
1000
1220
1240
1270
1290
1430
4180
1430
1510
1600
1630
3500
4180
4780
n1
n1
n3
B
B
D
n4
A
A
n5
n6
C
r1
n7
C
r1
n8
D
r3
n9
r4
n10
r5
F
n11
r6
n12
r7
n13
F
r8
r9
G
r10
r11
G
r12
r13
r14
H

Fig. 18A

```
PLD  MKYAAALTAIAAL-AARAAAVGVSGTPVGF
PLA  MKYSTIFSAAAAVFAGSAAAVGVSGSAEGF
PLB  MHYKLLFAAAAASLASAVSAAGVVGAAEGF
PLC  MKV--PFLQLLCLNAALASANVVQGAAQGF
                40        50        60

PLD  ASSATGGGDATPVYPTTTDELVSYLGDDEA
PLA  AEGVTGGGDATPVYPDTIDELVSYLGDDEA
PLB  AHGVTGGGSASPVYPTTTDELVSYLGDNEP
PLC  AAGVTGGGDITPSYPKTNEELVSLLESDEP
                70        80        90

PLD  RVIVLSKTFDFTDTEGTTTTGCAPWGTAS
PLA  RVIVLTKTFDFTDSEGTTTGTGCAPWGTAS
PLB  RVIILDRTFDFTGTEGTETTGCAPWGTAS
PLC  QVVVLTKTFDFIGTEGTTEDGCAPWGTGK
               100       110       120

PLD  GCQLAINKDDWCTNYEPDAPTTTVTYNTAG
PLA  ACQVAIDQDDWCENYEPDAPSVSVEYYNAG
PLB  QCQVAINLHSWCDNYQASAPKVSVTYDKAG
PLC  SCQLAINSNGWC----GKNPVVTITYDNAA
               130       140       150
```

Fig. 18B

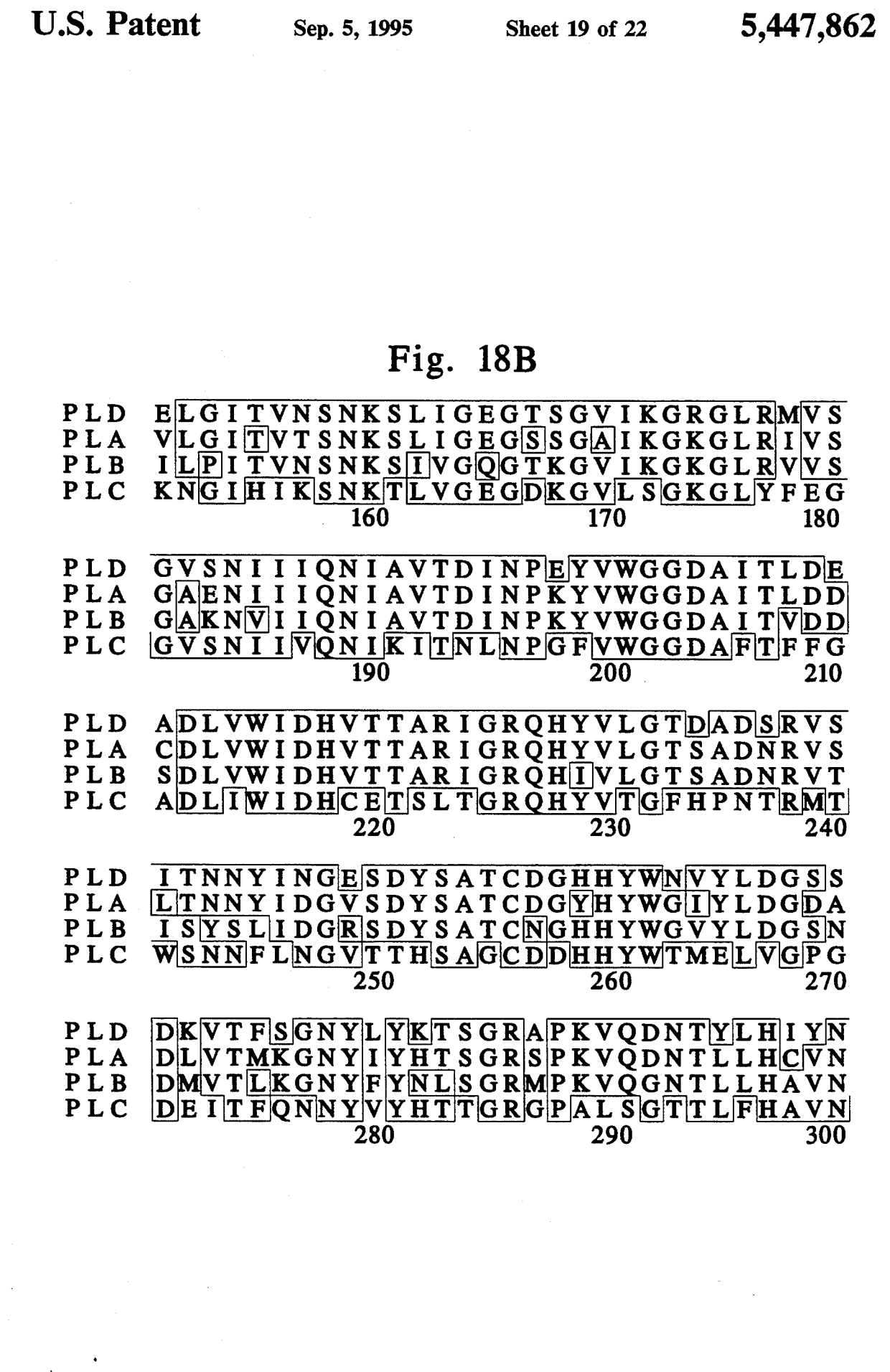

```
PLD  ELGITVNSNKSLIGEGTSGVIKGRGLRMVS
PLA  VLGITVTSNKSLIGEGSSGAIKGKGLRIVS
PLB  ILPITVNSNKSIVGQGTKGVIKGKGLRVVS
PLC  KNGIHIKSNKTLVGEGDKGVLSGKGLYFEG
               160       170       180

PLD  GVSNIIIQNIAVTDINPEYVWGGDAITLDE
PLA  GAENIIIQNIAVTDINPKYVWGGDAITLDD
PLB  GAKNVIIQNIAVTDINPKYVWGGDAITVDD
PLC  GVSNIIVQNIKITNLNPGFVWGGDAFTFFG
               190       200       210

PLD  ADLVWIDHVTTARIGRQHYVLGTDADSRVS
PLA  CDLVWIDHVTTARIGRQHYVLGTSADNRVS
PLB  SDLVWIDHVTTARIGRQHIVLGTSADNRVT
PLC  ADLIWIDHCETSLTGRQHYVTGFHPNTRMT
               220       230       240

PLD  ITNNYINGESDYSATCDGHHYWNVYLDGSS
PLA  LTNNYIDGVSDYSATCDGYHYWGIYLDGDA
PLB  ISYSLIDGRSDYSATCNGHHYWGVYLDGSN
PLC  WSNNFLNGVTTHSAGCDDHHYWTMELVGPG
               250       260       270

PLD  DKVTFSGNYLYKTSGRAPKVQDNTYLHIYN
PLA  DLVTMKGNYIYHTSGRSPKVQDNTLLHCVN
PLB  DMVTLKGNYFYNLSGRMPKVQGNTLLHAVN
PLC  DEITFQNNYVYHTTGRGPALSGTTLFHAVN
               280       290       300
```

Fig. 18C

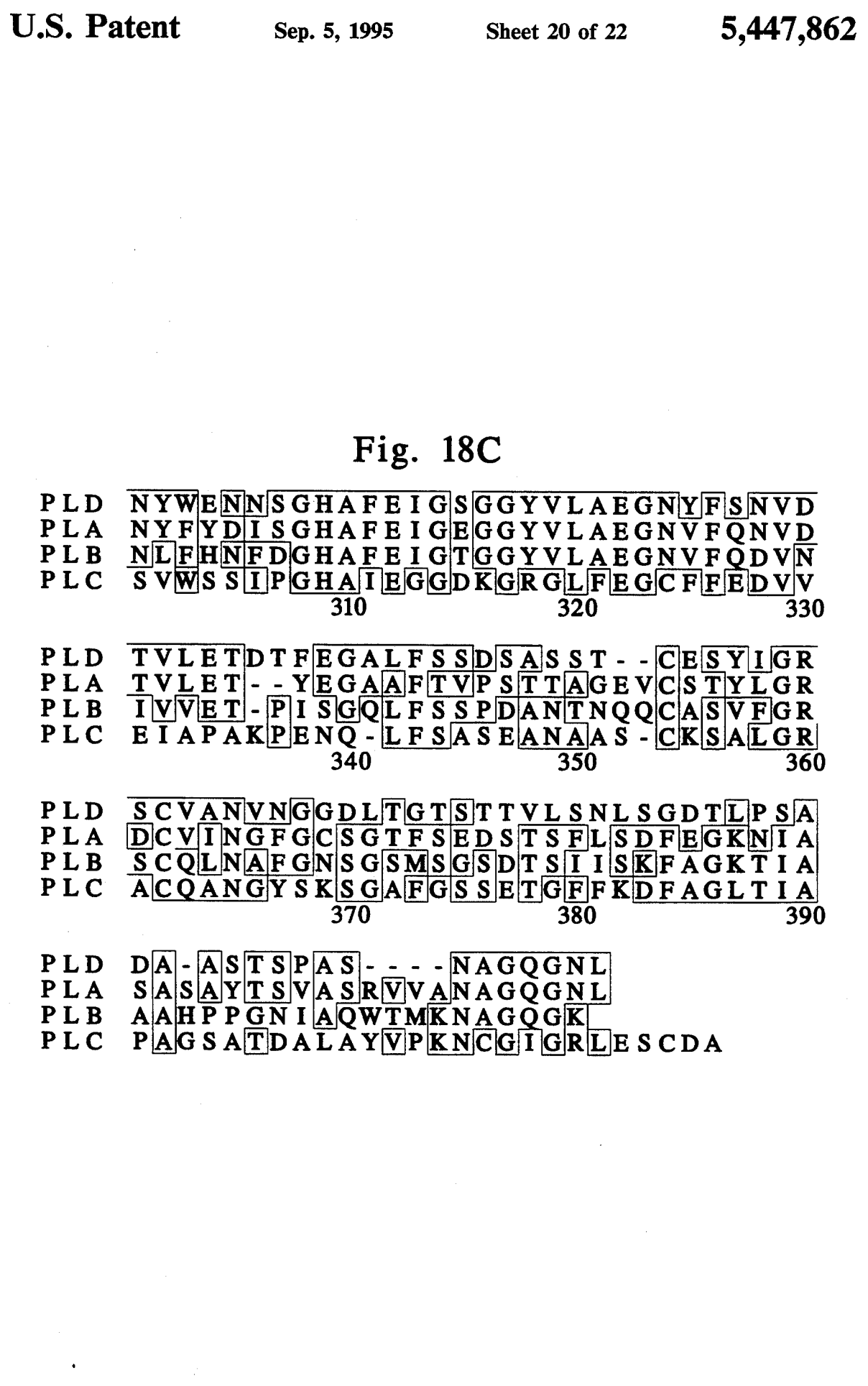

```
PLD  NYWENNSGHAFEIGSGGYVLAEGNYFSNVD
PLA  NYFYDISGHAFEIGEGGYVLAEGNVFQNVD
PLB  NLFHNFDGHAFEIGTGGYVLAEGNVFQDVN
PLC  SVWSSIPGHAIEGGDKGRGLFEGCFFEDVV
             310       320       330

PLD  TVLETDTFEGALFSSDSASST--CESYIGR
PLA  TVLET--YEGAAFTVPSTTAGEVCSTYLGR
PLB  IVVET-PISGQLFSSPDANTNQQCASVFGR
PLC  EIAPAKPENQ-LFSASEANAAS-CKSALGR
             340       350       360

PLD  SCVANVNGGDLTGTSTTVLSNLSGDTLPSA
PLA  DCVINGFGCSGTFSEDSTSFLSDFEGKNIA
PLB  SCQLNAFGNSGSMSGSDTSIISKFAGKTIA
PLC  ACQANGYSKSGAFGSSETGFFKDFAGLTIA
             370       380       390

PLD  DA-ASTSPAS----NAGQGNL
PLA  SASAYTSVASRVVANAGQGNL
PLB  AAHPPGNIAQWTMKNAGQGK
PLC  PAGSATDALAYVPKNCGIGRLESCDA
```

PECTIN LYASE GENES OF *ASPERGILLUS NIGER*

This application is a Continuation-in-part application of Ser. No. 150,880, filed Jan. 29, 1988, now abandoned, and Ser. No. 384,898, filed Jul. 24, 1989, now abandoned.

FIELD OF THE INVENTION

The invention relates to the field of genetic engineering and provides novel DNA molecules comprising DNA sequences coding for several pectin lyases of *Aspergillus niger* and/or the promoter, signal and terminator sequences thereof. The novel DNA molecules are useful for the overproduction of the pectin lyases in Aspergillus and/or the construction of hybrid vectors expressing foreign genes in filamentous and other fungi under the control of an *A. niger* pectin lyase promoter, signal sequence and/or terminator sequence. It is now possible to produce a single pectin lyase which is uncontaminated with other pectin lyases.

BACKGROUND OF THE INVENTION

Although in genetic engineering techniques numerous polypeptide expression systems for prokaryotic and eukaryotic hosts are already known, there is a continuous need for novel systems which may have advantages over the known systems.

Very widely used are the prokaryotic *Escherichia coli* host and the eukaryotic yeast host, e.g. *Saccharomyces cerevisiae*, for which a high number of different expression hybrid vectors, mostly plasmids, have been developed. The drawbacks of *E. coli* hosts are that they cannot glycosylate the formed polypeptide and that for lack of secretion the foreign peptide may accumulate within the host cell and prevent further growth. The yeast hosts do glycosylate, however, like *E. coli*, they do not secrete the polypeptides, except very small ones, into the nutrient medium. Yeasts secrete only into the periplasmic space. Higher eukaryotic hosts are mammalian cancer cells which are able to glycosylate and secrete into the nutrient medium, however, cultivation thereof is very slow and expensive and the danger exists that oncogenic nucleic acids are isolated together with the desired peptide of which the latter may not be freed.

In the need for other hosts also filamentous fungi, such as *Neurospora crassa, Aspergillus nidulans* and *Aspergillus niger*, have been investigated. Such fungi are already widely used for industrial purposes, however, the application thereof in genetic engineering techniques has lagged behind, mainly for lack of an appropriate transformation system. In contrast to *Saccharomyces cerevisiae*, filamentous fungi do not contain plasmids which could be used for the introduction of foreign genes and phenotype selection. It is, however, possible to transform filamentous fungi with foreign plasmids containing a selectable marker gene. All vectors described so far for filamentous fungi do not autonomously replicate, as those of yeasts do, but are integrated into the fungal chromosome. This event occurs only at a very low frequency. Advantageously, on the other hand, integrative transformation renders the transformants mitotically very stable, even under non-selective conditions. Stable integration of more than one hundred copies has been reported.

The first vector for filamentous fungi described contained the qa-2 gene of *Neurospora crassa* as selectable marker. This gene encodes the enzyme catabolic dehydroquinase and can be used for functional complementation of aro mutants of *N. crassa* [Case, M. E., Schweizer, M., Kushner, S. R. and Giles, N. H. (1979) Proc. Natl. Acad. Sci. USA 76, 5259-5263]. Aro mutants are unable to grow on minimal medium without an aromatic amino acid supplement. Transformation of *N. crassa* by the qa-2 vector occurred by integration of a single copy of the plasmid into the chromosome. 30% of stable Aro+ integrants retained the integrated qa-2 gene still linked to the bacterial plasmid sequences [Case, M. E. (1982) in Genetic Engineering of Microorganisms for Chemicals (Hollander, A., DeMoss, D., Kaplan, S., Konisky, J., Savage, D. and Wolfe, R. S., eds), pp. 87-100, Plenum]. This observation made co-transformation of non-selective DNA-sequences together with selective ones a feasible task.

In *Aspergillus nidulans*, which has a sexual cycle and is therefore amenable to classical genetic manipulations, both negative and positive selection systems have been identified. Either using heterologous DNA from *N. crassa* or homologous DNA, functional complementation of *A. nidulans* pyrG-mutants by transformation with plasmids containing the pyrG gene was obtained (Ballance et al. BBRC 112,284 1983; Tilburn et al. Gene 26, 205, 1983). In other systems mutations at the trpC or argB locus were functionally complemented by transformation with the appropriate plasmids [Yelton et al. PNAS 81, 1470, 1984; Yelton et Timberlake J. Cell. Biochem. Suppl. 9C 173, 1985; Johnstone et al. EMBO J. 4, 1307, 1983].

A dominant positive selection system has also been developed making use of the amdS gene isolated from *A. nidulans* which enables *A. niger* transformed therewith to grow on acetamide as sole nitrogen source (Tilburn et al., Gene 26, 205, 1983; Wernars et al., Curr. Genet. 9, 361, 1985; Kelly, J. M. et al., EMBO J. 4, 475,1985).

Compared to *N. crassa* or *A. nidulans, A. niger* is by far the more important organism. It is used widely in the industrial production of enzymes, e.g. for use in the food industry. *A. niger* differs from *A. nidulans* by its secretory capacity, in that it secretes a variety of hydrolytic enzymes, e.g. glucoamylase, $\alpha$-amylase, pectinase, cellulase, $\beta$-glucanase, $\beta$-galactosidase, naringinase, pentosanase, acid protease and lignase, the glucoamylase and pectinase complex being the most important ones.

*A. niger* has no known sexual cycle. Mutations can therefore not be introduced via meiotic recombinations. By classical mutation and selection procedures, extensive strain improvements in the secretion of hydrolytic enzymes have however been achieved.

Of the genes of *A. niger* enzymes only those of glucoamylase (Boel et al. EMBO J. 3, 1581, 1984) and alcohol and aldehyde dehydrogenase (WO 86/06097) together with their promoter and signal sequences have been characterised and used in transformation experiments with *A. nidulans* and *A. niger*, respectively.

As selection markers for *A. niger* have been used the heterologous amds gene (Kelly and Hynes, EMBO 3. 4, 475, 1985), and the argB gene (Buxton et al., Gene 37, 207, 1985; EP 184 438; WO 86/06097), both obtained from *A. nidulans*.

*A. niger* is the most important organism for the industrial production of pectin degrading enzymes. Pectins are polygalacturonides of high molecular weight (20000-40000 D) consisting of $\alpha$-1,4-glycosidic bounded D-galacturonic acid polymers and occur in nature as constituents of higher plant cells, where they are attached to cellulose molecules and where they are mainly found in the primary cell wall and the middle lamella. Amongst the richest sources of pectin are lemon and orange rind, which contain about 30% of this polysaccharide. Pectic enzymes are degrading the carbohydrate polymer substrate either by hydrolysis of the $\alpha$-1,4-glycosidic bond (polygalacturonase) or by transelemination of the $\alpha$-4,5 unsaturated galacturonic residue from the pectin molecule (different pectin lyases). The systematic name of pectin lyase is pectin transeliminase (EC 4.2.2.10).

In *A. niger* the proteins of the pectic complex are not expressed constitutively. Under inducing conditions using pectin or breakdown products thereof *A. niger* expresses the above mentioned enzymes, including PLI, when other carbon sources, such as glucose or sucrose, are limiting. In surface cultures the pectic enzymes tend to remain associated with the outer cell wall. Increasing pectin and $Ca^{2+}$ concentration in the medium leads to complete secretion.

Pectinases, such as PLI, are used by the food stuff industry mainly for fruit juice clarification.

From *A. niger* two different pectin lyases, PLI and PLII, have been purified and partially characterized by F. E. A. Van Houdenhoven (22). PLI contains four residues of mannose, whereas PLII has two residues of mannose and glucose each. The enzymes have different molecular weights (PLI: 37.5 kD, PLII: 36 kD). Before the present invention no total or partial amino acid sequences have been published.

The present invention is based on a partial structure determination of pectin lyase I (PLI) which allowed the synthesis of DNA probes coding for relevant parts of the protein. By means of the DNA probes it was possible to screen for and isolate DNA coding for PLI, eventually together with pre- and post-sequences thereof, from a gene library of *A. niger*.

By hybridization of parts of the PLI gene to a genomic library of *A. niger* further PL genes have been detected which are also subject of the present invention. The PLI structural gene with the N-terminus flanking region obtained from *A. niger* N756 is at its N-terminus identical to the PLD gene obtained from *A. niger* N400. Accordingly the latter is also part of the present invention. The present PLA seems to be part of the previously purified PL mixture named PLII.

Hereinafter, PLI is also named PLD and the PLI structural gene is named pelD.

OBJECTS OF THE INVENTION

Objects of the invention are recombinant DNA molecules comprising DNA sequences coding for novel pectin lyase expression systems and derivatives thereof, such as the structural genes of said pectin lyases and corresponding regulatory sequences, e.g. promoter, signal and terminator sequences, and hybrid vectors comprising corresponding DNAs, including hybrid vectors with DNA coding for homologous or heterologous polypeptides, hosts, especially filamentous fungi, e.g. Aspergillus hosts, transformed by said vectors, methods for the preparation of said recombinant DNA molecules and said hosts and the use of the recombinant DNA molecules for the preparation of new expression systems. A further objective is the preparation of polypeptides by means of said DNAs and said hosts.

The novel pectin lyase expression systems comprise DNA sequences coding for the promoters, the signal sequences, the structural genes and the terminators of said novel pectin lyase genes. The novel pectin lyases are named PLA, PLB, PLC, PLD or PLI, PLE and PLF.

More particularly, one object of the present invention is the construction of hybrid vectors comprising DNA sequences coding for the promoters of PLA, PLB, PLC, PLI or PLD, PLE and PLF, optionally for the signal sequence of these proteins, and optionally for the terminators thereof. These hybrid vectors are used for the incorporation of genes coding for particular proteins and for the transformation of filamentous fungi, such as Aspergillus, Penicillium and Cephalosporium. Cotransformation of *A. niger* with 2 different plasmids can be carried out, whereby one of the plasmids is selected from the group of the novel hybrid vectors of the invention, and the other one is a specially constructed selection plasmid which works in connection with a mutated strain of a filamentous fungus.

The present invention also concerns the overproduction of said novel pectin lyases in Aspergillus species, and the production of the single PLs which are uncontaminated with the other PLs, or of predetermined artificial mixtures thereof.

The present invention further concerns the production of any protein the structural gene of which can be expressed in the presence or under the control of the present recombinant PL DNAs.

The various subjects of the invention will become more evident from the following detailed description of the invention.

DETAILED DESCRIPTION OF THE INVENTION

The Recombinant DNA Molecules

More particularly, the present invention concerns a recombinant DNA molecule comprising a DNA sequence coding for the expression systems of the pectin lyases PLA, PLB, PLC, PLI or PLD, PLE or PLF, or a derivative thereof.

The term "expression system" means a DNA sequence capable of expressing a polypeptide and comprises the promoter, the signal sequence, the structural gene and the terminator.

The term "derivative" when used in connection with the novel DNA sequences is intended to include larger derivatives with flanking sequences, fragments of said DNA sequence, mutants, especially naturally occurring mutants, and DNA sequences which are degenerated in accordance with the genetic code.

Larger derivatives of the novel recombinant DNA molecules are those excisable from the *A. niger* genome and comprising the DNA sequences of the pectin lyase genes provided in the vectors shown in FIGS. 1 to 14, preferentially 1 and 9 to 14, which latter are deposited according to the Budapest Treaty. Such larger derivatives can be found in a genomic library of *A. niger* N756 or N400 obtained by fragmentation of the nucleic acids, treatment of the fragments with a suitable restriction enzyme, e.g. EcoRI, BamHI or HindIII, ligating into a suitable vector, e.g. the lambda phage or the plasmids pUN121 or pBR322, cloning, e.g. in *E. coli*, and excising again, with the same restriction enzyme. The *A. niger* derived inserts of plasmids pCG3B11, pGW820, pGW830, pGW840, pGW850, pGW860 and pGW880 shown in FIGS. 1 and 9 to 14 are examples of larger derivatives of the novel DNA molecules of the present invention.

Fragments of the novel DNA sequences are e.g. those extending between two restriction sites of these plasmids and retaining promoter, signal, structural or terminator functions.

Preferred fragments are those containing the promoter sequence, the signal sequence, the structural gene of a novel PL, or the terminator sequence, or any combination thereof.

The fragments of the DNA sequence may contain linkers which provide for successful linkage to other DNA molecules.

The PLI promoter sequence is contained in the DNA region between nucleotide positions 1 to 688, whereby the sequence between nucleotides about 542 and 589 is essential. For the promoter sequence the TATAA box at nucleotides.542 to 569 is important as the RNA-polymerase recognition site. Suitable linkers may be attached to these fragments. The PL promoter sequences of the genes encoding PLA, B, C, E is contained in the DNA region before the structural gene and comprises up to about 2000, preferably up to about 1000 to 1400 nucleotides. In pGW820 the promoter is located on the sequence between the SalI (1240) and the PstI (2420) restriction site. For the promoter sequence the TATAA boxes are important as the RNA-polymerase recognition sites. On pelA the TATAA box is located at position 1221 (SEQ ID NO. 3), on pelB at position 953 (SEQ ID NO. 5) and on pelC at position 1261 (SEQ ID NO 7).

The short promoters from around the TATAA boxes up to the start of the signal sequences are of particular interest for the non-induced expression of polypeptides. If pectin induced expression is required the sequences upstream of the TATAA boxes are necessary for regulating the strength of the promoter. Suitable linkers may be attached to these fragments.

The promoters of the PL genes of *A. niger* are inducible, i.e., the expression of the structural gene attached thereto, e.g. the structural gene coding for a PL or any foreign gene, is induced by addition of pectin or pectin degradation products to the medium. In the absence of pectin and presence of sufficient glucose the promoter is not operating. If the upstream regulatory sequences are absent the promoter becomes constitutive.

The DNA coding for the signal sequence extends between the end of the promoter and the beginning of the sequence coding for the mature protein. The signal sequence is a preferred sequence and DNA molecules comprising it, e.g. such containing said sequence and optional suitable linkers, are preferred DNA molecules.

The signal sequence of PLI extends between amino acids 1 to 19. In PLA and PLB the signal sequence contains about 20 amino acids, in pelC about 18 amino acids. The corresponding coding region extends in pelA from the ATG codon at position 1361 down to the PstI cleaving site at position 1420, in pelB from position 1134 to at least position 1190, and in pelC from position 1368 to position 1421.

As is evident from the corresponding sequence listings the structural genes of PLI, PLA, PLB and PLC contain several introns. Also the structural genes may contain suitable linkers.

The terminators start with the stop codons, e.g. TAA, and may extend up to one of the restriction sites within said sequences. The terminator fragment contains at least 300 bp and may contain suitable linkers.

Suitable linkers to above fragments have a DNA sequence which fits into the restriction site of the DNA to which the fragment is to be linked. They may contain a predetermined restriction site.

Fragments of the DNA sequence of the invention are also such which are composed of smaller fragments, e.g. those containing the promoter, the promoter and the signal or structural sequence, the signal and the structural sequence, or the structural gene without the introns, and the like.

Mutants of the DNA sequence of the invention are e.g. naturally occurring mutants. The invention comprises also natural or synthetic mutants of the signal sequence with a similar or identical hydrophobicity profile, e.g. wherein the codons for the polar amino acids lysine ($K^{\delta+}$), tyrosine ($Y^{\delta-}$) and arginine ($R^{\delta+}$) are exchanged by codons for other amino acids having similar charges, and the hydrophobic amino acids alanine (A), leucine (L) and threonine (T), are replaced by codons for other hydrophobic amino acids. For example, the codon for the positively charged lysine may be replaced by a codon for arginine and vice versa, the codon for the negatively charged tyrosine by a codon for glutamate or aspartate, and/or the codon for the non-polar, hydrophobic alanine by any one of the codons for threonine, proline, valine, isoleucine, leucine, methionine or phenylalanine, and the like. Other mutations are "silent mutations" wherein one or a few other nucleotides, e.g. up to about 30, are replaced by one or more other nucleotides, whereby the new codons code for the same amino acid(s).

DNA sequences of the invention which are degenerated are, like silent mutations, such which are degenerated within the meaning of the genetic code in that an unlimited number of nucleotides are replaced by other nucleotides without changing the amino acid sequence for which they code. Such degenerate DNA sequences may be useful because of their different restriction sites.

Recombinant DNA molecules comprising a DNA sequence of the invention or a derivative thereof are especially recombinant vectors, alternatively called hybrid vectors, containing such DNA sequences as inserts. They are usable for cloning in hosts, such as bacteria, fungi or animal cells. Such hybrid vectors are derived from any vector useful in the art of genetic engineering, such as from phages, cosmids, plasmids or chromosomal DNA, such as derivatives of page λ, e.g. NM 989, or of phage M13, e.g. M13mp8 phage DNA (ref. 15) linearized by BamHI digestion, bacterial plasmids, e.g. pBR 322, pUN121, pUC18, or yeast plasmids, e.g. yeast 2μ plasmid, or also chromosomal DNA, derived e.g. from Aspergillus, e.g. *A. niger*, for example those provided by EP 184 438, or defective phages or defective plasmids in the presence of a helper phage or a helper plasmid allowing replication of said defective phages or plasmids, e.g. M13(+)KS vector in presence of e.g. M13K07 helper phage.

A hybrid vector of the invention contains, in addition to the DNA sequences of the invention or a derivative thereof, a replication site and optionally, depending on the type of the DNA derivative, an expression control sequence, such as an enhancer sequence, upstream activation site, a promoter and signal sequence, and/or a structural gene different from the corresponding present *A. niger* derived sequences. Such enhancer sequence may be derived from the extrachromosomal ribosomal DNA of *Physarum polycephalum* (PCT/EP 8500278), or it may be the upstream activation site from the acid phosphatase PHO5 gene (EP-A-213 593), or the PHO5, trp, PHO5-GAPDH hybrid (EP-A-213 593), or the like promoter.

Structural genes ligated to the present promoter, signal and/or terminator sequences are, besides those coding for pectin lyases PLA, PLB, PLC, PLE and PLF with or without introns, also homologous other pectin lyase genes, e.g. the PLD (or PLI) gene, or other Aspergillus genes and heterologous structural genes which originate from viruses, procaryotic cells or eucaryotic cells and which may be derived from genomic DNA or from cDNA prepared via the mRNA route or may be synthesized chemically, coding for a wide variety of useful polypeptides, including glycosylated polypeptides, in particular of higher eukaryotic, especially mammalian, such as animal or especially human origin, such as enzymes which can be used, for example, for the production of nutrients and for performing enzymatic reactions in chemistry, or polypeptides, which are useful and valuable for the treatment of human and animal diseases or for the prevention thereof, for example hormones, polypeptides with immunomodulatory, anti-viral and anti-tumor properties, antibodies, vital antigens, vaccines, clotting factors, foodstuffs and the like.

Examples of such heterologous structural genes are e.g. those coding for hormones such as secretin, thymosin, relaxin, calcitonin, luteinizing hormone, parathyroid hormone, adrenocorticotropin, melanocyte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFB, growth hormones, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB consisting, in the order from N- to C-terminus, of the first and second domains ($B_1$, corresponding to amino acids 1 to 60, and B2, corresponding to amino acids 61 to 92) of human interferon aB, of the third domain ($D_3$, corresponding to amino acids 93 to 150) of human interferon aD and of the fourth domain ($B_4$, corresponding to amino acids 151 to 166) of human interferon aB, proteinase inhibitors such as $\alpha_1$-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, calcitonin, human calcitonin-related peptide, blood clotting factors, such as factor IX or VIIIc, erythropoietin, eglin, such as eglin C, hirudin, desulfatohirudin, such as desulfatohirudin variant HV1, HV2 or PA, human superoxide dismutase, viral thymidin kinase, β-lactamase, glucose isomerase. Preferred genes are those coding for a human α-interferon or hybrid interferon, human tissue plasminogen activator (t-PA), hepatitis B virus surface antigen (HBVsAg), insulin-like growth factor I and II, eglin C and desulfatohirudin, e.g. variant HV1. In the hybrid vectors of the present invention, the present promoter and/or signal sequence is operably linked to the polypeptide coding region so as to ensure effective expression of the polypeptide.

The DNA molecules of the present invention may contain selective markers depending on the host which is to be transformed, selected and cloned. Any marker gene can be used which facilitates the selection of transformants due to the phenotypic expression of the marker. Suitable markers are particularly those expressing antibiotic resistance, e.g. against tetracycline or ampicillin, or, in the case of auxotrophic yeast mutants, genes which complement host lesions. Corresponding genes confer, for example, resistance to the antibiotic cycloheximide, or provide for prototrophy in an auxotrophic yeast mutant, for example the ura3, leu2, his3 or trp1 gene. It is also possible to employ as markers structural genes which are associated with an autonomously replicating segment providing that the host to be transformed is auxotrophic for the product expressed by the marker.

Of particular importance are marker genes which complement *A. niger* host lesions, such as the argB gene coding for the ornithine carbamoyl transferase, e.g. derived from *A. niger* or *A. nidulans* (EP 184 438), or *A. nidulans* DNA fragments homologous to the *N. crassa* pyr4 gene (26).

Preferred embodiments of the present invention are hybrid vectors wherein the structural gene, especially the heterologous structural gene is operatively linked to the promoter and signal sequences of the present invention. Such preferred hybrid vector is e.g. pUC19/pelA-IFN AM119, pCG3B11, M13 mp8-PL (SalI-EcoRI) BssHII/BE5, pUBE5, pLHK3, pLHL5 and pLHLT7. Further useful hybrid vectors are pPL29-5 and pPL35-5. Another such preferred hybrid vector is e.g. M13(+)KS/pelA-IFN AM119 (see Examples and Figures).

In another preferred embodiment of the present invention the structural gene, especially the heterologous structural gene is operatively linked directly to the promoter sequences of the present invention. Such preferred hybrid vector is e.g. M13(+)KS/pelAΔss-IFN AM119.

The DNA molecules of the invention and the derivatives thereof, including fragments can be used for screening DNA gene banks or mRNA for further similar DNAs or mRNAs.

Process for the Preparation of the Recombinant DNA Molecules

The invention concerns also a process for the preparation of a recombinant DNA molecule coding for a pectin lyase PLA, PLB, PLC, PLE or PLF expression system or a derivative thereof, comprising culturing a host transformed with a DNA molecule containing a DNA sequence coding for the pectin lyase expression system or a derivative thereof and isolating the desired recombinant DNA molecule or the derivative thereof, or preparing it by an in vitro synthesis.

The culturing of the hosts ist carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae*, or in particular filamentous fungi, such as Aspergillus, e.g. *A. nidulans, A. oryzae, A. carbonarius, A. awamori* and especially *A. niger*. A preferred host is *A. niger* An8, a novel mutant lacking the pyrA gene, as described further below. Transformation of the hosts is carried out by conventional methods.

The DNA sequence coding for the PL expression system is obtained from a filamentous fungi containing such system, in particular from a genomic library thereof or also via the mRNA.

In the following the preparation of the present PL expression systems is described in more detail.

A genomic library can be prepared e.g. by partial digestion of genomic DNA of an *A. niger* strain, e.g. N756 or N400, with e.g. Sau3AI or MboI, and cloning the high molecular weight DNA fragments in a suitable host vector, e.g. the *E. coli* plasmid pUN121 or a lambda vector, e.g. EMBL4. Any other *A. niger* strain producing the desired PLs may serve as source for the genomic library and likewise other suitable vectors may be used as recipient for the fragments.

In order to successfully screen the genomic library for DNA sequences coding for PLs a hybridizing DNA probe is necessary. This can be a synthetic DNA probe if the sequence of the desired PL is known or it can be of a known PL gene or parts thereof.

In order to successfully screen the genomic library for DNA sequences coding for PLI, sequence determination of this enzyme or parts thereof was necessary. PLI was purified from a commercially available mixture of pectinolytic enzymes of *A. niger* (Ultrazym®, Novo Industries) and sequenced. The N-terminus of mature PLI revealed the sequence corresponding to amino acids 20 to 30 of the sequence with SEQ ID No. 2 and a fragment of PLI, obtained by splitting of PLI with cyanogen bromide, revealed the N-terminal sequence corresponding to amino acids 148 to 167 of the sequence with SEQ ID No. 2.

Based on those amino acid sequences a number of DNA probes, i.e. mixtures of DNA sequences coding for parts of the amino acid sequences and the corresponding degenerate DNA sequences, were chemically synthesized and used for screening. Such DNA probes are for example the mixtures 2014 (see SEQ ID No. 4), 2015 (SEQ ID No. 10) or DNA mixture 2060 (SEQ ID No. 11).

Since the total DNA sequence of the PLI gene became known during the course of this work, any part thereof having at least about 14 bp can now be used for screening, which includes also the screening for mRNA coding for the PL system.

For screening purposes the DNA probes are 5' radioactively labelled by methods known in the art using $\gamma^{32}$P-ATP and T4 kinase. Host microorganisms carrying nucleic acids of the present invention as an insert, are identified by hybridisation with the labelled DNA probe on filter replicas of the gene library.

For establishing a sublibrary, clones of the library, showing a radioactive response to the radioactive labelled DNA probe coding for the N-terminal part of PLI can be isolated, cultivated and hybridized with the second DNA probe coding for the N-terminal amino acids of the CNBr fragment, as described before.

Clones showing a hybridisation response to one or both DNA probes are isolated and amplified.

For example, screening with DNA probes 2014 and 2015 revealed 33 and 39 positive clones, respectively. The 72 clones were amplified and the obtained sublibraries rescreened with DNA probe 2060 whereby 3 positive clones could be identified. One clone was selected and named *E. coli* BJ 5183/pCG3B11. It contains plasmid pCG3B11 of which a partial restriction map is shown in FIG. 1. The Sau3AI fragment of pCG3B11 comprises the SpeI-NheI fragment shown in the sequence listing under SEQ ID NO. 1.

Plasmid pCG3B11 can be used for constructing other DNA molecules of the invention by applying conventional genetic engineering techniques.

For example, restriction of pCG3B11 with EcoRI and cloning the two fragments into plasmid pUN121 leads to plasmid pPL 29-5 (FIG. 2) containing the promoter, the signal sequence and the part of the structural PLI gene up to the central EcoRI restriction site at position 1341, and to plasmid pPL35-5 (FIG. 3) containing part of the PLI structural gene starting at position 1342 and the terminator. pPL 29-5 contains further the flanking N-terminal sequences and pPL35-5 the flanking C-terminal sequences of pCG3B11.

Fragments of the inserts of plasmids pPL29-5 and pPL35-5 can be obtained for sequencing by restriction with suitable enzymes, such as AhaIII, PstI, AvaI, HindIII, EcoRI, KpnI, ClaI, NcoI, AccI, SalI, PvuI, SalII, NheI, BglI, EcoRI and EcoRV. The fragments can be subcloned, e.g. into different M13 phages, preferably M13mp8 and M13mp18, and sequenced, e.g. using the M13 Cloning and Sequencing Kit (M13 Sequencing Kit N.4502, Amersham) under the conditions given by the supplier (16). The entire sequence of the 2.7 kb SpeI-NheI fragment, comprising the complete sequence of PLI gene, is given under SEQ ID NO. 1. It comprises 688 nucleotides of the promoter region, 1362 nucleotides of the structural part of the PLI gene and 659 nucleotides of the terminator region. The sequence of pPL29-5, corresponding to amino acid sequence of the N-terminus of PLI as determined by amino acid sequence analysis (Example 1), is preceded by 57 nucleotides coding for the signal peptide corresponding to amino acids 1 to 19 of the sequence with SEQ ID No. 2.

The amino acid sequence of the N-terminus of the C-terminal CNBr fragment of PLI is not continuously encoded by the cloned DNA fragment of pPL35-5. A computer aided search for consensus sequences of exon/intron splice junctions as well as for intron internal sequences (Boel E. et al. (24) and Mount S. M. (25)) leads up to postulate the presence of four introns with length of 65 bp, 62 bp, 63 bp and 57 bp respectively (see SEQ ID No. 1).

One phage, obtained from phages M13mp8 and the 0.8 kb SalI-EcoRI fragment of plasmid pPL29-5, containing 130 nucleotides of the promoter and the N-terminal part of the PLI gene, is designated M13mp8(SalI-EcoRI), and is used in further steps for the preparation of other DNA molecules of the invention.

Such other DNA molecules of the invention comprising fragments of the DNA sequence of the SEQ ID NO. 1 can be constructed as described in FIGS. 4 to 8, whereby, when desired, novel restriction sites can be introduced, e.g. an BssHII restriction site within the signal sequence of the PLI gene. Such DNA molecules are the plasmids or phages, respectively, pUBE5, MBmp8-PL(SalI-EcoRI)BssHII[BE5 (FIG. 4), pLHK3 (FIG. 6), pLHL5 (FIG. 7), M13mp18-PL(SpeI-EcoRI)BssHII/AC5, pLHLT7 (FIG. 8), of which the latter three plasmids contain the structural gene coding for desulfatohirudin.

Mutants containing new restriction sites can be prepared, for example in vitro by site-directed mutagenesis, according to conventional methods [see review article of M. J. Zoller and M. Smith, Methods Enzymol. 100, 468 (1983), D. Botstein and D. Shortle, Science 229, 1193 (1985) or K. Norris et al., Nucl. Acids Res. 11, 5103 (1983)].

For example, a mutant of the present DNA sequences is derived from the M13mp8PL(Sal-EcoRI) phage which comprises the promoter and the secretional signal gene of PLI. Introduction of a new BssHII site into the signal sequence region of M13mp8PL(Sal-EcoRI) gene is performed by using a chemically synthesized primer oligonucleotide, which is complementary to the DNA sequence at positions 725–743 situated near the C-terminal part of the PLI signal sequence, with the exception that at position 734 a C/G transversion (mutagenic primer) is introduced.

The mutated phage, carrying the new BssHII site is designated as M13mp8PL (Sal-EcoRI) BssHII and can be used for the construction of expression vectors for homologous or heterologous genes.

In a corresponding example the desulfatohirudin gene of pML310 (EP 168 342) is recloned into phage M13mp18-PL(SpeI-EcoRI)BssHII/AC5 (FIG. 7 to 8). A HgaI/BssHII linker is constructed, to make the HgaI restriction site of the desulfatohirudin gene of pML301L compatible to the BssHII site of M13mp18-PL(SpeI-EcoRI)BssHII/AC5. The linker DNA is ligated to the cleaved phage DNA. The phage DNA carrying the linker fragment is cleaved with HindIII, which gives two fragments. The 0.7 kb fragment, comprising the signal structure of PLI and the linker fragment is isolated. A suitable replication plasmid, carrying a BamHI restriction site, such as pBR322, is cleaved with BamHI. The gene to be cloned is cleaved out of genomic DNA, plasmid or phage DNA with suitable restriction enzymes and, if necessary, is provided with the required compatible restriction sites.

Another method to make the restriction sites compatible is in vitro mutagenesis, as for example carried out by the construction of pML301L (FIG. 5). A linker containing an HgaI restriction site is constructed and attached to the 5'-terminal of the desulfatohirudin gene.

For higher expression rates, any eukaryotic terminator sequence can be ligated to the end of the structural gene. In a preferred embodiment of the invention, the terminator region of the PLI gene is used. For example an expression vector comprising the terminator site of PLI can be obtained by modification of the above described procedure in the following way. The promoter and secretional signal sequences are obtained from plasmid M13mp18-PL(SpeI-EcoRI)BssHII/AC5. The terminator region is obtained from pPL35-5. M13mp18-PL(SpeI-EcoRI)BssHII/AC5 is cleaved with BssHII and a BssHII-HgaI linker is ligated. In modification, plasmid pPL35-5 is cleaved with PstI, which gives two resulting fragments to which again a suitable linker, compatible with the 3' end of the cloned gene is ligated. The sticky ends of PstI restriction sites are filled up by the enzyme T4-Polymerase and a BamHI linker is added, for example available from Biolabs, New England. The pPL35-5 plasmid is cleaved with NheI and the resulting 0.7 kb fragment, comprising the terminator region of PLI, is isolated. For amplification any plasmid having compatible restriction sites can be used, e.g. pUC18. In the case of pUC18, the plasmid is cleaved with HindIII and XbaI. Four DNA fragments, the M13mp18-PL(SpeI-EcoRI)BssHII/AC5 fragment, carrying the Bss HII-HgaI linker, the 0.7 kB fragment of pPL35-5, carrying the BamHI linker, HindIII/XbaI cleaved pUC18 and the HgaI-BamHI fragment of the desulfatohirudin gene, are ligated to form pLHL7 (FIG. 8).

Bacteria are transformed by a conventional method and the transformants identified by their resistance, e.g. against tetracycline.

In particular the described expression vectors are amplified in suitable *E. coli* host strains, such as HB101, transformed (Ref 37) and selected by methods conventional in the art. The amplified plasmid DNA is isolated from the bacteria by conventional methods, in particular as described by Birnboim & Doly (Ref 23).

In a similar manner other plasmids with other homologous or heterologous genes can be constructed.

Since the total DNA sequence of the PLI gene became available either DNA probes containing the entire gene or any part thereof having at least about 14 bp can now be used also for screening for mRNA coding for other PL genes.

For screening purposes the DNA probes are 5' radioactively*labelled by methods known in the art using $\gamma^{32}$P-ATP and T4 kinase. Host microorganisms carrying nucleic acids of the present invention as an insert, are identified by hybridisation with the labelled DNA probe on filter replicas of the gene library.

Clones showing a hybridisation response to one or more DNA probes are isolated and amplified.

The hybridization conditions used can be more or less stringent, e.g. simply by choosing different temperatures, and in combination with the use of different DNA probes derived from the PLI (or also named PLD) gene, e.g. by measuring the various hybridization responses to the complete 1.6 kbp BamHI/PstI fragment, the 649 bp BamHI/XhoI fragment (the N-terminus fragment) and the 244 bp XhoI/PstI fragment (the C-terminus fragment) from pCG3B11 or pGW840 (SEQ ID NO. 1 or FIG. 12), the clones can be divided into different classes based on their degree of homology (Tables II or IV). Five λ-vectors (λ-PL113, λ-PL122, λ-PL109, λ-PL102 and λ-PL116) were finally identified, restricted and subclones of their pel genes prepared in pBR322 leading to plasmids pGW820, pGW830, pGW850, pGW860 and pGW880 (FIGS. 9 to 11, 13 or 14). The five genes of these clones are called pelA, pelB, pelC, pelE and pelF respectively.

The genes can be sequenced. Full sequences of pelA, pelB and pelC are represented by the sequences SEQ ID NO. 3, 5 and 7, respectively.

A computer aided search for consensus sequences of exon/intron splice junctions as well as for intron internal sequences (Boel E. et al. (24) and Mount S. M. (25)) leads up to postulate, like in pelD, the presence of four introns in pelA and pelB and of three introus in pelC.

The plasmids pCG3B11, pGW820, pGW830, pGW840, pGW850, pGW860 and pGW880 are used to prepare other recombinant DNA molecules of the invention. Such other DNA molecules are prepared in conventional manner by applying conventional restriction enzymes, linkers, ligation, amplification and isolation processes.

For example, the plasmid pGW820 is restricted with HindIII. The 3.9 kbp HindIII fragment is subcloned into the HindIII site of pBR322. The 3.3 kbp BamHI- HindIII fragment of the obtained plasmid pGW822 containing the pelA gene is cloned into the BamHI and HindIII site of the vector pUC19 to give a vector called pUC19/pelA. The structural gene of pelA is excised by digestion with SalI and PstI. Into the remaining fragment containing the pelA promoter, signal and terminator sequences is ligated between the signal and terminator sequence a gene coding for the interferon hybrid BDBB by means of a suitable linker. The obtained plasmid is named pUC19/pelA-IFN AM119 (FIG. 19) and contains the promoter and signal sequence of pelA the IFN BDBB gene and the pelA terminator attached to the HindIII-BamHI fragment of pUC19. This plasmid is cotransformed with pCG59D7 into the uridine auxotrophic *A. niger* mutant An8 (DSM 3917). Transformants are selected in minimal medium containing arginine and Bacto-Agar and analyzed for interferon expression.

In an other embodiment of the invention the signal sequence of pelA may be deleted. The obtained plasmid is named M13(+)KS/pelAΔss-IFN AM119 and contains the promoter sequence of pelA, the IFN BDBB gene and the pelA terminator attached to the HindIII-BamHI fragment of Bluescript M13(+)KS vector. This plasmid is cotransformed with pCG59D7 into the uridine auxotrophic *A. niger* mutant An8 (DSM 3917). Transformants are selected in minimal medium containing arginine and Bacto-Agar and analyzed for interferon expression.

Mutants containing new restriction sites can be prepared, for example in vitro by site-directed mutagenesis, according to conventional methods [see review article of M. J. Zoller and M. Smith, Methods Enzymol. 100, 468 (1983), D. Botstein and D. Shortle, Science 229, 1193 (1985) or K. Norris et al., Nucl. Acids Res. 11, 5103 (1983)].

For higher expression rates, any eukaryotic terminator sequence can be ligated to the end of the structural gene.

Bacteria are transformed by a conventional method and the transformants identified by their resistance, e.g. against tetracycline.

In particular the described expression vectors are amplified in suitable *E. coli* host strains, such as HB101, transformed and selected by methods conventional in the art. The amplified plasmid DNA is isolated from the bacteria by conventional methods, in particular as described by Birnboim & Doly (23).

In a similar manner other plasmids with other homologous or heterologous genes can be constructed.

The DNA molecules of the present invention can also be prepared by an in vitro synthesis according to conventional methods. The in vitro synthesis is especially applicable for the preparation of smaller fragments of the PL expression system, e.g. of the DNA sequences coding for the promoter or the signal sequence of the PLs, or mutants thereof.

DNA molecules of the invention comprising a PL promoter and optionally a PL signal sequence, a PL structural gene, any other heterologous structural gene and/or a PL terminator can also be used to transform filamentous fungi, such as Aspergillus, Penicillium or Cephalosporium, e.g. *A. nidulans, A. oryzae, A. carbonarius, A. awamori* and especially *A. niger.*

In order to allow selection of the transformed from the non-transformed fungi, the DNA molecules of the invention carry a selection marker or, alternatively, the fungi are cotransformed with a second vector containing such marker. As in other systems such selection marker is an expressible, structural gene, the expressed polypeptide of which (an enzyme) provides resistance against compounds toxic to the transformant or which completes the enzyme system of a mutant lacking such essential polypeptide. Such marker genes are for example the known qa-2, pyrG, pyr4, trpC, amdS or argB genes.

Within the frame of the invention a novel marker gene, named pyrA, was isolated from the genomic library of *A. niger*, which is related to and has similar function as pyrG of *A. nidulans* and pyr4 of *N. crassa*, namely producing the enzyme orotidine 5'-phosphate decarboxylase. This enzyme catalyses the decarboxylation of orotidine 5'-phosphate to uridylic acid (uridine 5'-phosphate) and also of fluoro-orotic acid to the toxic fluoro-uridine. An *E. coli* clone containing the pyrA gene was identified by hybridization with the 1.1 kb Hind III fragment of pDJB2 (24) containing part of the pyr4 gene, however, DNA of any other pyr gene coding for orotidine-5'-phosphate decarboxylase may be used. From a positive clone named *E. coli* BJ5183/pCG59D7, the plasmid pCG59D7, comprising the pyrA gene, was isolated and used for cotransformation of an *A. niger* pyrA$^-$ mutant. Such pyrA$^-$ mutant is defective in the orotidine 5'-phosphate decarboxylase gene and therefore is unable to produce the corresponding enzyme. Such mutant was prepared by treating conidiospores of *A. niger* N756 under mutating UV-irradiation and colonies surviving in the presence of fluoro-orotic acid and uridine are selected. Colonies surviving in the presence of fluoroorotic acid and absence of uridine are eliminated. The remaining uridine-requiring mutants, according to their ability of being transformable, belong to two complementation groups pyrA and pyrB, represented by mutants An8 and An10, respectively. They are treated in the form of protoplasts thereof under transforming condition with the pyrA containing plasmid pCG59D7. Only the An8 colonies were found to be transformed and to contain the pyrA gene as evidenced by the hybridizing ability of digested DNA thereof with DNA of pUN 121.

The invention concerns also the selection marker plasmid pCG59D7, a host containing it and the pyrA mutant *A. niger* An8 and processes for their preparation.

The invention concerns further hosts transformed with the hybrid vectors of the invention and methods for their preparation. Such transformants are for example bacteria, such as *E. coli*, or filamentous fungi, such as Aspergillus, Penicillium or Cephalosporium, and in particular *A. nidulans, A. oryzae, A. carbonarius, A. awamori* or preferably *A. niger*, e.g. *A. niger* An8. The invention concerns also a method for the preparation of such transformants comprising treatment of a host under transforming conditions with a recombinant DNA molecule, especially a hybrid vector, of the invention, optionally together with a selection marker gene and selecting the transformants.

The invention concerns also the use of the recombinant DNAs or a derivative thereof for the preparation of hybrid vectors which express useful homologous or heterologous polypeptides. Examples of genes encoding such useful polypeptides are given hereinbefore.

The invention concerns further a method for the preparation of polypeptides, characterized in that a hybrid vector of the invention is expressed in a suitable host. When required, the polypeptide is isolated in conventional manner. Depending on the construction of the vector the products are either expressed, or, if a signal sequence is present, are expressed and secreted.

This method comprises the production of useful homologous or heterologous proteins in a suitable host, e.g. Aspergillus species, by cultivating a host transformed with an expression hybrid vector. Examples of genes encoding such proteins are given hereinbefore.

It is now also possible to produce the single polypeptides PLA, PLB, PLC, PLD, PLE or PLF, that means in pure form and uncontaminated by any other PL, whereby various methods can be applied. E.g., one method for the production of a single polypeptide selected from the group consisting of PLA, PLB, PLC, PLD, PLE and PLF is characterized in that a host which is not capable of expressing any pectin lyase PL is transformed with a DNA expression vector expressing the product of PLA, PLB, PLC, PLD, PLE or PLF.

A host not capable of expressing any pectin lyase PL is either a microorganism having no corresponding gene, e.g. a PL$^-$ Aspergillus strain, another non-Aspergillus fungi or any other eukaryotic or prokaryotic microorganism, or an Aspergillus strain whose production of PLs is supressed in an appropriately conditioned growth medium. For example, a single PL gene can be expressed under the control of the glucoamylase promoter in *A. niger* or *A. awamori,* under the control of the PHO5 promoter in *S. cerevisiae* or under the control of a PL promoter in a PL$^-$ *A. niger* strain.

BRIEF DESCRIPTION OF THE FIGURES

FIG. 6 shows the construction of pLHK3 containing part of the PLI promoter, the signal sequence with the BssHII restriction site, the linker BssHII-HgaI,and the desulfatohirudin gene

FIG. 18 shows the homology at the amino acid sequence level between PLD, PLA, PLB and PLC (SEQ ID NOS:2,4,6 and 8, respectively)

Figure 1:
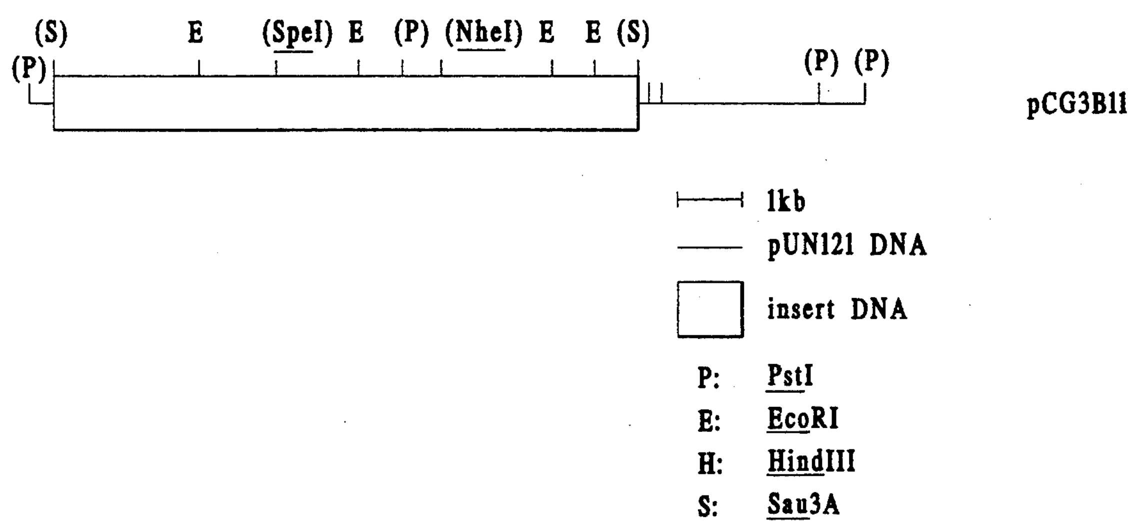
FIG. 1 shows the restriction map of plasmid pCG3B11 containing a Sau3AI fragment of the *A. niger* strain N756

The abbreviations have the following meanings:

| | |
|---|---|
| Amp | ampicillin |
| ATP | adenosine triphosphate |
| bp | base pairs |
| BSA | Bovine serum albumin |
| cpm | counts per minute (radioactive decay) |
| dATP | 2'-deoxyadenosine triphosphate |
| dCTP | 2'-deoxycytidine triphosphate |
| dGTP | 2'-deoxyguanosine triphosphate |
| dTTP | 2'-deoxytbymidine triphosphate |
| dNTP | mixture of DATP, DCTP, DGTP and DTTP |
| CIP or CIAP | alkaline phosphatase from calf intestine |
| DNA | deoxyribonucleic acid |
| DTT | 1,4-dithiothreitol |
| EDTA | ethylenediaminetetraacetic acid disodium salt |
| EGTA | bis-(aminoethyl)-glycolether)N,N,N',N'-tetraacetic acid |
| hrs | hours |
| IPTG | isopropyl-B-D-thio-galactopyranoside |
| kb | kilobases |
| LMP | low melting point |
| min | minutes |
| mOsm | milliosmoles |
| PEG | polyethyleneglykol |
| PL | pectin lyase I |
| PTH | phenylthiohydantion |
| RF-DNA | double-stranded replicative form DNA |
| RNA | ribonucleic acid |
| RT | room temperature |
| rpm | revolutions per minute |
| SDS | sodium dodecyl sulfate |
| ss | single-stranded |
| Tc | Tetracyline |
| Tris | tris(hydroxymethyl)-aminomethane |
| tRNA | transfer RNA |
| U | units |
| μg | microgram |
| V | Volt |
| vol | volume |
| X-GAL | 5-bromo-4-chloro-3-indonyl-β-galactoside |

Buffers, media, reagents:

| | |
|---|---|
| ss-Denhardt | 0.02% ficoll (Sigma), 0.02% polyvinylpyrrolidone (Sigma), 0.02% BSA (Sigma), 100 μg/ml denaturated salmon sperm DNA (Sigma) |
| HHA B/g | 10X restriction-enzyme buffer used for BamHI, BglII, HindIII, MboI, PstI and XhoI digests, containing 60 mM Tris-HCl (pH 7.4), 60 mM β-mercaptoethanol, 60 mM $MgCl_2$, 500 mM NaCl, 0.1% BSA, 0.1% gelatin |
| EcoRIbuffer | 5X restriction-enzyme buffer used for EcoRI digests, containing 500 mM Tris-HCl (pH 7.2), 25 mM $MgCl_2$, 250 mM NaCl, |

-continued

| | |
|---|---|
| | 0.05% BSA, 0.05% gelatin |
| HgaI buffer | 50 mM NaCl, 10 mM $MgCl_2$, 1 mM DTT, 100 μg/ml BSA, 6 mM Tris-HCl pH 7.4 (final concentration). |
| IPTG | 100 mM isopropyl-β-thio-galactopyranoside (23.8 mg/ml) in $H_2O$ |
| LB medium | 1% Bacto-tryptone (Difco), 0.5% Bacto yeast extract (Difco), 170 mM NaCl, adjusted to pH 7.5 with NaOH |
| LC medium | 1% trypticase peptone (BBL), 0.5% yeast extract (BBL), 0.8% NaCl, 1 ml Tris-HCl pH 7.5 per litre |
| ligation buffer | 20 mM Tris-HCl, 10 mM $MgCl_2$, 10 mM dithioerythritol, 0.6 mM ATP, pH 7.6 |
| minimal medium | 1.05% $K_2HPO_4$, 0.45 $KH_2PO_4$, 0.1% $(NH_4)_2SO_4$, 0.05% for *E. coli* sodium citrate. $2H_2O$, 1 mM $MgSO_4$, 1 mM thiamine-HCl, 0.2% glucose |
| 2XTY medium | per litre 16 g trypticase peptone (BBL), 10 g yeast extract, 5 g NaCl |
| TBE-buffer | 1 litre contains 10.8 g Tris, 5.5 g boric acid, 4 ml 0.5 M EDTA (pH 8.0) |
| TE buffer | 10 mM Tris-HCl (pH 8.0), 1 mM EDTA (pH 8.0) |
| low TE buffer | 10 mM Tris-HCl (pH 8.0), 0.1 mM EDTA (pH 8.0) |
| X-gal or X-GAL | 2% (5-bromo-4-chloro-3-indolyl-β-galactoside) in dimethylformamide |
| SSC | 0.15 M NaCl, 0.015 M sodium citrate |
| SOC medium | 2% Bacto Tryptone (Gibco), 0.5% Yeast-Extract (Gibco), 10 mM NaCl, 2.5 mM KCl, 10 mM $MgCl_2$, 5 mM $MgSO_4$, 20 mM Glucose |
| kinase buffer | 50 mM Tris-HCL, 10 mM $MgCl_2$ 5 mM DDT (pH 7.5) |
| X-gal plates | 0.002% X-Gal, 0.07 mM IPTG |
| NET | 0.15 M NaCl, 0.015 M Tris.HCl (pH 7.5) 1 mM EDTA |
| minimal medium for *E. coli* | 0.6% $Na_2HPO_4$, 0.1% $NH_4Cl$, 0.05% NaCl, 1 mM $MgSO_4$, 0.01 mM $CaCl_2$, 1 mM thiamine-HCl, 0.2% glucose |
| minimal medium for *A. niger* | 1 litre contains 1.5 g $KH_2PO_4$, 0.5 g KCl, 0.5 g $MgSO_4.7H_2O$, 4.0 g $NH_4Cl$, 10.0 g glucose, traces of $FeSO_4$,, $MnSO_4$, $ZnCl_2$, adjusted to pH 6.5 with NaOH |
| complete medium for *A. niger* | Mycophil-Agar (BBL) or minimal medium plus 0.2% trypticase peptone for (BBL) 0.1% casaminoacids (Difco), 0.1% yeast extract (BBL), 0.05% ribonuleic acid sodium salt from yeast (ICN, Cleveland, USA), 2 ml vitamin solution per litre |
| vitamin solution | per 100 ml 10 mg thiamine, 100 mg riboflavin, 10 mg panthotenic acid, 2 mg biotin, 10 mg p-aminobenzoic acid, 100 mg nicotinamide, 50 mg pyridoxin-HCl |
| PCT | 25% polyethylene glycol 6000 (Merck, Darmstadt) in 10 mM Tris-HCl (pH 7.5), 50 mM $CaCl_2$ |
| sporulation medium | 10 g/l pbytone peptone, 10 g/l glucose, 10 g/l agar |

For plates all media are solidified by addition of 1.5% agar (BBL), for topagar(ose) 0.7% agar (BBL) or agarose (Seakem) is used.

| | |
|---|---|
| PBS | per litre 0.37 g $NaH_2PO_4$, 2.7 g $Na_2HPO_4$, 8.5 g NaCl |
| PSB | 10 mM Tris-HCl (pH 7.6), 100 mM NaCl, 10 mM $MgCl_2$, 0.05% gelatine |
| LDB | 10 mM Tris-HCl (pH 7.6), 100 mM NaCl, 10 mM $MgCl_2$ |

The following strains are used:

| | |
|---|---|
| *A. niger* | N400 wildtype |
| *A. niger* N593 | cspA, pyrA |
| *A. niger* N756 | selected for high production of pectinase complex enzymes |
| *A. niger* AN8 | DSM 3917, uridine anxotrophic mutant of *A. niger* N756 |
| *E. coli* NM539 | metB, supE, hsdM+, hsdR−, supF, (P2cox3) |
| *E. coli* MH1 | ara D139, ΔlacX74, galU, galK, hsr−, hsm+, strA, |
| *E. coli* JM103 | Δlac-pro, thi, strA, supE, endA, sbcB, hsdR4, F[1], traD36, proAB, laclq, ZΔM15 |
| *E. coli* JM109 | Δ(lac-proAB), recA1, endA1, gyrA96, thi, hsdR17, supE44, relA1, λ−, [F', traD36, proAB, |

-continued

| | |
|---|---|
| | lacI$^q$, ZΔM15] |
| *E. coli* CJ236 | (dut-1, ung-1, thi-1, relA-1; pCJ105(Cm$^r$); BIO-RAD Muta-Gene M13 in vitro mutagenesis kit) |
| *E. coli* MV1190 | [Δ(lac-proAB), thi, supE, Δ(srl-recA)306::Tn10(tet$^r$) (F':traD36, proAB, lac 1$^q$ZΔM15)]. Strain MV1190 is described in the manual for the BIO-RAD MUTA-GENE M13 in vitro mutagenesis kit |

*E. coli* strain HB101: F−, hsdS20(r−Bm-B), recA13, ara14, proA2, lacY1, galK2, rpsL20(str$^R$), xyl-5, mtl-l, supE44, λ− (Maniatis et al. (Ret5))
*E. coli* strain BJ5183: F−, endA, sbcB−, recBC−, galK, met−, str$^R$, thi-1, bioT, hsdR($r_K^-$, $m_K^+$), λ− (Hanahan (37)).
*E. coli* strain JM101: supE, thi, Δ(lac-proAB), (F', traD36, proAB, lac19ZΔM15) (Yanisb-Perron et al. (47))

The following vectors are used:

EMBL4

EMBL4 is a lambda replacement vector with a cloning capacity of 9–23 kbp (Frischauf et al., ref. 2). It contains a multiple cloning region between the lambda arms and the nonessential stuffer region. This allows multiple restriction enzyme digestions to be performed in a manner such that religation of the stuffer to the vector arms is reduced as the foreign DNA of interest is inserted. The vector also makes use of the Spi phenotype to provide a direct selection for recombinants (Zissler et al., ref. 20).

pDJB2 plasmid

This plasmid has been described by Ballance and Turner (26)

pBR322

Plasmid pBR322 carries genes for resistance to the antibiotics ampicillin (amp$^R$) and tetracycline (tet$^R$). The plasmid carries several unique cloning sites, of which some are located in either the amp or tet gene so that insertion of cloned DNA leads to anti biotic-sensitive bacteria.

pEMBL18 and pEMBL19

These plasmids have been described by Dente et al. (refs. 7, 8).

pGW613

This plasmid has been described by Goosen et al. (ref. 12).

M13mp phage

The M13mp18 and M13mp19 vectors (Norrander et al., ref. 21) are derivatives of the single-stranded DNA bacteriophage M13 and are designated to facilitate DNA sequencing by allowing cloning of DNA fragments at a versatile polylinker site and the cloning of the same restriction fragment in both possible orientations. Sequences cloned into these vectors can readily be used as templates for sequencing reactions or the production of single-stranded probes using standard oligodeoxyribonucleotide primer and the Klenow fragment of the *E. coli* DNA polymerase I. The vector DNA is carrying the *E. coli* lac-operon promoter and the gentic information of the first 145 amino acids of β-galactosidase. The polylinker sequences containing multiple restriction sites are inserted into the lacZ sequence. The polylinker retains the lacZ reading frame and the vector gives allelic complementation of a LacZα host strain, yielding blue plaqes on plates containing IPTG and X-gal. Recombinant phages containing inserts that destroy the reading frame or otherwise interfere with expresssion of the lacZα peptide are revealed as colorless plaques.

M13(+)KS (Bluescript) (STRATAGENE, San Diego, Calif, USA)

dsDNA vector, comprising the origin of replication of M13 phage. In presence of a helper phage, e.g. M13K07 (ref. 29) or R408 (ref. 9), (+)-strand of the vector is replicated, packaged and set free into the medium.

M13 K07

Helper M13 phage for M13(+)KS. Described in Mead et al. (ref. 29).

R408

Helper M13 phage for M13(+)KS. Described in Russell et al. (ref. 9).

pUC18 plasmid

The pUC18 plasmid (Ret 21) can be used for cloning DNA sequences in the lacZ$\alpha$ region providing a detection for transformants containing recombinant plasmids on the basis of their Lac phenotype. Bacteria harboring plasmids without inserts make blue colonies on indicator plates (plates with X-gal) whilst those harboring recombinant plasmids make white colonies. Plasmid pUC18 contains unique cloning sites in the lacZ$\alpha$ region fitting to those of M13mp18 phage. The plasmid carries a gene for $amp^R$.

pML 310 plasmid pML 310 is described in the European Patent Application No. 0168342, pML310 is characterized through $amp^R$, the trp promoter and a gene coding for desulfatohirudin, a thrombin inhibitor which naturally occurs in leeches.

pUN121 plasmid

Plasmid pUN121 [(Nilsson et al. (Ret 36)]can be used as a cloning vector that allows positive selection of transformants harboring plasmids with DNA inserts. The plasmid contains the cI gene of bacteriophage lambda, and the tet gene. Bacteria harboring pUN121 are sensitive for tetracycline since the tet gene is transcribed from the right promoter of bacteriophage lambda and this promoter can be repressed by the cI-encoded repressor. Insertion of DNA fragments in one of the sites in the cI gene inactivates the repressor gene, yielding tetracycline-resistant transformants. In addition plasmid pUN121 has a functional amp gene so that amplification of plasmid DNA can be performed under selective conditions.

EXAMPLE 1

Isolation and characterisation of pectine lyase I

EXAMPLE 1.1

Amino acid sequence determination of the N-terminal part of pectin lyase I

Pectin lyase I is purified from Ultrazym® (a mixture of pectinolytic enzymes obtained from *A. niger*, Novo Industries, Copenhagen) in analogy to the method described by F. E. A. van Houdenhoven (Ref 18). Two mg of pectin lyase I are dialyzed against several liters of distilled water and subsequently lyophilized. The protein is dissolved in 1.5 ml 100 mM $NaHCO_3$, pH 10.0 and kept at room temperature for 3 hrs. This treatment turns out to increase the number of steps, which can be reliably sequenced by the automatic Edman degradation method (Ref 31). After the alkaline treatment the protein is dialyzed against 1 liter of distilled water, 1% formic acid and distilled water subsequently. Automatic Edman degradation is performed in a Beckman spinning-cup sequenator, model 890 C. The intact reduced and carboxymethylated protein is degraded using a quadrol single-cleavage program (modification of Beckman program 072172 C). The degradation of the peptide is carried out using a dimethylbenzylamine single-cleavage program (Beckman program 082773) or the program of Hunkapiller and Hood. To prevent wash-out of the peptide, 2.5 mg of cod parvalbumin is used as a carrier (Ret 32). Phenylthiohydantoin derivatives of amino acids are identified by high-performance liquid chromatography according to the method of Frank and Strubert (Ref 33). The N-terminal amino acid sequence for pectin lyase I is corresponding to the amino acids 20 to 30 of the sequence with SEQ ID No. 1.

EXAMPLE 1.2

Preparation of cyanogen bromide fragments of pectin lyase I

Reduction and S-carboxymethylation of pectin lyase I is performed according to Crestfield et al. (Ref 34). 3 g urea (ultra pure) are dissolved in 5 ml of distilled water and stirred with 0.5 g of a mixed-bed ion-exchanger (Biorad Ag 50 1-X8) for 1 h. After removal of the ion-exchange beads, 10 mg EDTA and 200 mg Tris are added to 4 ml of the urea solution and-the pH is adjusted to 8.5 with HCl. The solution is filled up to a final volume of 5 ml in a vial with distilled water. Then 5–20 mg of pectin lyase I purified as described by F. E. A. van Houdenhoven (Ref 18) are added and the vial is maintained under a nitrogen barrier.

Finally 33 $\mu$l of $\beta$-mercaptoethanol are added and the reduction is continued for 4 hrs at room temperature under a nitrogen barrier. 0.33 ml of a freshly prepared solution (0.268 g iodoacetic acid in 1 ml 1N NaOH) are added under nitrogen to the reaction mixture and the mixture is kept in the dark for 15 min at room temperature.

The reaction is stopped by addition of $\beta$-mercaptoethanol. Subsequently the carboxymethylated protein is applied to a Sephadex G-25 gel filtration column (100 ml bed volume) which is wrapped in aluminum foil and eluted with 0.5% formic acid. The protein fractions are pooled and lyophilized.

The carboxymethylated pectin lyase I (2–10 mg) is dissolved in 70% formic acid and solid cyanogen bromide is added in approx. hundred fold molar excess to methionine of which 1 residue occurs per pectin lyase I. The reaction mixture is stirred continuously for 24 hrs at room temperature in a closed reaction vial. Samples of 5 $\mu$l are taken at regular time intervals and analyzed on 15% SDS-PAGE to check the extent to which the protein is split. After 24 hrs water is added and the preparation is partially evaporated by flushing with nitrogen. This step is repeated to remove the formic acid.

The SDS-PAGE analysis identifies, besides some residual pectin lyase I, two cyanogen bromide peptides, CBI and CBII with apparent molecular weight of 16.5 kD and 30 kD. Purification of these fragments is performed by gel permeation chromatography using a Sephacryl-S200 column (length 190 cm, O1 cm) equilibrated in 20 mM sodium phosphate buffer pH 6.0, 100 mM NaCl, 4M urea and 1% (v/v) $\beta$-mercaptoethanol. The CB II fragment appears in two peaks, one peak eluting even before the residual intact protein which therefore must represent an aggregate and another peak in between the intact protein and the small CBI fragment.

EXAMPLE 1.3

Amino acid sequence determination of the N-terminal part of CB II of pectin lyase I 200 μg of the purified non-aggregated CB II fragment of Example 1.2. are used for the automatic Edman degradations (Ref 31) using a Beckman spinning-cup sequenator. Conversion to the PTH amino acids is realized after evaporation of the fractions and the addition of 200 μl 2N HCl in methanol to the residue for 15 min at 65° C. The solution is then evaporated again and the residue is taken up in 50 μl THF/$CH_3CN$ (1:1). The PTH-amino acids are identified by HPLC using a Zorbax $CN^R$ column (Du Pont) according to R. Knecht et al. (Ref 35).

The N-terminal amino acid sequence of CB II is corresponding to amino acids 148 to 167 of the sequence with SEQ ID No. 1, however, the amino acids in positions 162 and 166 have not been identified.

EXAMPLE 2

Construction of a genomic library of *Aspergillus niger*

EXAMPLE 2.1

Isolation of high molecular weight DNA from *Aspergillus niger* N756

The isolation of high molecular weight *A. niger* DNA is done according to Yelton et al. (Ref 1). Conidiospores of *A. niger* strain N 756 are inoculated in 200 ml minimal medium containing 0.1% arginine and shaken in 500 ml flasks with one well at 28° C. on a rotary shaker for 2–3 days. The mycelium is harvested by filtration, washed with cold sterile water, frozen and powdered in liquid nitrogen. The cells are rapidly suspended in 20 ml 50 mM EDTA pH 8.5, 0.2% SDS and 20 μl diethylpyrocarbonate and lysated by vigorously shaking for 1 min at room temperature. The lysate is heated to 68° C. for 15 min, cooled to room temperature and centrifuged for 15 min at 12000 g at RT. 16 ml of the supernatant are transferred to a new tube and after addition of 1 ml 8M potassium acetate pH 4.2 left on ice for 1 hr. The precipitate is centrifuged at 25000 g for 15 min at 4 C.°. 12 ml of the supernatant are recovered and the nucleic acids precipitated with 12 ml of isopropanol. The precipitate is pelleted by centrifugation for 1.5 min at 12000 g and the pellet resuspended in 2 ml TE containing 10 μg/ml RNAseA (Boehringer, Mannheim). The DNA fragments are extracted with chloroform/phenol and precipitated with ethanol as described by Maniatis et al. (Ref 5) at pages 458–459 and 461–462.

EXAMPLE 2.2

Cloning of high molecular weight DNA fragments from *Aspergillus niger* N756 into pUN121

The high molecular weight DNA of Example 2.1. (100 μg) is precipitated by centrifugation and the pellet is resuspended in 750 μl buffer consisting of Tris-HCl 6 mmol/l, NaCl 50 mmol/l, $MgCl_2$ 6 mmol/l, pH 7.5. Partial digestions are carried out with Sau3AI, the concentrations being in the range of 0.25–0.01U/μg for 60 min at 37° C. The reactions are terminated by addition of EDTA to final concentrations of 20 mM.

The partially digested DNA fragments are separated on a 0.45% agarose gel. Lambda DNA digested with HindIII is used as marker to determine the size of the partially digested DNA fragments. The gel region containing the desired fragments in the range of 15 kb to 20 kb is cut out and transferred to the sample well of an ISCO electrophoretic concentrator (ISCO GmbH), covered with 0.1TBE and electroeluted at 1 Watt for 90 min. The DNA fragments are extracted with chloroform/phenol and precipitated with ethanol.

4 μg of the partially digested DNA fragments are resuspended in $H_2O$ and ligated for 15 hrs at 15° C. to 1 μg of pUN121 plasmid DNA (Nilsson et al. (9)), linearized with BclI, in a total volume of 106 μl ligation buffer with 6U T4 DNA ligase (Boehringer, Mannheim). 10 μl aliquots of this annealing mixture are added to 210 μl of competent *E. coli* BJ5183 cells, which have been prepared for transformation as described by Hanahan (10). The cells are kept on ice for 30 minutes and heated to 42° C. for 90 sec, replaced on ice for 2 min, 800 μl SOC-medium are added and the cells are incubated at 37° C. for 1 hr. The cells are spread on 10 cm agar plate containing LB-medium supplemented with 8 mg/l tetracyclin (SIGMA). The plates are incubated at 37° C. for 16 hrs. About 6000 transformed colonies are obtained characterized by their tetracyclin resistance. The efficiency is about 12000 to 20000 tetracycline-resistant colonies per μg of pUN121DNA.

The plasmid analysis of 11 randomly chosen recombinant clones indicates an average DNA insert of 10 kb. To represent the genome of *A. niger* ($4.5\times10^7$ bp) in the library almost 4 times, 15360 tetracyclin resistant colonies are picked and grown individually over night in the wells of microtiter dishes in LB-medium supplemented with 8 mg/l tetracycline. After incubation glycerol is added to 50% v/v and the microtiter dishes are stored at −70° C.

EXAMPLE 3

Screening the genomic library of *A. niger* N756 for nucleic acids related to PLI

EXAMPLE 3.1

Preparation of filter replicas of the library

For the isolation of the pectin lyase I gene from the DNA library obtained as described in Example 2.2., filter replicas from the 15360 chosen transformed *E. coli* BJ5183 cells are made following the method described by Gergen et al. (Ref 38). The cells are transferred from the microtiter dishes to agar plates supplemented with 8 mg/l tetracycline by using a stamp and grown over night at 37° C. Conveniently cut Whatman 541 filter papers (114×175 mm per 192 clones) are placed on top of the colonies. After 2 hrs at 37° C. the filters are transferred to LB plates containing 250 mg/ml chloramphenicol (Sigma, St. Louis, USA) and incubated over night at 37° C. The filters are washed twice in 0.5M NaOH, twice in 0.5M Tris HCl, pH 7.4, washed twice in SSC and are air dried. The filter replicas can be used for several hybridisation experiments, each preceeded by the above mentioned washing steps.

EXAMPLE 3.2

Synthesis of oligonucleotide mixtures

The oligonucleotides for screening the DNA library of *A. niger*, obtained as described in Example 2.2., are synthesized corresponding to the amino acid sequence determined in Examples 1.1. and 1.3. by using the phosphoramidite method (M. H. Caruthers (Ref 10), with an Applied Biosystem (Model 380B) oligonucleotide synthesizer.

3.2.1

Synthesis of an oligonucleotide coding for the N-terminus part of pectin lyase I of *Aspergillus niger*

The oligonucleotide coding for the N-terminus of the pectin lyase I protein is synthesized with respect to its aminoacid composition as determined in Example 1.1. Because of genetic degeneration 256 oligonucleotides are required to comprise all possibilities.

Two separate mixtures of oligonucleotides are chemically synthesized, because for technical reason it is necessary to reduce the number of nucleotides in the mixture. Both contain 128 different oligonucleotides, each being a complementary strand of the strands coding for the amino acid sequence corresponding to amino acids 25 to 30 of the sequence with SEQ ID No. 1. In the following they are named mixture 2014 and 2015.

Mixture 2014 is depicted in the sequence listing under SEQ ID No. 9, mixture 2015 under SEQ ID No. 10.

EXAMPLE 3.2.2

Synthesis of an oligonucleotide coding for the N-terminus part of the C-terminal fragment of the CNBr decomposed pectin lyase I protein The oligonucleotide coding for the N-terminus part of the C-terminal fragment of the CNBr decomposed pectin lyase I protein is synthesized with respect to its amino acid composition as determined in Example 1.3. A mixture of 108 oligonucleotides is synthesized being a complementary strand of the strands coding for the amino acid sequence corresponding to amino acids 148 to 152 of the sequence shown under SEQ ID No. 1. The mixture is named as 2060 and is shown under SEQ ID No. 11.

EXAMPLE 3.2.3

$^{32}$P-labelling of the oligonucleotide mixtures 67 pmoles of each oligonucleotide mixture 2014, 2015 and 2060 of Example 3.2.1 and 3.2.2 are 5'labelled using 50 pmoles of [$\gamma^{32}$P]ATP (Amersham, Buckinghamshire, England, 5000 Ci/mmol). The incubation is carried out at 37° C. with 150 units T4 polynucleotide kinase (New England, Nuclear) in 500 $\mu$l kinase buffer. The ligation reaction of radioactive labelled ATP to the oligonucleotides is detected by running an aliquot of the reaction mixtures on a 20% polyacrylamide gel followed by autoradiography.

EXAMPLE 3.3

Screening of the gene library with radioactive labelled oligonucleotide mixtures 2014 and 2015

The screening of the gene library is carried out by hybridisation with the radioactively labelled oligonucleotide mixtures 2014 and 2015 of Example 3.2.1 Batches of 20 filter replicas of the gene library (Example 3.1.) are wetted in 6×NET and are prehybridized in 200 ml 6×NET, 1×ss-Denhardt, 0.1% SDS at 49.3° C. for 4 hrs. Then 67 pmoles of the radioactively labelled oligonucleotide mixture 2014 are added and the hybridisations carried out over night at 49.3° C. The same procedure is carried out using radioactively labelled oligonucleotide mixture 2015. The filters are washed two times for 5 minutes in 2×SSC, 0.1% SDS at room temperature, two times for 1 hr in 2×SSC, 0,1% SDS at 49.3° C. and one time for two hrs in 0.2×SSC, 0.5% SDS at 49.3° C. The filters are air dried and autoradiographed for 3 days using KODAK X-omat SO282 films.

With the oligonucleotide mixture 2014 33 clones and with the oligonucleotide mixture 2015 39 clones are found, which give a rather strong hybridisation response. To establish a sublibrary the 72 clones are grown up in a new microtiter dish and transferred to Whatman 541 filter as described in Example 3.1. Two filter replicas of the sublibrary are hybridized with both probes individually, washed and autoradiographed. With the oligonucleotide 2014 mixture only the clones obtained by hybridisation with the oligonucleotide 2014 mixture hybridize. Likewise with the oligonucleotide 2015 mixture only the clones obtained by hybridisation with the oligonucleotide mixture 2015 hybridize.

EXAMPLE 3.4

Screening the sublibrary with the oligonucleotide mixture 2060

The filter replicas of the sublibrary (72 clones), obtained in Example 3.3, are wetted in 6×NET and prehybridized for 4 hrs in 15 ml 6×NET, 1×ss-Denhardt, 0.1% SDS at 32° C. 8 pmoles of oligonucleotide mixture 2060, radioactive labelled as described in Example 3.2.3, are added and the hybridization carried out over night at 32° C. The filters are washed two times for 5 minutes each in 2×SSC, 0.1% SDS at room temperature, two times for 1 hour each in 2×SSC, 0.1% SDS at 32° C. and one time for two hours in 0.2×SSC, 0.5% SDS at 32° C. The filters are air dried and autoradiographed for 3 days using KODAK X-omat SO282 films. 3 positive clones are found, all belonging to the group that hybridize with the 2014-probe as described above; one clone is named *E. coli* BJ5183/pCG3B11 (short 3B11).

EXAMPLE 4

Isolation of plasmid pCG3B11 and restriction analysis thereof

Large plasmid preparations (Ref 39) are made of the clone 3B11, obtained as described in Example 3.4. The corresponding plasmid, named pCG3B11, is analysed by complete restriction digestion with HindIII, EcoRI and PstI (all Boehringer, Mannheim) and electrophoretic separation over a 1% agarose gel (Restriction map see FIG. 1).

EXAMPLE 5

Subcloning of the EcoRI fragments of pCG3B11 containing the N-terminal and the C-terminal fractions of the pectin lyase I gene

EXAMPLE 5.1

Isolation of Sau3AI fragments of pG C3B11 and ligation into M13DNA

1 $\mu$g of plasmid pGC3B11 (Example 4) is digested to completion with 18 units of restriction endonuclease Sau3AI (Boehringer, Mannheim) in 20 $\mu$l 10 mmol/l Tris-HCl, 75 mmol/l NaCl, 10 mmol/l $MgCl_2$, pH 7.2 for 1 hour at 37° C. The reaction is terminated by addition of EDTA to a final concentration of 20 mM. The DNA fragments are extracted with phenol/chloroform precipitated by ethanol and resolved in 20 $\mu$l TE buffer. 100 ng of the Sau3AI digested DNA is ligated to 20 ng of M13mp8 phage DNA (Ref 40) linearized by BamHI digestion (Boehringer, Mannheim). The ligation is carried out for 4 hrs, at 15° C. with 1 unit of T4 DNA ligase (Boehringer, Mannheim) in a total volume of 10 $\mu$l ligation buffer. Competent *E. coli* JM101 cells are made in 50 mM $CaCl_2$ in accordance to the Amersham handbook (Ref 41) p. 25. 0.3 ml aliquots of the competent JM101 cells are transferred to 15 ml sterile culture tubes on ice. 5 μl of ligated phage DNA are added to each tube. The mixtures are kept on ice for 40 min. The cells are heat shocked to 42° C. for 3 min and the tubes returned to the ice bath. For each tube the following mixtures are prepared: 40 μl IPTG 100 mM, 40 μl X-gal 2% in dimethylformamide and 200 μl *E. coli* JM101 cells from a fresh exponentially growing culture. 270 μl of this mixture are added to each tube containing heat shocked *E. coli* JM101 cells. 3 ml of molten top agar (kept at 42° C.) are added to each tube and the tubes are poured onto agar plates. The plates are incubated inverted at 37° C. overnight.

EXAMPLE 5.2

Screening of recombinant phages with the oligonucleotide probe 2060

*E. coli* JM101 transformed with the recombinant phage DNA show white plaques on the X-gal containing agar plates of Example 5.1., 384 of which are picked and grown individually at 37° C. in 1.5 ml 2×TY medium inoculated with 15 μl exponentially growing *E. coli* JM101 cells. After 6 hrs the 384 cultures are centrifuged for 5 min in an Eppendorf centrifuge and the phage supernatants stored at 4° C. 100 μl from each of the 384 supernatants are transferred to four Gene Screen membranes (New England Nuclear) by using a BioDot apparatus with 96 slots (BioRad). The membranes are soaked 5 min in 0.5M NaOH, 1.5M NaCl and 5 min in 3M NaCl, 1M Tris-HCl, pH 5.6, dried in air and baked in vacuo at 80° C. for 2 hrs. Finally the four membranes are prehybridized, hybridized with the oligonucleotide mixture 2060 radioactively labelled as described above, washed and autoradiographed as described in Example 3.4. From the ligation experiment of Example 5.1. one positive, recombinant phage is chosen for further analysis, designated as mp8-3A.

EXAMPLE 5.3

Sequence analysis of recombinant mp8-3A phage

The supernatant containing phage mp8-3A obtained as described in Example 5.2., is used to prepare single-stranded and replicative form DNA (RF-DNA) as described in the Amersham handbook (Ref. 41) at p. 18–27. The single-stranded templates are sequenced using the chain terminator method described in the Amersham handbook at p. 30–35. The phage proves to contain the 574 bp Sau3AI fragment with the predicted nucleotide sequence of oligonucleotide probe 2060 at position 584 to 599.

EXAMPLE 5.4

Identification of the N-terminal and the C-terminal EcoRI fragments of pectin lyase I gene The sequenced EcoRI restriction site of phage mp8-3A (Example 5.3.), is used to identify and subclone two EcoRI fragments, one containing the C-terminal part of PLI gene, comprising the terminator region, and one containing the N-terminal part of the gene comprising the promotor region. The following two oligonucleotides are synthesized as described in Example 3.2.

Oligonucleotide 5052 corresponds to the complementary strand of the sequence which starts at position 1289, 5′ to the central EcoRI-site at position 1341, and extends to position 1269 of the sequence with SEQ ID No. 1.

Oligonucleotide 5066: corresponds to the sequence which starts at position 1711, 3′ to the central EcoRI-site, and extends to position 1730 of the sequence with SEQ ID No. 1.

The oligonucleotides 5052 and 5066 are radioactive labelled as described in Example 3.3.

1 μg of plasmid pCG3B11 (Example 11) DNA is digested to completion with EcoRI (Boehringer, Mannheim) and the fragments separated on a 1% agarose gel. The DNA fragments are blotted to Gene Screen membrane (New England Nuclear) as described by the supplier p. 383–386 and the membranes hybridized with radioactively labelled probes of oligonucleotides 5052 and 5066 as described by Maniatis et al. (Ref. 5) p. 387–389. Probe 5066 hybridizes with a 3.5 kb EcoRI fragment which contains the C-terminal part and the terminator region of the PLI gene. Probe 5052 hybridizes with a 2.9 kb EcoRI fragment containing the N-terminus and the promoter region of the gene.

EXAMPLE 5.5

Construction of pPL29-5 and pPL35-5 by recloning of EcoRI fragments of pCG3B11 into pUN121

4.5 μg of plasmid pCG3B11 DNA obtained as described in Example 4 are incubated with 50 units EcoRI (Boehringer, Mannheim) in 50 μl 0.01M Tris-HCl pH 7.5, 0.1M NaCl, 0.01M $MgCl_2$, 1 mM mercaptoethanol for 2 hrs at 37° C. The DNA fragments are separated on a 1% agarose gel, the gel slice containing the 2.9 kb fragment and the 3.5 kb fragment are eluted as described in Example 5 and the DNA extracted with phenol/chloroform and precipitated by ethanol. The precipitates are resuspended in 40 μl low TE buffer and 10 μl of this solution are ligated to 100 ng pUN121 (Ref 36) linearized by EcoRI digestion. The ligation is carried out at 15° C. for 4 hrs with 5 units T4 DNA ligase (Boehringer, Mannheim) in 35.5 μl 20 mmol Tris-HCl, 1 mmol EDTA, dithioerythritol 5 mmol, 60 mmol KCl, 50% glycerol, pH 7.6.

17.5 μl aliquots of this annealing mixture are added separately to 200 μl of competent *E. coli* HB101 cells, which have been prepared for transformation by treatment with calcium chloride as described by Maniatis et al. (Ref 5), p. 250. The mixtures are kept on ice for 30 min and heated to 42° C. for 2 min, then diluted with 1 ml of SOC-medium and incubated at 37° C. for 1 h. The cells are collected by centrifugation at 2000 g for 5 min. Each cell pellet is resuspended in 600 μl of SOC-medium and spread on three agar plate containing LB-medium supplemented with 8 mg/l tetracyclin. The plates are incubated at 37° C. for 16 h.

Figure 2:
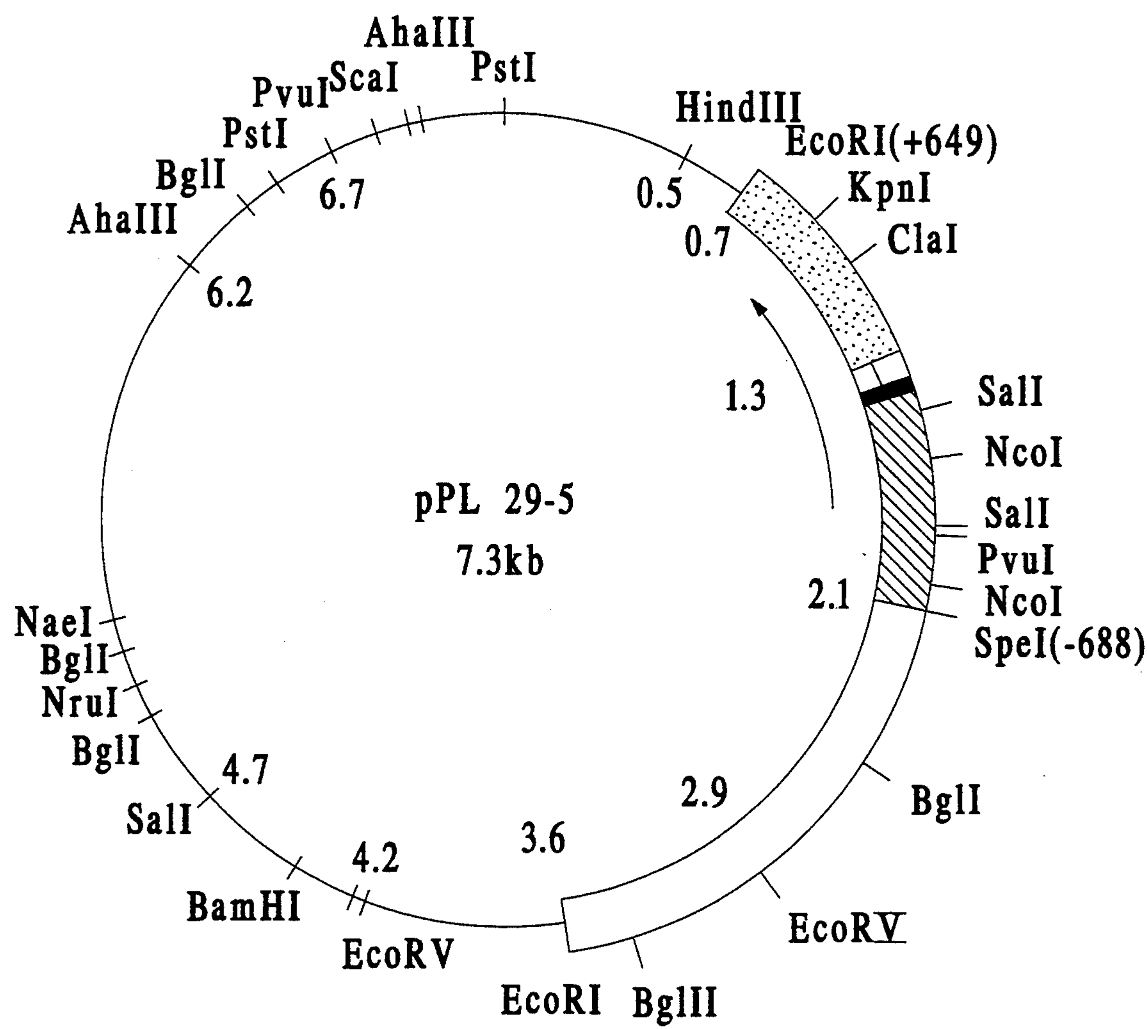
FIG. 2 shows the restriction map of plasmid pPL29-5 containing the N-terminal EcoRI fragment of the DNA of formula I
Figure 3:
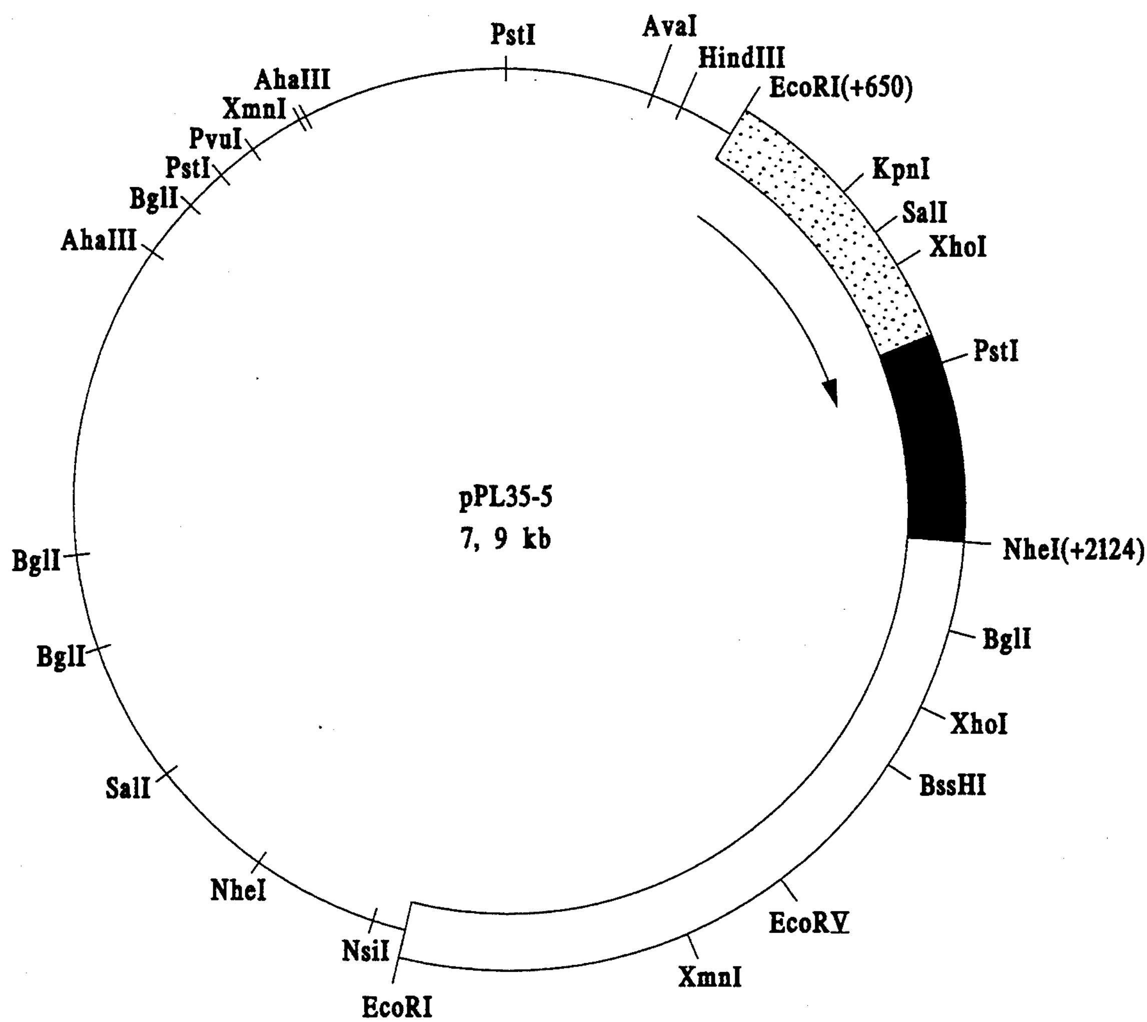
FIG. 3 shows the restriction map of plasmid pPL35-5 containing the C-terminal EcoRI fragment of the DNA of formula I FIG. 4 Shows the construction of pUBE5 from M13mp8-PL(SalI-EcoRI)BssHII/BE5 and pUN121. pUBE5 contains part of the PLI promoter, the signal sequence with BssHII restriction site, and part of the PLI structural gene

The plasmids of 6 recombinant $tet^R$ clones are isolated from each transformation by the method of Birnboim & Doly (Ref 23) and analysed by restriction analysis. One clone containing the 2.9 kb EcoRI fragment of pCG3B11 is chosen for further analysis and named pPL29-5 (FIG. 2). Another clone containing the 3.5 kB EcoRI fragment of pCG3B11 is chosen and named pPL35-5 (FIG. 3).

EXAMPLE 6

Sequence determination of the pectin lyase I gene

The DNA of pPL29-5 (Example 5.5.) containing the N-terminal part of the PLI gene and the DNA of pPL35-5 (Example 5.5.) containing the C-terminal part of the PLI gene are isolated as described by Humphreys et al. (Ref 39). Parts of the inserts of plasmids pPL29-5 and pPL35-5 are obtained by restriction with suitable enzymes. The fragments are subcloned into M13mp8 and M13mp18 and sequenced using the M13 Cloning and Sequencing Kit (M15 Sequencing Kit N.4502, Amersham) under the conditions given by the supplier (Ref 41).

The entire sequence of the 2.7 kb SpeI-NheI fragment, comprising the complete sequence of PLI gene, is shown under SEQ ID NO. 1 in the sequence listing. It comprises 688 nucleotides of the promoter region, 1369 residues of the structural part of the PLI gene and 660 nucleotides of the terminator region.

The sequence of PLI, corresponding to amino acid sequence of the N-terminus of PLI as determined by amino acid sequence analysis (Example 1), is preceded by 57 nucleotides coding for a signal sequence.

Figure 4:
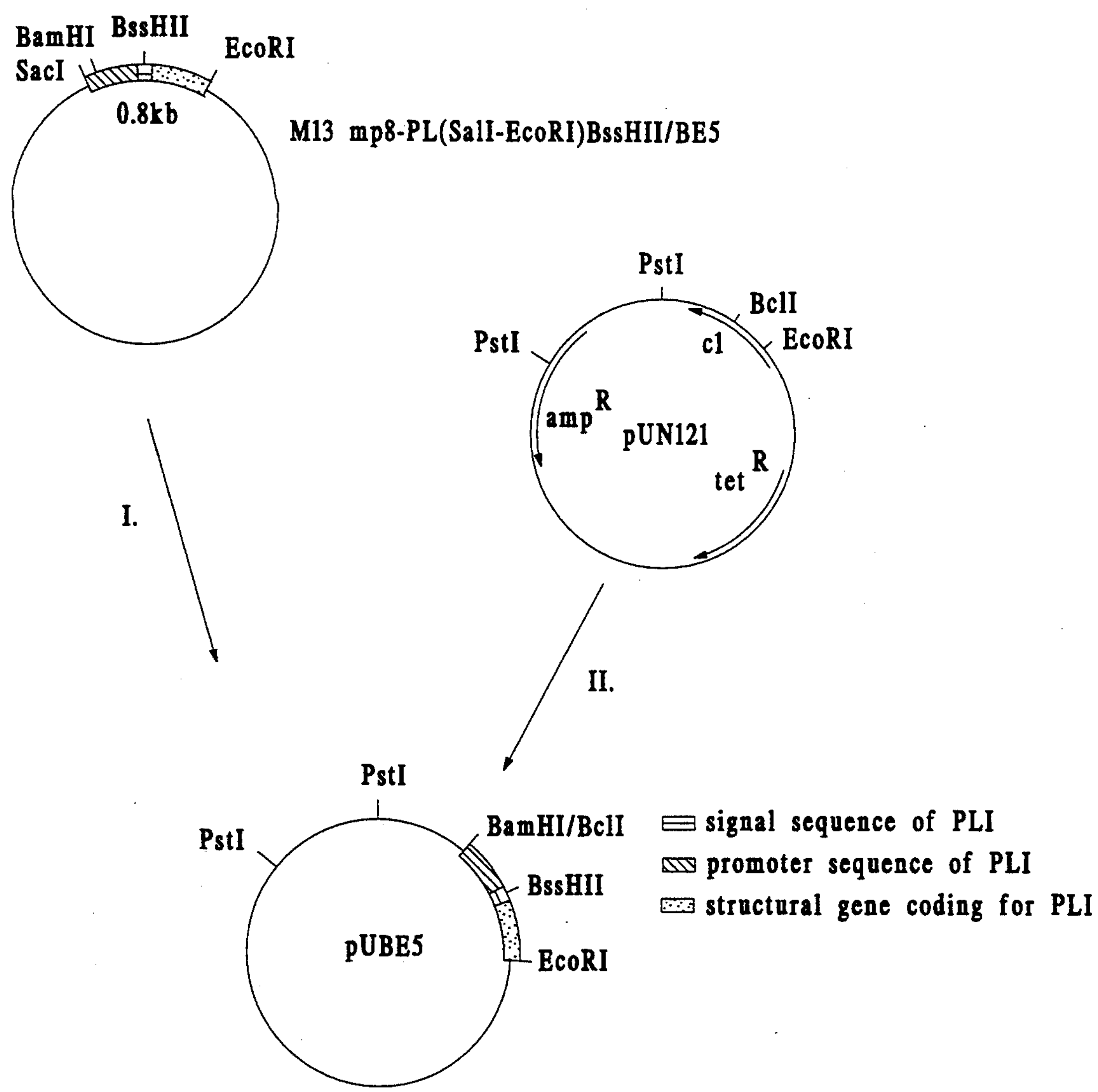

A computer aided search for consensus sequences of exon/intron splice junctions as well as for intron internal sequences (Boel E. et al. (Ref 24) and Mount S. M. (Ref 25)) leads up to postulate the presence of four introns with length of 65 bp, 62 bp, 63 bp and 57 bp respectively (FIG. 4, underlined).

The sequence of the PLI gene is determined by combination of the sequences of the EcoRI-SpeI fragment of plasmid pPL29-5 and the EcoRI-NheI fragment of pPL35-5 (both determined by subcloning in M13).

EXAMPLE 7

Construction of expression vectors

EXAMPLE 7.1

Introduction of a new restriction site in the signal sequence of the PLI gene The introduction of a new BssHII site in the signal sequence region of the PLI gene (sequenced in Example 6) by in vitro mutagenesis is done according to Zoller and Smith (Ref 42). An oligonucleotide consisting of 19 residues is synthesized by the method described in Example 3.2. which is complementary to the DNA sequence (pos. 725–743) coding for the C-terminal part of the PLI signal sequence, with the exception of nucleotide 734 leading to a C/G transversion because in the mutagenic primer the C in position 10 is replaced by G.

For the in vitro mutagenesis 200 pmols of oligonucleotide 5156 is 5' phosphorylated with 20 nmols rATP. The reaction is carried out for 1 h at 37° C. with 10 units T4 Polynucleotide kinase (Boehringer, Mannheim) in 20 μl kinase buffer. The reaction is terminated by heating to 65° C. for 10 min.

EXAMPLE 7.2

In vitro mutagenesis of template M13mp8-PL (Sal-EcoRI) DNA

The first in vitro mutagenesis experiment concerns single stranded DNA from phage M13mp8-PL (SalI-EcoRI), obtained in Example 6, which contains the 0.8 kB SalI-EcoRI fragment of plasmid pPL29-5, containing 117 nucleotides of the promotor and the N-terminal part of the PLI gene. 1 pmol single-stranded M13mp8-PL(SalI-EcoRI) DNA is mixed with 20 pmoles mutagenic primer 5156 (Example 7.1.) and 10 pmoles universal M13 sequencing primer (N.4511, Amersham) in 10.5 μl 0.02M Tris-HCl pH 7.5, 0.01M $MgCl_2$, 0.05M NaCl, 0.001M DDT. The mixture is quickly heated to 56° C. and slowly cooled to room temperature. 1 μl 0.2M Tris HCl pH 7.5, 0.1M $MgCl_2$, 0.01M DDT, 4 μl 2 mM dNTP, 1 μl 10 mM ATP are added to the mixture, 3 units of T4 DNA ligase (Boehringer, Mannheim) and 2 units of DNA polymerase I (Klenow fragment, Amersham) are added and the polymerization reaction is carried out for 15 hrs at 15° C. Three dilutions of the polymerization mixture are made (1:20, 1:100 and 1:500) in low TE buffer. From each dilution 1 μl and 5 μl are added to 300 μl competent *E. coli* JM101 cells separately, which have been prepared for transformation by the method described in Example 5.1. The cells are poured on X-gal plates and colonies forming white plaques are obtained. 100 of the white plaques are toothpicked and transferred to LB plates. The bacteria transformed with phage DNA are grown overnight at 37° C. and are subsequently transferred to Whatman 541 filters as described in Example 3.1. The filters are washed (Example 3.1.), then prehybridized in 6×NET, 1×ss-Denhardt, 0.1% SDS for 30 min at 67° C. The hybridization is carried out at RT (Example 3.4) for 30 min with 15 pmoles radioactive labelled (Example 3.3.) oligonucleotide 5156 per filter in 6×SSC. After hybridisation the filters are washed for4×40 sec in 6×SSC at room temperature and after drying in air exposed 1 hr to Kodak XAR-5 films using an Ilford Screen. The filters are washed a second time for 5 min in 6×SSC at 72° C. (Tm of the mutagenic primer 5156 is 70° C.), dried and exposed over night to a Kodak XAR-5 film.

Colonies giving rise to positive signals after the second washing step are picked from the original LB plate, suspended in 1 ml LB medium and heated to 70° C. for 20 min. This bacteriophage solution is diluted 1:10, 1:1'000 and 1:100'000 and 10 μl of each dilution is used to transfect 300 μl of exponentially growing *E. coli* JM101 cells and poured on X-gal plates. 6 plaques of the 1:100000 dilution are toothpicked individually into 1.5 ml 2×TY containing 15 μl of exponentially growing *E. coli* JM101 cells and grown at 37° C. for 6 hrs. The cultures are centrifuged 5 min in an Eppendorf centrifuge, the supernatants stored at 4° C. (phage stock) and the cell pellets are used to do RF preparations according to the method of Birnboim & Doly (Ref 23). After restriction analysis with BssHII one mutant phage bearing a new BssHII site in the PLI SalI-EcoRI fragment is chosen for further experiments and designated as (M13mp18-PL(SalI-EcoRI)BssHII/BE5).

EXAMPLE 7.3

In-vitro mutagenesis of template M13mp18-PL(SpeI-EcoRI)

The second in-vitro mutagenesis experiment is carried out with single-stranded DNA from phage M13mp18-PL(SpeI-EcoRI), obtained in Example 6. This recombinant phage contains the 1.4 kb SpeI-EcoRI fragment of plasmid pPL29-5 and thus 688 nucleotides of the promoter plus the N-terminal part of the PLI gene. Mutagenesis of this template is carried out exactly as described in Example 7.2. One phage bearing the new BssHII site in the PLI SpeI-EcoRI insert is chosen for four experiments and named respectively M13mp18-PL(SpeI-EcoRI)BssHII/AC5.

EXAMPLE 7.4

The construction of plasmid pUBE5

For easier handling the BamHI-EcoRI fragment of phage M13mp8-PL (SalI-EcoRI)BssHII/BE5 obtained as described in Example 7.2, including 130 bp of the promoter region and the N-terminal part of the PLI gene including the newly introduced BssHII site in the signal sequence region, is subcloned into plasmid vector pUN121 (Ref 36) as illustrated in FIG. 4 and described in the following.

4 μg RF DNA of phage M13mp8-PL (SalI-EcoRI)BssHII/BE5 is isolated according to Example 5.3. and is digested to completion with restriction endonucleases BamHI and EcoRI (Boehringer, Mannheim). The fragments are separated on a 1% agarose gel and the gel slice containing the 0.8 kb BamHI-EcoRI fragment, consisting of 117 bp of the promoter and the N-terminal part of the PLI gene is electroeluted as described in Example 2.2. The DNA is extracted with phenol/chloroform and precipitated with ethanol. The DNA pellet is resuspended in 10 μl water (50 ng/μl). 2 μg of pUN121 are digested to completion with BclI and EcoRI (Boehringer, Mannheim). The fragments are separated on a 1% agarose gel and the 4.0 kb fragment is electroeluted as described in Example 2.2. After phenol/chloroform extraction and ethanol precipitation the DNA is dissolved in 18 μl water (100 ng/μl).

300 ng of the BamHI-EcoRI fragment, comprising the BssHII site, are ligated to 500 ng of BclI/EcoRI cut pUN121DNA. The ligation is carried out for 4 hrs at 15° C. with 400 units T4 DNA ligase (Biolabs) in 20 μl of 50 mM Tris-HCl(pH 7,8) 10 mM $MgCl_2$, 20 mM dithiothreitol, 1.0 mM ATP. 10 μl of the ligation mix are used to transform 100 μl competent *E. coli* HB 101 cells (Ref 5). The cells are plated on LB plates containing 8 mg/l tetracycline (SIGMA) and incubated overnight at 37° C.

Plasmid preparations are made from 12 $tet^R$ colonies according to the method of Birnboim & Doly (Ref 23) and one plasmid with the desired restriction pattern shown in FIG. 4 is named pUBE5 and used for further analysis.

EXAMPLE 7.5

Figure 5:
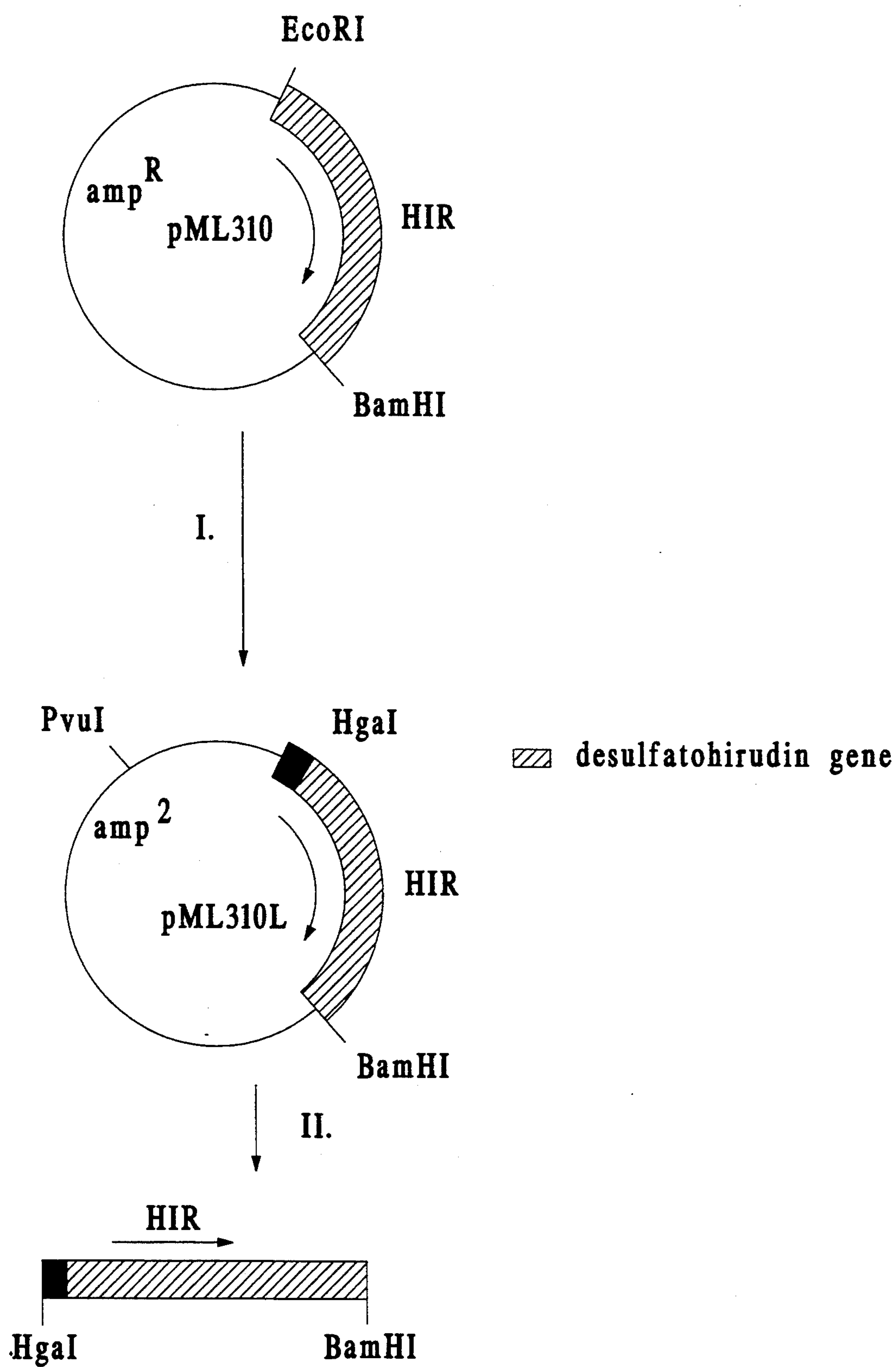
FIG. 5 shows the construction of pML310L containing the desulfatohirudin gene

Introduction of a HgaI restriction site in front of the desulfatohirudin gene of pML310 and the isolation of the 0.22 kB HgaI-BamHI gene fragment For the introduction of a HgaI restriction site in front of the desulfatohirudin gene (FIG. 5) 8 μg of plasmid pML310 DNA are digested to completion with restriction endonuclease EcoRI. The cleaved DNA is extracted with phenol/chloroform and precipitated with ethanol. To remove 5' overhanging ends, 4 μg of pML310/EcoRI DNA are digested in 100 μl of 150 mM NaCl, 1 mM $ZnSO_4$, 30 mM sodium acetate pH 4.6 and 20 U/ml of nuclease $S_1$ (Sigma) for 45 min at 37° C.

The DNA is extracted with phenol/chloroform and precipitated by ethanol. The DNA (pML310/EcoRI/$S_1$) is resuspended in 100 μl of 50 mM Tris-HCl pH 8.0 and incubated with 2 units of alkaline phosphatase from calf intestine (CIAP, orthophosphoric-monoesterphosphorylase, EC 3.1.3.1, Boehringer) for one hour at 37° C. The enzyme is inactivated at 65° C. for 1.5 hours. The NaCl concentration is adjusted to 150 mM. The dephosphorylated DNA (pML310/EcoRI/$S_1$/CIAP) is purified by adsorption to a DE52 (Whatman) ionexchange column in a low salt buffer (150 mM NaCl, 10 mM Tris.HCl pH 8.0, 1 mM EDTA). Elution is done with a high salt buffer solution (1.5M NaCl, 10 mM Tris.HCl pH 8.0, 1 mM EDTA). The DNA is precipitated with ethanol and resuspended in $H_2O$ at a concentration of 0.8 mg/ml.

For the introduction of an HgaI site the oligonucleotide depicted under SEQ ID No. 8 is synthesized by the phosphotriester method (Ref 43). The sequence of the oligonucleotide is self-complementary containing the recognition site for restriction endonuclease HgaI. Annealing of two single strands leads to a double-stranded DNA linker.

1.2 Hg of the synthetic single-stranded oligodeoxynucleotide are phosphorylated in 10 Hl of 60 mM Tris.HCl pH 7.5, 10 mM $MgCl_2$, 5 mM DTT, 30 μCi of [$\gamma$-$^{32}$P] ATP (3000 Ci.mmol$^{-1}$, Amersham) and 6 units of T4 polynucleotide kinase (Boehringer) for 30 min at 37° C., followed by a 15 min chase at 37° C. in the presence of 0.5 mM ATP. The mixture is further incubated for 10 min at 75° C. to inactivate the enzyme. The mixture is cooled to room temperature for annealing.

0.6 μg (170 pmoles) of the $^{32}$P-labelled linker DNA are mixed with 2.4 μg (1.75 pmol ends) of pML310/EcoRI/$S_1$/CIAP and ligated in 20 HI of 60 mM Tris.HCl pH 7.5, 10 mM $MgCl_2$, 5 mM DTT, 3.5 mM ATP, 800 units of T4 DNA ligase (Biolabs) for 20 hrs at 15° C. The ligase is inactivated at 85° C. for 10 min and the excess of linker molecules is removed by precipitation of the DNA in the presence of 10 mM EDTA pH 7.5, 300 mM sodium acetate pH 6.0 and 0.54 volumes of isopropanol. After 30 min at room temperature the DNA is pelleted resuspended in 45 H1 of ligation mixture (specified above) and ligated for 6 hrs at 15° C. to form circular DNA.

Aliquots of 1 μl and 3 μl of the ligation mixture are added to 100 μl of calcium-treated, transformation competent *E. coli* HB101 cells (prepared according to the method of D. Hanahan (Ref 37)). The cells are left on ice for 30 min, then incubated for 3 min at 42° C., cooled on ice for 2 min and then incubated for one hour at 37° C. in 400 μl of SOC medium. The cells are concentrated in 100 μl of SOC medium each plated on LB agar plates containing 50 μg/ml of ampicillin and are grown overnight at 37° C.

12 transformed $amp^R$ colonies are isolated and grown individually in LB medium containing 100 μg/ml of ampicillin. Plasmid DNA is prepared according to the method of D. S. Holmes et al. (Ref. 44). The presence of the synthetic oligonucleotide linker is confirmed by DNA sequencing using a single stranded DNA fragment as primer which hybridizes to the coding strand of hirudin. One clone which contains the linker DNA at the correct position in front of the hirudin gene is referred to as pML310L.

For the isolation of the 0.22 kb HgaI-BamHI desulfatohirudin gene fragment, 40 μg of plasmid pML310L are digested to completion with restriction endonucleases PvuI and BamHI (Boehringer) in 150 μl 0.01M Tris.HCl pH 7,5, 0.1M NaCl, 0.01M $MgCl_2$, 1 mM 2-mercaptoethanol for 2 hrs at 37° C. The fragments are separated on a 1% agarose gel and the gel slice containing the 0.84 kb PvuI-BamHI fragment is electroeluted as described in Example 5. After phenol/chloroform extraction and ethanol precipitation the DNA is resuspended in 20 μl HgaI-buffer and digested to completion with restriction endonuclease HgaI (Biolabs). The fragments are separated on a 2% agarose gel and the gel slice containing the 0.22 kb HgaI- BamHI fragment is eluted as before. After phenol/chloroform extraction and ethanol precipitation the fragment is resuspended in 55 μl sterile water (0.1 pmol/μl).

EXAMPLE 7.6

Fusion of the PLI signal sequence and the desulfatohirudin structural gene

To provide a linker in order to ligate the BssHII site of the signal sequence (Example 7.2.) coding region of the PLI gene and the HgaI site of the desulfatohirudin gene (Example 7.5), the two oligonucleotides 5172 and 5173 depicted under SEQ ID No. 13 and 15, respectively, are synthesized as described in Example 3.2.

300 pmoles of each oligonucleotide are kinased separately with 400 pmoles rATP and 10 units T4 polynucleotide kinase (New England Nuclear) in 15 μl of 50 mM Tris-HCl (pH 7.8), 10 mM $MgCl_2$, 20 mM dithiothreitol 1.0 mM ATP, 50 μg/ml BSA. Both kinased oligonucleotides are mixed in a 1:1 ratio, heated to 95° C. and are slowly cooled down to room temperature for annealing. The annealed linkers are stored at −20° C.

EXAMPLE 7.7

The construction of pLHK3

For the construction of a desulfatohirudin expression vector (FIG. 7) comprising the diminished promotor of PLI, 7 μg of pUBE5 DNA (Example 7.4.) are digested to completion with restriction endonuclease BssHII (Boehringer), extracted by phenol/chloroform and precipitated by ethanol. The DNA (1.9 pmol) is resuspended in 10 μl sterile water. 300 pmoles of annealed linker 5172/5173 (Example 7.6.)are ligated to 1.9 pmoles of BssHII-cut pUBE5 with 400 units T4 DNA ligase (Biolabs) in 60 μl of 50 mM Tris-HCl (pH 7.8), 10 mM $MgCl_2$, 20 mM dithiothreitol 1.0 mM ATP, 50 μg/ml BSA. The ligation is carried out for 15 hrs at 15° C. The ligase is inactivated by heating to 85° C. for 10 min. The buffer is adjusted to 0.01M Tris.HCl pH 8.0, 0,1M NaCl, 0.005M $MgCl_2$, 1 mM 2-mercaptoethanol. 36 units of BamHI (Boehringer) are added and digestion carried out for 2 hrs at 37° C. The fragments are separated on a 1% agarose gel and the 3.4 kB BamHI-[BssHII]HgaI-linker fragment isolated by electroelution of the gel slice followed by phenol/chloroform extraction and ethanol precipitation. The DNA is resuspended in 14 μl sterile water to a concentration of 0.1 pmol/μl. 0.2 pmols of the 0.22 kb desulphatohirudin HgaI-BamHI fragment are ligated to 0.1 pmol of the digested pUBE5 DNA. Ligation is carried out for 15 hrs at 15° C. with 400 units T4 DNA ligase (Biolabs) in 10 μl of 50 mM Tris-HCl (pH 7.8), 10 mM $MgCl_2$, 20 mM dithiothreitol, 1.0 mM ATP, 50 μg/ml BSA.

2 μl of the ligation mix are used to transform 100 μl of competent *E. coli* HB101 cells (Ref. 5), which are subsequently plated on LB dishes containing 50 mg/l ampicilline (SIGMA). The DNA of 12 $amp^R$ colonies is prepared by the method of Birnboim & Doly (Ref. 23) and analysed by restriction analysis. 1 clone is chosen for sequence analysis by the dideoxy chain terminator method of Sanger et al. (Ref. 45). A clone showing the desired restriction pattern and the correct sequence within the PLI-signal sequence-desulfatohirudin junction is isolated and named pLHK3.

EXAMPLE 7.8

The construction of pLHL5

For the construction of the desulfatohirudin expression vector, comprising the complete promoter sequence of PLI gene, 10.3 μg RF DNA of phage M13mp18-PL(SpeI-EcoRI)BssHII/AC5 (Example 3.3.) are digested to completion with restriction endonuclease BssHII (Boehringer), extracted by phenol/chloroform, precipitated by ethanol and resuspended in 10 μl sterile water to a concentration of 1.9 pmoles. 300 pmoles of annealed linker 5172/5176 (see above) are ligated to 1.9 pmoles of the BssHII-cut phage DNA as described in Example 7.7. After inactivation of the T4 DNA ligase the buffer is adjusted to 0.01M Tris-HCl, pH 7.6, 0.05M NaCl, 0.01M $MgCl_2$, 0,014M DTT. 36 units of restriction endonuclease HindIII (Boehringer) are added and digestion carried out for 2 hrs at 37° C. The fragments are separated on a 1% agarose gel and the 1.4 kb HindIII-[BssHII]HgaI-linker fragment is isolated by electroelution as described in Example 2.2. The fragment is resuspended in 15 μl sterile water leading to a concentration of 0.1 pmol/μl.

3 μg of plasmid pBR322 (Ref. 46) are digested to completion with restriction endonucleases BamHI and HindIII (Boehringer, Mannheim) in 20 μl 0.01M Tris.HCL pH 7.5, 0.1M NaCl, 0.01M $MgCl_2$, 1 mM 2-mercaptoethanol and the fragments are separated on a 1% agarose gel. The large 4.15 kb HindIII-BamHI fragment is eluted as described in Example 2.2. and resuspended in 8 B1 sterile water (0.1 pmol/μl).

Figure 7:
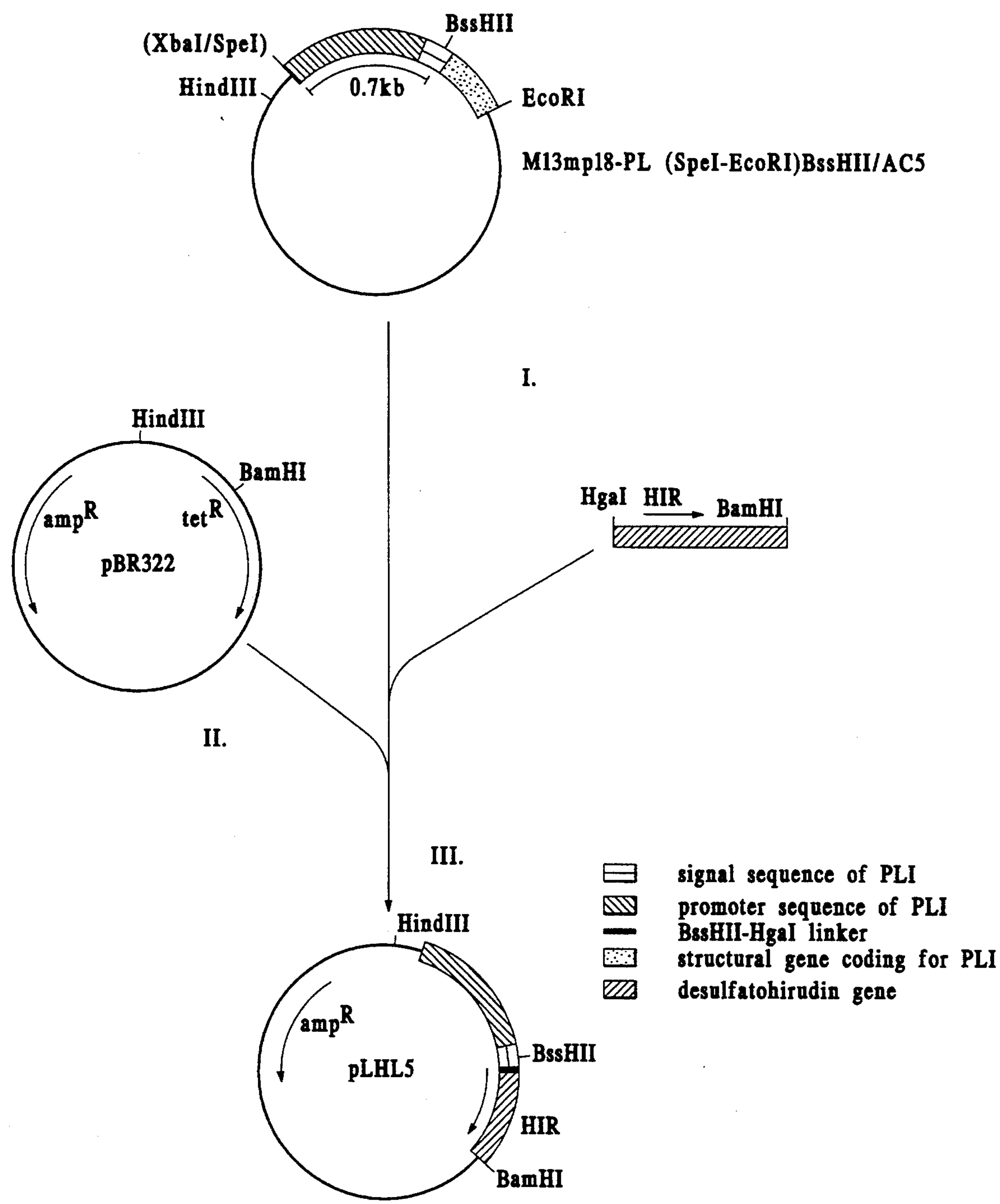
FIG. 7 shows the construction of pLHL5 containing the PLI promoter, the signal sequence with the BssHII restriction site and the desulfatohirudin gene

0.2 pmoles of the 0.2 kb HgaI-BamHI fragment of desulphatohirudin and 0.2 pmoles of the 1.4 kb PLI promoter-signal sequence HindIII-[BssHII]HgaI-linker fragment are ligated to 0.1 pmol of HindIII/BamHI-cut pBR322 for 15 hrs at 15° C. The ligation is carried out with 400 units T4 DNA ligase (Biolabs) in 10 B1 of 50 mM Tris-HCl (pH 7.8), 10 mM $MgCl_2$, 20 mM dithiothreitol, 1.0 mM ATP, 50 μg/ml BSA. 1 μl of the ligation mix is used to transform 100 μl competent *E. coli* HB101 cells (Ref. 5). 12 $amp^R$ colonies are isolated and the DNA analyzed as described in Example 7.7. One clone is chosen for further experiments and named pLHL5 (FIG. 7).

EXAMPLE 7.9

The construction of pLHLT7

Figure 8:
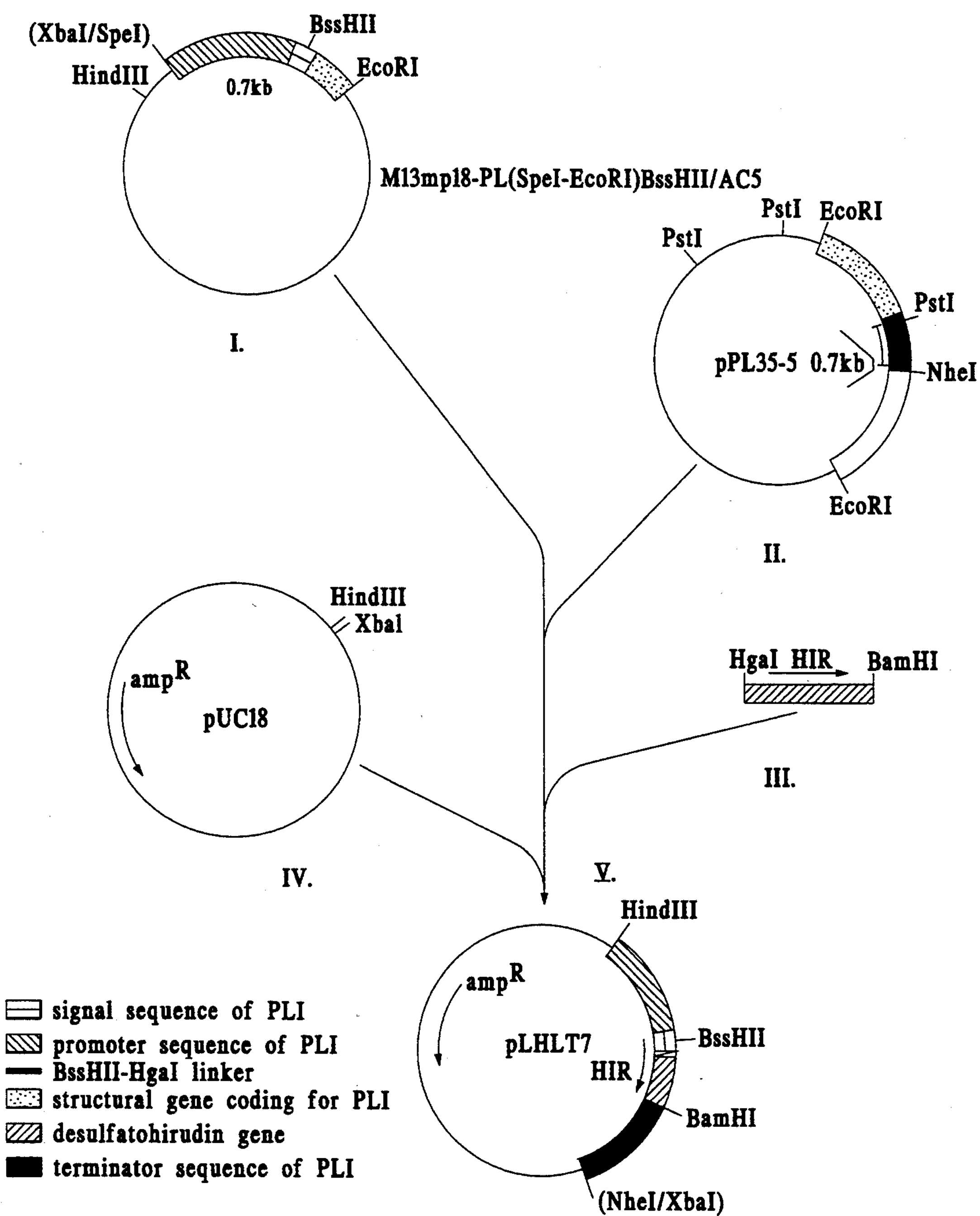
FIG. 8 shows the construction of pLHLT7 containing the PLI promoter, the signal sequence with the BssHII restriction site, the desulfatohirudin gene and the PLI terminator.
Figure 9:
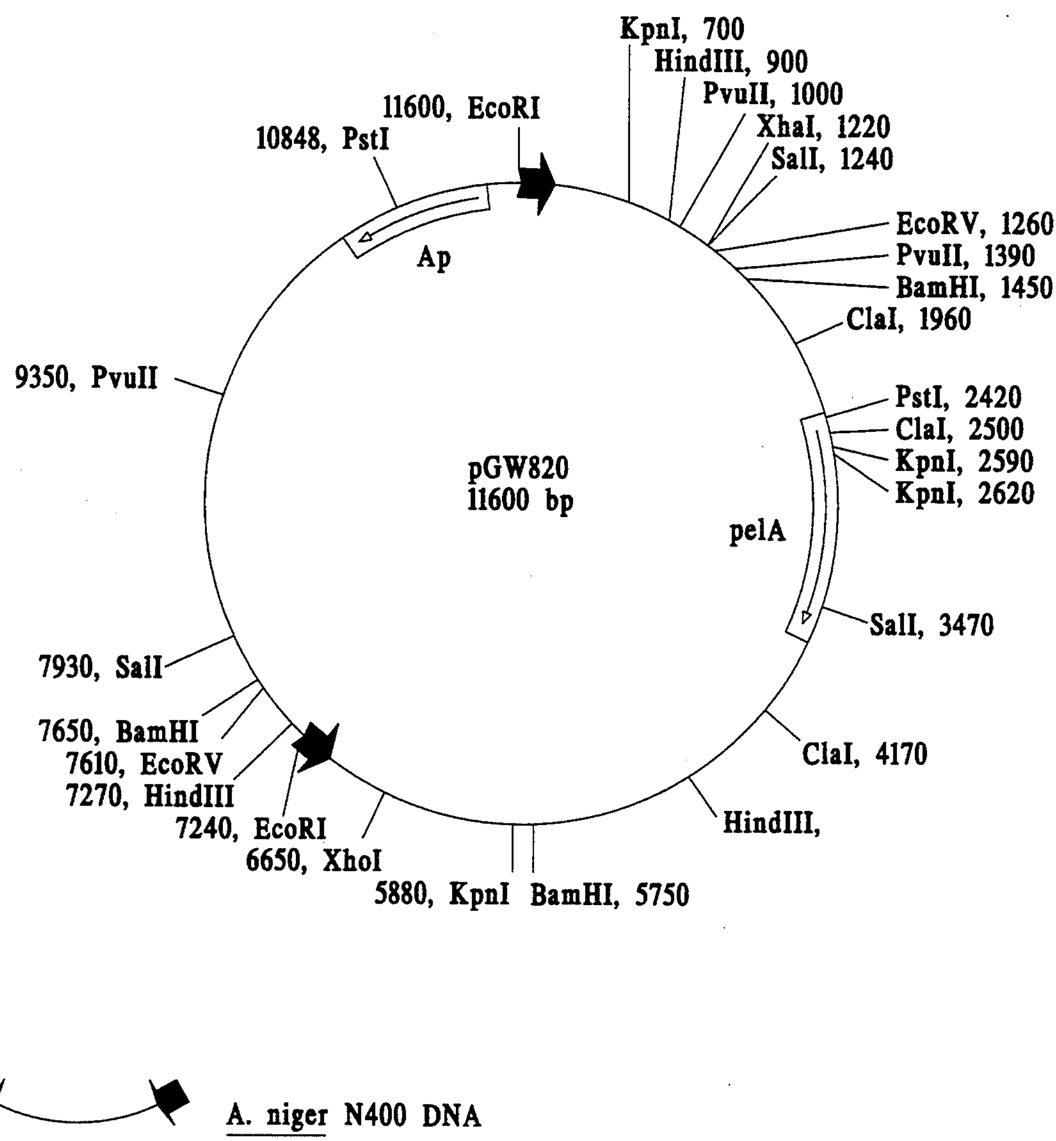
FIG. 9 shows the restriction map of pGW820 containing the pelA gene
Figure 10:
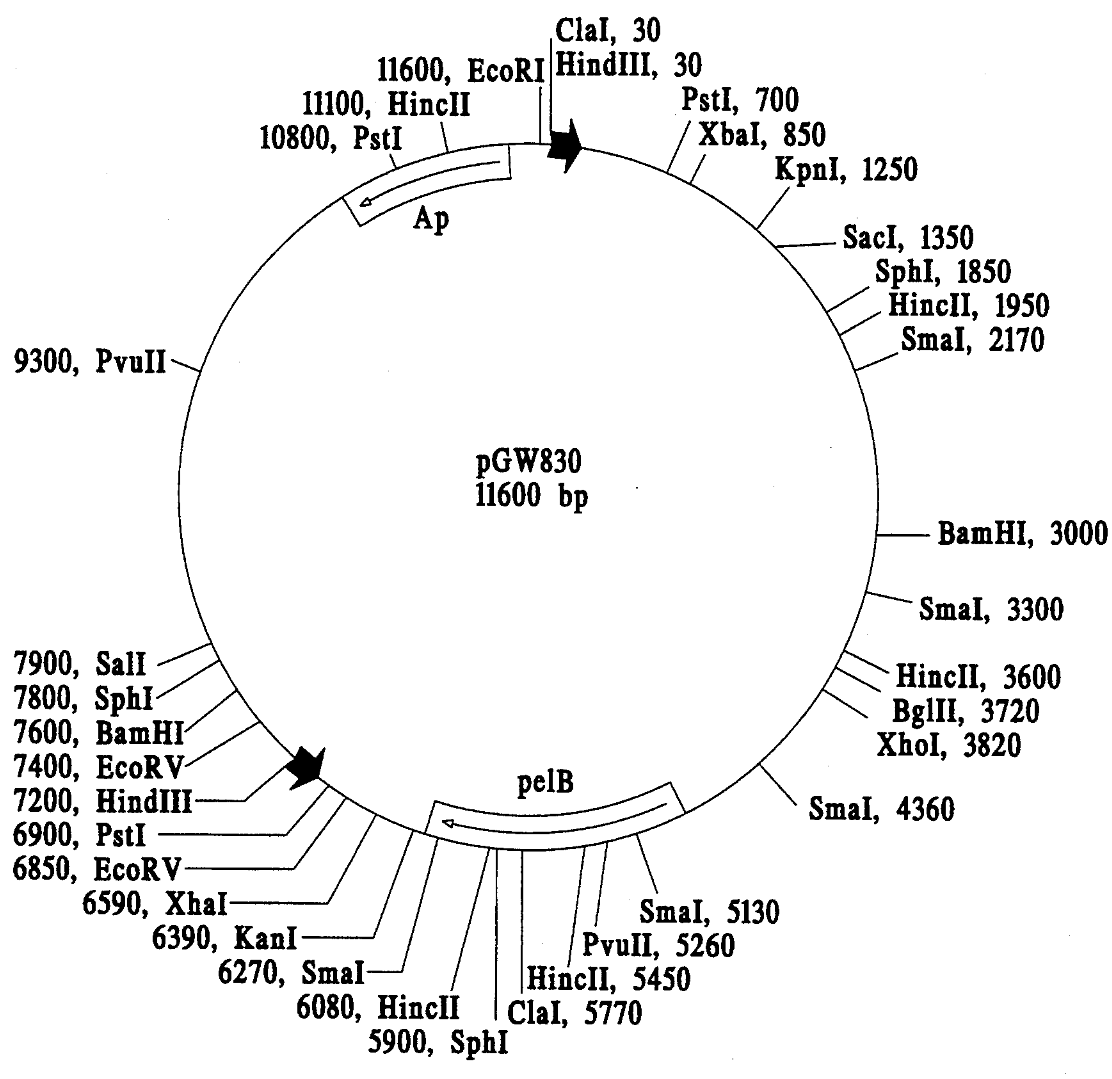
FIG. 10 shows the restriction map of pGW830 containing the pelB gene
Figure 11:
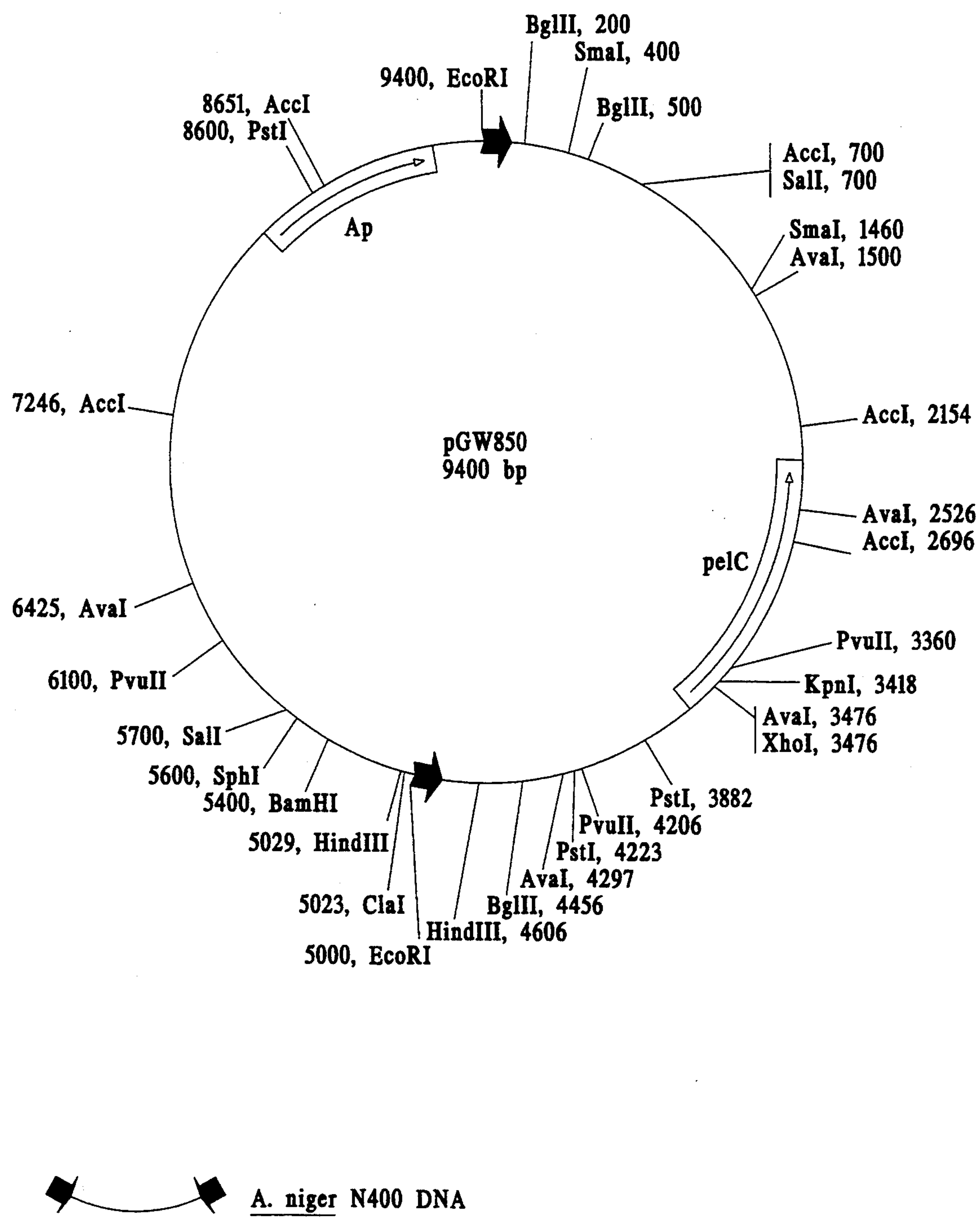
FIG. 11 shows the restriction map of pGW850 containing the pelC gene
Figure 12:
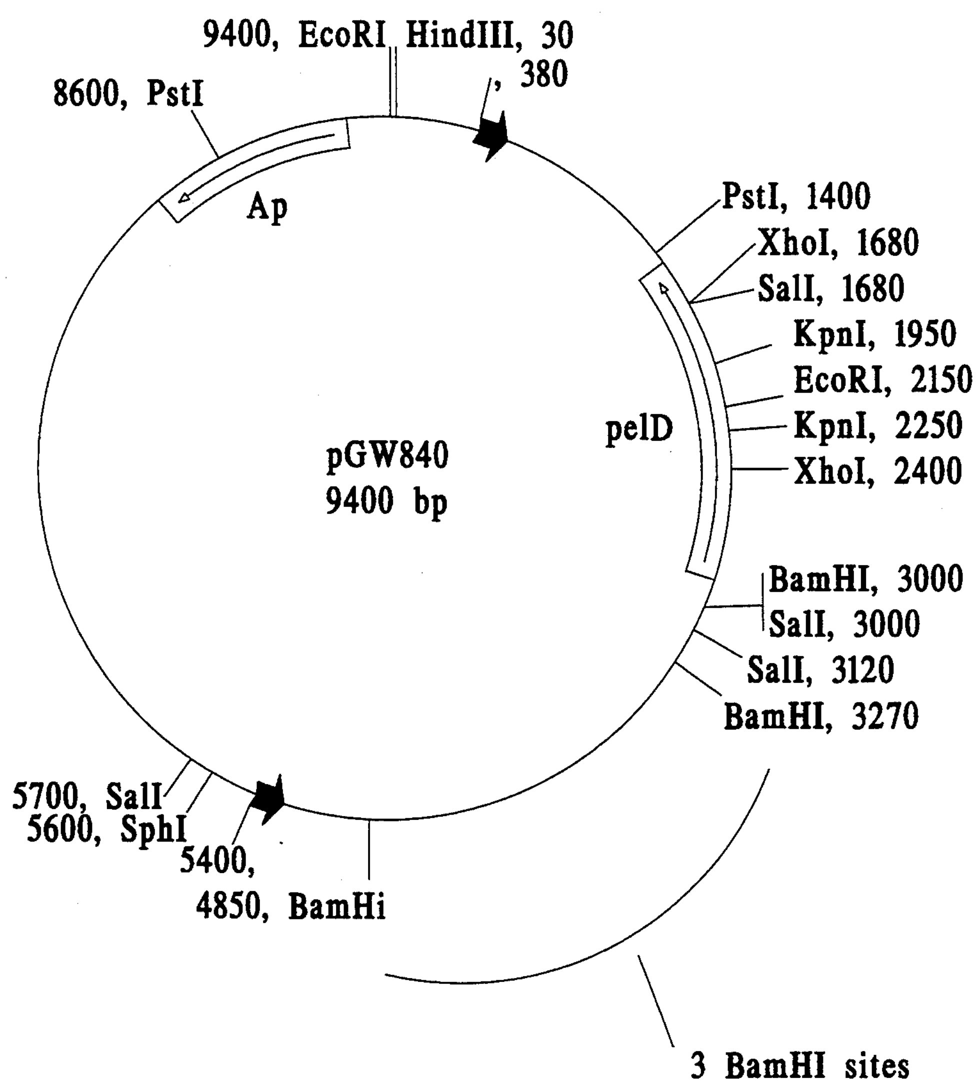
FIG. 12 shows the restriction map of pGW840 containing the pelD gene
Figure 13:
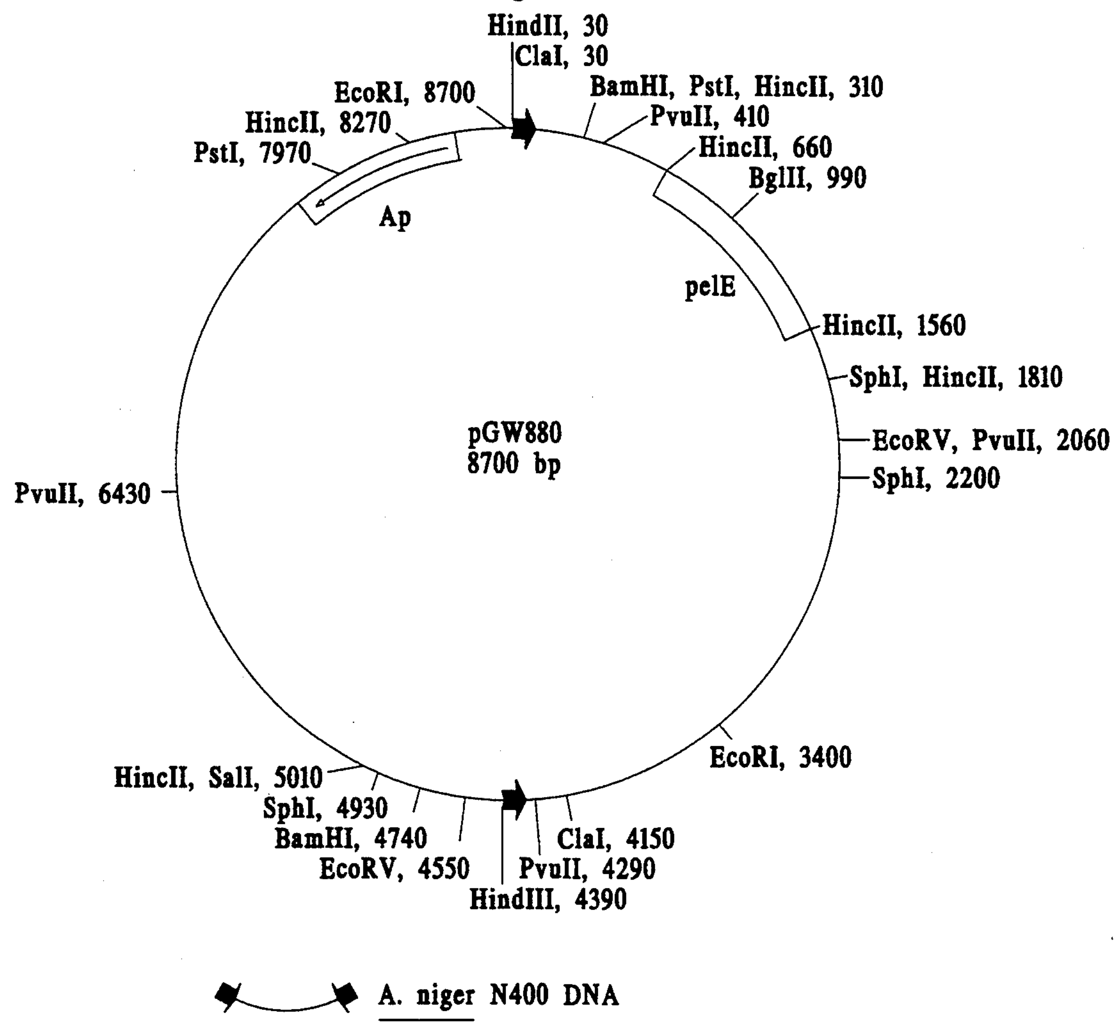
FIG. 13 shows the restriction map of pGW880 containing the pelE gene

To provide a terminator region to the PLI-desulfatohirudin expression system, the 0.7 kb PstI-NheI fragment of plasmid pPL35-5 is fused 3' to the desulphatohirudin gene as illustrated in FIG. 8.

10 μg of pPL35-5 are digested to completion with PstI (Boehringer). The DNA is phenol/chloroform extracted and precipitated by ethanol. The fragments are resuspended in 0.033M tris-acetate pH 7.9, 0.066M potassium-acetate, 0.01M magnesium-acetate, 0.5 mM DTT and 100 ng/ml BSA. 10 units T4 DNA polymerase (Boehringer) are added and the reaction carried out for 180 seconds at 37° C. The reaction mix is put on ice, 20 nmoles of dATP, dCTP, dGTP, dTTP each are added, the buffer adjusted to the above conditions and the reaction carried on for 35 min at 37° C. After phenol/chloroform extraction and ethanol precipitation the DNA is resuspended in 10 μl sterile water (1.9 pmoles =11.4 pmoles blunt ends). 900 pmoles of kinased and annealed (Example 7.6.) BamHI-linkers (Biolabs) are added and the ligation is carried out for 15 hrs at 15° C. with 400 units T4 DNA ligase (Biolabs) in 60 μl 50 mM Tris-HCl (pH 7.8), 10 mM $MgCl_2$, 20 mM dithiothreitol 1.0 mM ATP, 50 μg/ml BSA. After inactivation of the ligase by heating to 85° C. for 10 min, the buffer is adjusted to 0.01M Tris-HCl pH 8.0, 0.1M NaCl, 5 mM $MgCl_2$, 1 mM 2-mercaptoethanol. 20 units restriction endonuclease NheI (Biolabs) are added and digestion is done for 2 hrs at 37° C. The fragments are separated on a 1.2% agarose gel and the 0.7 kb NheI-[PstI]BamHI fragment is isolated by electroelution as described in Example 2.2. The fragment is resuspended in 15 μl sterile water to give a concentration of 0.1 pmol/μl.

A ligation is set up with 0.2 pmoles 0.7 kb NheI-[PstI]BamHI terminator fragment, 0.2 pmoles 1.4 kb HindIII-[BssHII]HgaI promoter fragment (Example 7.4.), 0.2 pmoles 0.2 kb HgaI-BamHI desulfatohirudin fragment (Example 7.5.) and 0.1 pmoles pUC18 vector (Ref. 47) linearized by HindIII and XbaI. The reaction is carried out with 400 units T4 DNA ligase (Biolabs) for 15 hrs at 15° C. in 10 μl of 50 mM Tris-HCl (pH 7.8), 10 mM $MgCl_2$, 20 mM dithiothreitol 1.0 mM ATP, 50 μg/ml BSA. 2 μl of the ligation are used to transform *E. coli* HB101 cells. 12 $amp^R$ transformants are analyzed as described in Example 7.6. and the plasmid showing the correct fusion sequences referred to as pLHLT7.

EXAMPLE 8

Construction of a cotransformation system for *A. niger*

EXAMPLE 8.1

Preparation of pCG59D7 containing the pyrA gene of *Aspergillus niger*

300 ng of a 1.1 kb HindIII fragment of pDJB2 (Ref. 26) bearing part of the *N. crassa* pyr4 gene are radioactively labelled by nicktranslation according to Maniatis et al., (Ref. 5). The filter replicas of the gene library (Example 3.1.) are wetted in 6×NET and prehybridized in 6×NET, 1×ss-Denhardt, 0.1% SDS for 4 hrs at 50° C. Nick-translated HindIII fragment is added (300 ng/80 filters) and hybridization carried out for 15 hrs at 50° C. After hybridization the filters are washed 1×for 5 min in 4×SSC, 0.1% SDS at 50° C. After drying in air the filters are exposed to KODAK X-Omat SO282 films for 3 days. One strongly hybridizing colony, named *Escherichia coli* BJ5183/pCG59D7 (short 59D7) is isolated and a large plasmid preparation made thereof (Ref. 39). The plasmid is referred to as pCG59D7 and is used for the transformation in Example 9.2.

EXAMPLE 8.2

Mutation of *A. niger* strain N 756 and isolation of mutants auxotrophic for uridine Selection for mutants of *A. niger* strain N 756 specifically lacking orotidine-5'-phosphate decarboxylase activity, can be achieved by positive selection against the toxic analogue fluoro-orotic acid (Ref. 13) in the presence of uridine. $3\times10^6$ conidial spores of *A. niger* strain N 756 are plated onto 10 ml of minimal medium plates supplemented with 1 g/l arginine and 50 mg/l uridine. The spores are submitted to short-wave UV-irradiation (2600 Å), at a dosage which results in 0.5% surviving colonies. After 2 days of incubation at 28° C., when the outgrowing mycelia is slightly visible, 10 mg of fluoro-orotic acid are added to each plate and incubation continued for another 2–3 days. Fluoro-orotic acid resistant colonies appear as heavily growing and sporulating colonies on a background growth of whitish sensitive mycelia. From about 40'000 survivors of mutagenic treatment 8 mutants are isolated. 2 of them which are resistant to fluoro-orotic acid without uridine requirement are not followed further. 6 of them have a uridine auxotrophy. Heterocaryons are made by growing a mixture of conidial spores of two fluoro-acid resistant mutants each on complete medium overnight. Blocks of mycelia are transferred to minimal medium. Mutants complementary to each other in their mutation show outgrowth of prototrophic heterocaryotic mycelia at the edges, strains with a mutation in the same allele do not. The 6 uridine-requiring mutants from strain N 756 fall, as in *S. cerevisiae* (Ref. 13), into 2 complementation groups. One of each—An 8 and An 10—is used for transformation.

EXAMPLE 8.3

Preparation of protoplasts and transformation of uridine-mutants An 8 and An 10 of *A. niger* N 756

Conidial spores of mutants An 8 and An 10 are grown separately on slants for 4–5 days at 28° C. in complete medium. $2\times10^8$ conidiospores of An 8 and An 10 are used to inoculate separately 200 ml minimal medium supplemented with 1 g/l arginine and uridine (Example 8.2). After 20 hrs growth at 28° C. and 180 rpm. the mycelium is harvested by filtration through Miracloth, washed twice with 10 ml 0.8M KCl 50 mM $CaCl_2$ and resuspended in 20 μl 0.8M KCl, 50 mM $CaCl_2$, 0.5 mg/ml Novozym 234 (Novo Industries). The mixture is incubated in a shaking waterbath (30° C., 50 rpm.) until maximum protoplast release can be detected microscopically (90–120 min). The protoplast suspension is filtrated through a glass wool plug in a funnel to remove mycelial debris. The protoplasts are pelleted by mild centrifugation (10 min, 2000 r.p.m) at room temperature and washed twice with 10 ml 0.8M KCl 50 mM $CaCl_2$. The protoplasts are finally resuspended in 200–500 μl 0.8M KCl, 50 mM $CaCl_2$ to give a concentration of $1\times10^8$/ml.

For transformation 200 μl aliquots of protoplast suspensions (An 8 and An 10) are incubated separately together with solutions consisting of 10 μg/20 μl pCG59D7 DNA, 50 μl PCT, (10 mM Tris-HCl pH 7.5, 50 mM $CaCl_2$, 25% PEG 6000). The incubation mixtures are kept on ice for 20 min, another 2.0 ml of PCT are added and the mixtures incubated for further 5 min at room temperature. 4 ml 0.8M KCl, 50 mM $CaCl_2$ are added and 1 ml aliquots of these final transformation solutions are mixed with liquefied minimal agar medium (MM+1 g/l arginine+10 g/l Bacto-Agar (Difco)) stabilized with 0.8M KCl. The mixtures are immediately poured on agar plates of the same medium and incubated at 28° C.

After 3 days of growth at 28° C., stable transformants appear as vigorously growing and sporulating colonies on a background growth of many hundred small presumably abortive transformants.

Transformation with pCG59D7 is only successful in mutant An 8, not in An 10. An 8 is therefore considered to lack the ornithine-5'-phospate decarboxylase activity, which is complemented by the full-length gene-product of selection plasmid pCG59D7. In An 8 about 20–30 transformants are obtained per μg pCG59D7.

Ten transformants of An 8 are picked, subcultured on minimal medium and the DNA is isolated and analysed for the presence of pCG59D7 sequences. DNA of the transformants is isolated after powdering of the frozen mycelia in liquid nitrogen according to a published procedure (Ref. 1). 1 μg DNA of each transformant is digested to completion with Xho I, fractionated by electrophoresis over 1% agarose gels and blotted to nitrocellulose filters according to Maniatis (Ref. 5), p. 382–386. The blots are hybridized with [α-$^{32}$p]-labelled pUN 121DNA following standard procedures as described by Maniatis et al. (Ref. 5), p. 387-389. The various hybridization patterns obtained indicate chromosomal integration of the transforming plasmid pCG59D7 at various locations into the host genome.

EXAMPLE 9

Expression of the desulfato-hirudin gene under the control of PLI promoter in *A. niger*

EXAMPLE 9.1

Cotransformation of mutant An 8 with pCG59D7, pLHK3, pLHL5 or pLHLT7

Protoplasts of mutant An 8 are prepared according to Example 8.2 and are cotransformed with 5 μg of selection plasmid pCG59D7 and either 10 μg of plasmid pLHK3 (Example 7.7.), 10 μg of plasmid pLHL5 (Example 7.8.) or 10 μg of plasmid pLHLT7 (Example 7.9.), following the procedure as described in Example 8.2.

Transformed An 8 cells are selected on minimal medium for uridine prototrophy as described in Example 8.2.50 transformants of each cotransformation experiment are randomly picked and analysed for desulfato-hirudin expression. Desulfato-hirudin activity is tested in a thrombin inhibition assay acording to the chromogenic peptide substrate manufacturer's instructions (Boehringer, Mannheim, FRG).

EXAMPLE 9.2

Expression of desulfato-hirudin under control of the PLI promoter in transformants of mutant An 8

Conidial spores from transformants obtained according to Example 8.3. are individually precultured into 50 ml of a preculture medium (Pectin Slow Set L (Unipectin, SA, Redon, France) 3 g/l, $NH_4Cl$ 2 g/l, $KH_2PO_4$ 0.5 g/l, NaCl 0.5 g/l, $Mg_2SO_4 \times 7H_2O$ 0.5 g/l, $Ca_2SO_4 \times 2H_2O$ 0.5 g/l, pH 7.0). The preculture is incubated for 72 hrs at 250 rpm and 28° C. 10% of the preculture is used to inoculate 50 ml of main culture medium (Soybean flour 20 g/l, pectin Slow Set 5 g/l). The culture is grown up for 72–96 h (highest rate of pectin lyase production) at 250 rpm and 28° C. (referred to as inducing conditions). Transformants of mutant An 8 are also grown under non-inducing conditions in Phytone peptone 10 g/l, glucose 10 g/l instead of main culture medium.

At various times (every 20 hrs) samples are taken, the cells are pelleted by centrifugation and broken by ultrasonic desintegration. Supernatant and cell extracts are both tested for desulfato-hirudin activity as described in Example 9.1. No desulfato-hirudin activity is detected following cotransformation with plasmid pLHK3. pLHL5 and pLHL7 containing the full-length PLI promoter are both able to drive expression of desulfato-hirudin in *A. niger* mutant An 8. Of the 50 transformants taken from the cotransformation experiments (Example 9.1.) 10 each show desulfato-hirudin activity in the medium.

Expression of desulfatohirudin in mutant An 8 under control of the full-length PLI promoter and making use of the PLI signal peptide is therefore regulated by the inducing substrate pectin and leads to secretion of desulfatohirudin into the medium.

EXAMPLE 10

Construction of a genomic library of *Aspergillus niger*

EXAMPLE 10.1

Isolation of high molecular weight DNA from *A. niger* N400

Conidiospores of *Aspergillus niger* strain N400 are inoculated in 200 ml minimal medium in a final spore density of 106 spores/ml and shaken in 1 l Erlenmeyers for 24 hrs at 28° C. at 300 rpm using a New Brunswick rotary shaker. The mycelium is harvested by filtration using a Büchner funnel with Myracloth, washed with cold sterile saline, frozen in liquid nitrogen and either stored at −60° C. or used directly. The method used for isolation of DNA to prepare the genomic library is based on the procedure described by Yelton et al. (ref. 1). The DNA yield is about 50–100 μg/g mycelium with this method.

For library construction, 10 g mycelium is ground in liquid nitrogen in 1 g portions in a Braun micro-dismembrator. The ground mycelium is transferred to a 1 l sterile erlenmeyer, containing 200 ml extraction buffer (50 mM EDTA pH 8.5, 0.2% SDS) and 200 μl diethylpyrocarbonate. The mixture is slowly heated to room temperature and then heated for 20 min to 68° C. while occasionally shaking. The suspension is cooled to room temperature and centrifuged for 15 min. at 12,000×g 1/16 volume of an 8M potassium acetate solution pH 4.2 is added to the supernatant and the mixture is left on ice for 1 hr. The precipitate is removed by centrifugation (20 min.; 16,000×g; 4° C.). The nucleic acids are precipitated from the supernatant by an incubation with 0.6 volume of isopropanol on ice for 15 min. The pellet is collected by centrifugation (10 min.; 6,000×g; 4° C.), washed with 70% ethanol and briefly dried. The pellet is suspended in 10 ml TE containing 20 μg/ml RNase A, (Boehringer, Mannheim) and incubated for 15 min. at 37° C. The DNA is treated with nuclease free pronase (1 mg/ml final concentration) (Kochlight, Coinbrook) for 1 hr at 37° C. The pronase stock solution in TE buffer contains 20 mg/ml of enzyme which is incubated for 1 hr at 37° C. to digest nucleases.

8.5 g CsCl is dissolved in 9 ml DNA solution, 0.2 ml 10 mg/ml ethidiumbromide is added and this solution is either centrifuged in a Beckman SW41 rotor for 60 hrs at 33,000 rpm, or in a Beckman 50Ti rotor with quickseal tubes for 40 hrs at 45,000 rpm. The DNA band is collected by side-puncturing of the tube. Ethidiumbromide is removed by multiple extraction with water—and NaCl saturated isopropanol. 5 volumes of TE are added, the DNA is extracted with TE saturated phenol, phenol/chloroform/isoamylalcohol 25:24:1 and chloroform/isoamylalcohol 24:1. The DNA is precipitated by addition of 0.1 volume of 3M sodium acetate pH 5.2, 2.5 volumes of ethanol and an overnight incubation at −20° C. The precipitate is collected by centrifugation (1 hr; 30,000×g; 4° C.), washed with 70% ethanol, dried and dissolved in 400 μl low TE.

EXAMPLE 10.2

Partial digestion of *A. niger* N400 DNA with MboI and isolation of fragments To test for the MboI concentration which gives the largest amount of fragments between 13.6 and 23 kbp, 1 μg portions of *A. niger* N400 DNA are digested in the appropriate buffer with decreasing amounts of MboI (0.5–0.001 U) for 1 hr at 37° C. in a volume of 10 μl. The reaction is stopped by addition of 1 μl 0.25M EDTA, and the samples are loaded on a 0.6% agarose gel in TBE, containing 1 μg/ml ethidiumbromide. Convenient markers are a mixture of lambda DNA and lambda DNA digested with BglII, which gives bands of 49, 22.8, 13.6, 9.8, 2.3, kbp and a nonvisible fragment of 0.45 kbp. The Mbo I concentration, required to give a high yield of the desired 13.6–23 kbp fragments is 0.02 U/μg DNA. Accordingly, 200 μg of DNA in a total volume of 2 ml are digested, and are divided into 20 portions of equal size immediately after addition of the enzyme. After 1 hr at 37° C. the digests are placed on ice and a 1 μg sample is run on a gel to test for proper digestion. As the result is positive, EDTA is added to a final concentration of 25 mM to stop the reaction, the enzyme is heat-inactivated at 65° C. for 10 min, samples are pooled and the DNA is precipitated, washed, dried and dissolved in 400 μl TE.

The fragmented DNA is separated overnight on a 0.4% preparative agarose gel (center well 120×1.5 mm). Lambda DNA digested with Bgl II is used as marker to determine the size of the partially digested DNA fragments upon electrophoresis at 4° C. and 40 V (3 V/cm). The gel region containing fragments of the correct size is cut out of the gel and the DNA is electroeluted from the gel in a sterile dialysis tubing in 2 ml TBE during 2–3 hrs at 100 V. The current is reversed for 30 s, and the buffer containing the DNA is collected. The fragments are then concentrated by ethanol precipitation and dissolved in 100 μl low TE.

EXAMPLE 10.3

Preparation of vector DNA and cloning of high molecular weight DNA fragments of *A. niger* N400 into EMBL 4

The genomic library of *A. niger* strain N400 is constructed into the lambda vector EMBL4. The vector, which has a cloning capacity of 9–23 kbp, is described by Frischauf et al. (ref. 2) and Karn et al. (ref. 3) and has been purchased from Promega Biotech. Inc. To avoid double inserts originating from different parts of the genome, we have used a minimal fragment length of 13.6 kbp for cloning.

10 μg lambda EMBL4 DNA is digested to completion with 50 units of BamHI in the appropriate buffer in a volume of 100 μl for 2 hrs at 37° C. The enzyme is inactivated for 10 min. at 65° C. The NaCl concentration is raised to 150 mM and 50 units of SalI are added and incubation at 37° C. proceeds for another 2 hrs. After addition of EDTA to 25 mM and inactivation of the enzyme (10 min. 65° C.) the solution is extracted with equal volumes of phenol (TE saturated), phenol/-chloroform/isoamylalcohol 25:24:1, chloroform-/isoamylalcohol. To eliminate the small BamHI/SalI polylinker fragments, the DNA is precipitated with 0.6 volume of isopropanol after the addition of 0.1 vol. 3M sodium acetate pH 5.2. After 15 min. on ice and 15 min. centrifugation at 12,000×g and 4° C., the precipitate is thoroughly washed with 70% ethanol, dried and dissolved in 40 μl low TE.

EXAMPLE 10.4

Ligation and in vitro packaging of genomic *A. niger* N400 DNA fragments

It is essential that the cos sites of the vector prepared according to example 10.3 are annealed prior to the ligation reaction. The vector in 100 mM Tris-HCl pH 7.5 and 10 mM $MgCl_2$ is heated for 10 min at 65° C. and then annealed for 1 hr at 42° C. From test ligations a ratio of vector to fragments of approximately 1:1 (by weight) is found to give a maximum of recombinants. Ligation takes place in 50 mM Tris HCl pH 7.5, 10 mM $MgCl_2$, 10 mM DTT and 1 mM ATP, using 9.5 μg of vector and 10 μg of DNA fragments in a total volume of 100 μl. Then DNA ligase (BRL) is added at a concentration of 0.5 U/μg DNA and the ligation mixture is incubated overnight at 14° C. To test for ligation a sample of the ligated DNA is run on an agarose gel. Also, an amount of 0.5 μg of vector is ligated without the addition of fragments in a 5 μl volume.

The large volume ligation mixture is concentrated by ethanol precipitation and dissolved in 20 μl low TE prior to in vitro packaging. In vitro packaging is done with Promega Packagene extracts according to the instructions of the manufacturer using 10 μl portions to package 1 μg of DNA. Of the high molecular weight lambda cI857 Sam 7, supplied with the extracts, 1 μg is separately packaged to provide a control. After packaging 500 μl of phage solution buffer (PSB) is added and 5 μl of chloroform. The recombinant phage stocks can be stored at 4° C. The library obtained has been constructed from two separate ligation experiments.

EXAMPLE 10.5

Titration and amplification of the *A. niger* strain N400 genomic library

Cells of *E. coli* NM539 are grown on LC medium containing 0.2% maltose, 10 mM MgSO4 and 1 mM $CaCl_2$ to an optical density (600 nm) of 1.0. Then aliquots of 0.2 ml of this culture are added to 0.1 ml of a phage dilution series in PSB. After adsorption of the phages for 20 min at 37° C., 3 ml 0.6% LC top-agar of 45° C. is added, the mixture is plated on LC agar plates and these are incubated overnight at 37° C. The titration results expressed as the number of plaque forming units (pfu) per ml phage suspension are $12\times10^5$ and $4.2\times10^5$ pfu/ml for the two phage stocks prepared according to example 1.4. After subtracting the background which is calculated from the control ligations without fragments (17% and 40% respectively) the absolute number of recombinants is $6\times10^5$ which is over 200 times genome length.

To amplify the library, portions of 80 μl of both phage stocks are used to infect *E. coli* NM539 cells which are plated in LC top-agarose on LC agar plates and then incubated overnight at 37° C. The phages are eluted from the agarose by gently shaking the plates with 5 ml PSB per plate for 1 hr at room temperature. The PSB is collected, centrifuged (10 min at 6000×g) to remove bacteria and chloroform is added (0.5% final concentration). Both phage stocks, which are approximately amplified to the same extent, are then mixed (40 ml stock), titrated ($8\times10^9$ pfu/ml) and stored at 4° C.

EXAMPLE 11

Screening the genomic library of *A. niger* N400 for the pectin lyase D gene (pelD) and isolation of the gene

EXAMPLE 11.1

Screening of the library

For the isolation of the pelD gene from the lambda genomic library obtained as described in Example 10, $2.5\times10^4$ phages are mixed with liquefied LC top-agarose and plated out on 5 LC agar plates. The plates are incubated overnight at 37° C. and chilled for 2 hrs at 4° C. From each plate 2 replicas are made according to the Benton and Davis (ref. 4) plaque hybridization method. The first filter (Schleicher and Schüll BA85 or Millipore HATF 085) is placed on top of the plate for 1 min, the second replica for 2 min and the position of the replicas is marked using India ink.

After removal of the filters they are placed in a dish containing 100 ml of a denaturing solution (1M NaCl, 0.5M NaOH) for 1 min, and for 1 min in 100 ml renaturing solution (0.5M Tris/HCL pH 7.5, 1.5M NaCl). Then the filters are transferred to a dish containing 3×SSC (SSC=0.15M NaCl, 0.015M sodiumcitrate pH 7.0). The filters are gently scrubbed with a gloved hand to remove bacterial debris, transferred to a fresh dish containing 3×SSC and gently shaken for 20 min at room temperature. The filters are blotted on Whatman 3 MM paper and dried for 10 min at room temperature. The filters are baked on 3 Whatman MM paper in an oven at 80° C. for 2 hrs. Subsequently they are washed for 0.5 hr in 6×SSC at room temperature and then transferred to 50 ml of the prewarmed (56° C.) prehybridization mixture which consists of 50 mM Tris/HCl pH 7.5, 10 mM EDTA, 1M NaCl, 0.5% SDS, 0.1% sodium pyrophosphate, 10×Denhardt's (50×Denhardt's=1% BSA, Boehringer fraction V; 1% polyvinylpyrrolidone −40; 1% Ficoll 400). To the prehybridization mixture one freshly adds: 0.1 mg/ml denatured salmon sperm DNA (Maniatis, et al. Ref. 5, p 327; ref. 5) and 0.01 mg/ml poly rA. Prehybridization is for 4 hrs at 56° C. with gentle shaking. The probe used for hybridization is the nick translated 3.5 kbp Eco RI fragment of pPL35-5, which contains the C-terminal region of the pelD gene of the *A. niger* N756 strain (available from *E. coli* BJ5183/pCG3B11, DSM 3916, EP 88 101 397.3). The fragment is previously isolated from a low melting agarose gel and 0.3 μg of the fragment is nick-translated (Maniatis, et al. Ref. 5, pp 109–112; ref. 5). The nick-translated DNA is denatured for 10 min in a boiling water bath, cooled on ice and added to 50 ml of prewarmed prehybridization mixture. The prehybridized filters are transferred to the hybridization mixture one by one. Hybridization is at 56° C. overnight while gently shaking. The filters are washed at 56° C.: 2×30 min with 0.5 14×SSC, 0.1% SDS, and 2×30 min. with 2×SSC, 0.1% SDS. The filters are blotted on 3 MM paper and dried by air for 1 hr. After sticking them to 3 MM paper and proper marking with radiolabeled ink, the filters are covered with Saran wrap and auto-radiographed overnight at −70° C. using Konica X-ray films and Kodak X-Omatic cassettes with regular intensifying screens. In this way, 44 positive signals are obtained from the 5 plates screened. Positive plaques are picked with a sterile Pasteur pipette by carefully positioning the plates on the autoradiogram in the right way using the ink markers. The pieces of agar containing the positive plaques are dispensed in 1 ml of PSB. The phages are allowed to diffuse from the agar during 1 hr at room temperature with occasional vortexing. The agar and bacterial cell debris are removed by centrifugation for 5 min, 10 μl chloroform is added and the phage stocks are stored at 4° C. The positive clones are named λ-PL1 to λ-PL44. Since phages are plated in high density, the positive plaques have to be purified twice by plating them at low density (±100 phages/plate; 0.1 ml of $10^3$ dilution of the phage stock) and repeating the whole procedure of replica plating, hybridization and picking of positive plaques.

EXAMPLE 11.2

Isolation of lambda DNA

To isolate DNA from the recombinant clones, phages are first amplified by infecting *E. coli* NM539 with 0.1 ml of phage stocks from purified clones as described in example 1.5, and plating the cells in LC top-agarose on LC agar plates. This gives plates with confluent lysis of the indicator bacteria. 5 ml PSB is spread over the plates and phages are eluted during 2 hr with gentle shaking. The eluted phages are harvested, cellular debris is removed by centrifugation and chloroform is added to 1%. The resulting plate lysate is stored at 4° C. It usually has a titer of about $10^{11}$ pfu/ml.

Since small scale isolation procedures from plate lysate stocks and from small scale liquid cultures (Maniatis et al., pp 65–68; ref. 5) do not always result in digestible DNA in our hands, phages are isolated from 250 ml lysates. These are prepared by growing the host, *E. coli* NM539, to an $O.D._{600}$ of 0.3 in LC+0.2% maltose 10 mM $MgSO_4$, 1 mM $CaCl_2$ and then adding approximately $10^{10}$ pfu of the plate lysate. Upon further growth, the bacteria lyse within 4 hrs.

RNase and DNase are added to the lysates to a final concentration of 2 μg/ml, and the lysate is left at room temperature for 1 hr. Cellular debris is removed by centrifugation (20 min., room temperature 10,000×g). 14.8 g NaCl and 25 g PEG6000 are dissolved in the supernatant to obtain the final concentrations of 1M NaCl and 25% (w/v) PEG. The phages are left to precipitate for 1 hr on ice or overnight at 4° C., and harvested by centrifugation (20 min.; 10,000×g; 4° C.). The pellets are suspended in 3 ml of lambda dilution buffer (LDB;=10 mM Tris/HCl pH 7.5, 20 mM $MgCl_2$, 100 mM NaCl). 2.5 g CsCl is dissolved in 4 ml of phage suspension and the mixture is pipetted in 5 ml Beckman quickseal tubes which are then filled up with the same concentration of CsCl in LDB. The tubes are sealed and centrifuged overnight in a Beckman VTi 65.2 rotor at 50,000 rpm and 4° C. The turbid phage band, visible under a normal lamp, is punctured from the side of the tube. CsCl is removed by dialysis in sterile tubing against 2 1 of 10 mM Tris/HCl pH 7.5, 10 mM $MgCl_2$, 50 mM NaCl at 4° C. for 4 hrs. The buffer is changed once. Phages are collected in sterile Greiner tubes, the volume is adjusted to 1 ml with the dialysis buffer, 50 μl of 10% SDS, 50 μl 0.5M EDTA pH 8.0 and 25 μl of 20 mg/ml nuclease free pronase are added and the tubes are incubated for 1 hr at 37° C. The volume is raised to 3 ml with TE, and this solution is extracted with equal volumes of TE saturated phenol, phenol/chloroform-/isoamylalcohol 25:24:1 and chloroform-/isoamylalcohol 24:1. After addition of 0.1 volume of 3M sodium acetate pH 5.2 and 2.5 volumes of ethanol, the DNA is precipitated overnight at −20° C. and collected by centrifugation (1 hr 20,000×g at 4° C.). The pellet is washed with 70% ethanol, dried, and dissolved in 200 μl low TE. The yield of phage DNA is about 200 μgs/250 ml lysate.

EXAMPLE 11.3

Restriction analysis of pelD clones

From the positive phages, 10 were at random selected for further analysis. 1 μg of phage DNA is digested with 10 units of EcoRI or BglII in a volume of 20 μl for 2 hrs at 37° C. in the buffers recommended by the supplier. The samples are separated on a 0.6% agarose gel using 1 μg lambda cI857 Sam 7 DNA digested with HindIII (lambda×HindIII) as markers and EMBL4 DNA and pCG3B11 DNA digested with EcoRI as controls. The gel is photographed on a UV transilluminator using Polaroid 667 films (4s, diafragma 8). The DNA is transferred to Schleicher and Schüll BA85 nitrocellulose filters according to the method of Southern (1975) as described by Maniatis pp 382–386; (ref. 5). The filters are hybridized with a mixture of $^{32}P$ labelled (nick-translated) fragments of the pelD gene covering the whole gene. These fragments are the 2.9 kbp EcoRI fragment of pPL29-5 and the 3.5 kbp EcoRI fragment of pPL35-5 (see example 5.5). Hybridization and washing conditions are identical to those described in example 11.1.

Band lengths are calculated from the photograph and autoradiograms by graphical comparison on semilogarithmic paper with the known marker bands. Clones λ-PL4, -14, and -40 contain both the 2.9 and 3.5 kbp EcoRI hybridizing fragments as found in pCG3B11. λ-PL5, -6, -10 and -33 contain the 3.5 kbp EcoRI fragment together with another hybridizing EcoRI fragment. Clones λ-PL26 and -28 contain the 2.9 kbp EcoRI fragment together with another hybridizing fragment, whereas λ-PL9 only contains a small 1.2 kbp hybridizing EcoRI fragment. The complete 5.0 kbp BglII fragment of pCG3B11, containing the whole structural pelD gene, is only present in clones λ-PL4, -14 and -40. The 3.7 kbp hybridizing band, present in clones λ-PL5, -6, -10, -14, -33 and -40, but not in pCG3B11, is located downstream of the pelD gene in the 5.0 kbp fragment. Some hybridizing BglII fragments still contain 1.2 kbp of the right arm of the vector. All the clones also contain nonhybridizing fragments that are identical. Since it therefore appears that the restriction patterns of both the structural gene and the gene environments are identical in all clones, it is concluded that they originate from the same gene viz the pelD gene of *A. niger* strain N400. From the number of clones plated and the assumed genome length of $3\times10^7$ bp, for 25,000 clones with an average insert length of 15 kbp at least 12 pelD clones are expected to be found. Since only 2 out of the 10 clones analyzed are identical, the complexity of the library is even higher, than supposed (cf. Example 12).

EXAMPLE 11.4

Subcloning of pelD fragments

The 5.0 kbp BglII fragments of λ-PL4 and pCG3B11 containing the pelD genes of *A. niger* N400 and N756 respectively, are subcloned into the BamHI site of plasmid pBR322.4 μg of λ-PL4 and 2 μg of pCG3B11 are digested to completion in 20 μl with 10 U of BglII for 2 hrs at 37° C. The fragments are separated on a 1% low melting point LMP agarose (BRL) gel in TBE+1 μg/ml ethidium bromide at 50 V. The 5.0 kbp fragment is cut out from the gel, diluted with 0.4 ml TE, an equal volume of phenol is added and the mixture is heated to 65° C. for 10 min to melt the agarose. After centrifugation for 5 min at 12000 rpm in an Eppendorf 5414S table centrifuge, the aqueous phase is extracted with phenol/chloroform and chloroform, ethanol precipitated, washed, dried and finally dissolved in 10 μl low TE.

1 μg pBR322 DNA, prepared by the large scale plasmid preparation method (Maniatis, et al. p 86; ref. 5) and purified by CsCl gradient centrifugation, is digested with 5 U BamHI for 2 hrs at 37° C. in a volume of 20 μl. 2 μl of 10×CIP buffer and 0.02 units of CIP are added and the incubation is continued for another 30 min. EDTA is added to a final concentration of 25 mM, and the mixture heated for 10 min. 65° C. The solution is diluted to 200 μl with TE and extracted three times with TE saturated phenol, once with phenol/chloroform and once with chloroform. After ethanol precipitation, the DNA is dissolved in 50 μl low TE.

100 ng of fragment DNA is ligated with 20 ng of vector DNA in a volume of 20 μl, under conditions described in example 10.4. Half of the ligation mixture is used to transform *E. coli* MH1 competent cells, prepared by the $CaCl_2$ method (Maniatis, et al. p 250; ref. 5). Cells are plated on LC agar plates containing 50 μg/ml ampicillin and incubated overnight 37° C. Transformants are tested for tetracycline sensitivity by streaking colonies first on LC plates containing 20 μg/ml Tc, and then on LC+amp plates. Transformants are grown overnight in 5 ml of LC+amp at 37° C., and DNA is isolated from 1.5 ml of the culture, using the alkaline lysis miniprep method (Maniatis, et al. p 368; ref. 5).

The miniprep DNAs are digested with BamHI and PstI and the fragments analyzed on a 1% agarose gel. Two plasmids originating from λ-PL4, containing the 5.0 kbp BglII fragment in opposite orientations, are designated pGW840 and pGW841. Further plasmids originating from pCG3B11 are designated pGW870 and pGW871. The MH1 cells harbouring them are kept on glycerol at −70° C. Plasmid DNA from 0.5 1 cultures of these clones is isolated on a large scale (Maniatis, et al. p 86; ref. 5), purified by CsCl centrifugation, phenolized, ethanol precipitated and dissolved in 400 μl low TE. The yield is approximately 500 μg. The plasmids are subjected to restriction mapping. The map for plasmid pGW840 is shown in FIG. 2 and is indistinguishable from pGW870. Also, plasmids pGW841 and pGW871 which contain the fragment in the opposite orientation are indistinguishable, indicating identity of the pelD genes from *A. niger* strain N400 and N756.

EXAMPLE 12

Screening for, isolation and characterization of genes related to pelD

EXAMPLE 12.1

Establishing hybridization conditions by analysis of genomic blots of *A. niger* N400 DNA 2 μg DNA samples of *A. niger* strain N400 , isolated as described in Example 1.1, are digested in a volume of 20 μl for 4 hrs at 37° C. using BamHI (BRL) or HindIII (BRL) in HHA B/g buffer. The digested samples are electrophoretically separated on 0.6% agarose gels at 40 V for 18 hrs. The DNA is transferred to nitrocellulose filters and baked as described in Example 11.3. (Pre)-hybridization solutions are identical to those described in Example 11.1.

The temperature used for prehybridization is always the same as the hybridization temperature. The nick translated 1.6 kbp BamHI/PstI fragment of pGW840 which contains the coding region of the pelD gene, has been used as a probe. Hybridization is carried out at different temperatures (52, 60 and 68° C.) for 16 hrs and 40 hrs. The following two washing conditions are used at the three different temperatures: 2×30 min 5×SSC, 0.1% SDS followed by 2×30 min 3×SSC, 0.1% SDS as compared to 4×30 min 5×SSC, 0.1% SDS. For 68° C. washing twice with 2×SSC, 0.1% SDS and twice with 0.2×SSC, 0.1% SDS is also included. At 68° C., using 0.2×SSC washings, only homologous hybridization occurs. Using higher salt concentrations gives rise to the appearance of some other weak signals. At 52° C. the background is high and hybridization weak. The best conditions found for "heterologous" hybridization are 60° C. for 40 hrs using the washing combination of 5×SSC and 3×SSC. This can even be further optimized by using 4×SSC in combination with 2×SSC instead of 5×SSC in combination with 3×SSC. The signals seen in these genomic blots of *A. niger* N400 when probed with the 1.6 kbp BamHI/PstI fragment of pGW840 are summarized in Table I.

TABLE I

Hybridization signals in genomic DNA of *A. niger* N400 probed with the 1.6 kb BamHI/PstI from pGW840.

| BamHI | HindIII |
|---|---|
| 7.5 kbp strongly homologous; pelD | 21.0 kpb strongly homologous; pelD |
| 4.3 kbp strong | 3.9 kbp strong |
| 4.1 kbp weak | 7.1 kbp weaker |
| 18.0 kbp weak | 4.4 kbp weak |
| 8.4 kbp very weak | 4.6 kbp weak |
| | 1.5 kbp very weak |

EXAMPLE 12.2

Screening of the library $2.5\times10^4$ phages from the N400 lambda library are plated on 5 plates and 3 nitrocellulose replicas are made from each plate, as described in Example 11.1. The (pre)hybridization buffer is also described in Example 11.1. The first replica from each plate is hybridized at 60° C. for 40 hrs with the 1.6 kbp BamHI/PstI fragment of pGW840 and washed twice at that temperature for 30 min with 4×SSC, 0.1% SDS and twice for 30 min with 2×SSC, 0.1% SDS as described in Example 12.1. These conditions are referred to as heterologous conditions. The second replica from each plate is hybridized at 68° C. with the same fragment washing twice for 30 min with 2×SSC, 0.1% SDS and twice for 30 min with 0.2×SSC, 0.1% SDS at this temperature. These conditions are referred to as homologous conditions. The third replica from each plate is hybridized homologously with the 0.35 kbp BamHI fragment of pGW840, which is located in the promoter region of pelD directly adjacent to the 1.6 kbp BamHI/PstI fragment. 29 plaques are obtained which hybridize heterologously but not (or very weakly) homologously. These are named λ-PL101 to λ-PL129. 19 plaques are obtained which hybridize strongly homologously and heterologously with the BamHI/PstI probe. These are designated λ-PL130 to λ-PL148 and are considered to be pelD clones. Of these, 2 hybridize only weakly with the 0.35 BamHI probe λ-PL145 and λ-PL146), and therefore probably contain only part of the promotor region. The others hybridize strongly. Only 1 clone is obtained which hybridizes only with the 0.35 kbp BamHI probe (λ-PL149).

All clones are picked and purified twice by plating and hybridizing them heterologously with the 1.6 kbp BamHI/PstI probe. In a second screening experiment 23 pelD clones and 25 other clones have additionally been obtained (λ-PL151 to λ-PL198).

EXAMPLE 12.3

Characterization of lambda clones by plaque hybridization signal with different probes derived from pelD In this experiment a classification of the isolated clones is described by using different parts of the coding region of pelD as probe. Included are λ-PL101 to -130, -145 whereas λ-PL4 is used as a positive control. The clones are plated out and only one replica is made which is divided into 6 parts. This is meant to rule out differences in hybridization signal between replicas. Separate parts of the replicas are hybridized both homologously and heterologously with the following $^{32}$p labelled probes:

1: the complete 1.6 kbp BamHI/PstI fragment from pGW840
2: the 649 bp BamHI/XhoI fragment from pGW840 (N)terminal coding part of pelD)
3: The 244 bp XhoI/PstI fragment from pGW840 (C-terminal coding part of pelD)

λ-PL4, -130 and -145, as well as λ-PL101 hybridize strongly with these probes under homologous and heterologous conditions, as is expected for pelD clones. The latter clone, λ-PL101, is located at the edge of a filter in Example 3.2 and therefore not scored as pelD in the first screening. The clones just mentioned are classified as Class I (pelD) clones. λ-PL112, -126 and -127 turn out to be negative in this experiment. All other clones can be divided into two other classes: Class II hybridizes heterologously not only with the whole probe but also with the N-terminal probe. Homologous hybridization is only weak with the whole pelD gene as a probe. Class III clones do not hybridize with the N-terminal probe at all, and also not homologously with the whole probe. The C-terminal probe fails to hybridize with both Class II and Class III clones. From these experiments we conclude that there are at least 2 related genes amongst the clones isolated.

To the Class II clones belong: λ-PL104, -105, -109, -113, -114, -115, -119, -122, -124, -125, -128 and -129.

The Class III clones are: λ-PL102, -103, -106, -107, -108, -110, -111, -116, -117, -118, -120, -121 and -123.

EXAMPLE 12.4

Restriction analysis of the isolated lambda clones (Class I, II)

Plate lysate stocks, 250 ml liquid lysates and large scale phage DNA preparations from these lysates are prepared as described in Example 11.2. This is done for 24 clones, 3 of them being pelD clones (λ-PL4, -130, -145). One clone DNA is lost during DNA isolation (λ-PL124). The DNA isolated from these clones is digested in 1 μg samples in a total of 20 μl with 10 units of enzyme. All clones are digested with EcoRI, BamHI, HindIII, EcoRI/Bam,HI, BamHI/HindIII, EcoRI/-HindIII and EcoRI/BamHI/HindIII. Fragments are separated on a 0.6% agarose gel, and transferred to nitrocellulose filters as described in Example 11.3. Blots are hybridized heterologously with the 1.6 kbp BamHI/PstI fragment of pGW840 as described in Example 12.1. Two clones fail to hybridize (λ-PL112 and λ-PL129). Band lengths from both the photographs and autoradiograms are calculated. Except for the λ-PL113 clone, all clones contain too many fragments to derive a complete map.

However, it is possible to derive a map of the hybridizing region and, by combining data on other non-hybridizing bands, to assign which clones are derived from the same gene. It is clear that among the remaining 18 Class II and III clones analyzed, 5 genes are present. These are called pelA, pelB, pelC, pelE and pelF. The assignment of clones to these genes is summarized in Table II.

TABLE II

Assignment of isolated clones to different pel genes (Part) means that the hybridizing band are only partially present in these clones

| Class | Gene | λ-Clones |
|---|---|---|
| I. | pelD | PL4, PL130, PL145 (part) |
| II. | pelA | PL113, PL104, PL115, PL125 (part) |
| | pelB | PL119, PL122, PL128, PL105 (part) |
| | pelC | PL109 |
| III. | pelE | PL116, PL107 (part) |
| | pelF | PL102, PL103, PL110, PL120 PL121 (part), PL123 (part) |

TABLE III

Comparison of hybridizing bands in chromosomal blots and isolated genes. The band length are in kbp.

| | EcoRI | BamHI | HindIII | |
|---|---|---|---|---|
| Chromosomal | 2.9 + 3.5 + larger bands | 7.5 | 21.0 | Homologous signal pelD |
| | | 4.3 | 3.9 | Strongest heterologous signals |
| | | 18.0 | 7.1 | Weaker signals |
| | | | 4.4 | Weak signals |
| | | 8.4 | 4.6 | Weak signals |
| | | 4.1 | 1.5 | Weak signals |
| pelD | 2.9 + 3.5 | 7.5 | large | |
| pelA | 7.5 | 4.3 | 3.9 | |
| pelB | 8.7 | large | 7.1 | |
| pelC | 5.0 | large | 4.4 | |
| pelE | 6.2 | 8.4 | 4.6 | |
| pelF | large | 4.1 | 1.5 + 2.8 | (very weak) |

A comparison of the hybridizing fragment lengths of the isolated genes and the hybridizing fragment lengths from genomic DNA blots is shown in Table III. From these data it is concluded that all the bands hybridizing in genomic blots, are present in the clones isolated and that under these hybridization conditions, no other related genes can be isolated. The plaque hybridization results (Example 12.3.) reveal that, not considering partial clones, every gene has a specific hybridization pattern with the probes tested. This is summarized in Table IV.

TABLE IV

Comparison of signal strength of different genes in homologous and heterologous plaque hybridization with different pelD probes according to the experiment described in Example 12.3. The degree of hybridization is expressed by the number of + signs. The homologous pelD gene hybridizes with at least 10 + sings; ±, very poor hybridization; −, no hybridization.

| | heterologous hybridization | | | homologous hybridization | | |
|---|---|---|---|---|---|---|
| probe | wbole gene | N-term | C-term | whole gene | N-term | C-term |
| pelA | ++++ | ++++ | ± | +++ | ± | − |
| pelB | ++++ | ++++ | ± | + | ± | − |
| pelC | +++ | ++++ | − | − | − | − |
| pelE | +++ | − | − | − | − | − |
| pelF | ++++ | ± | ± | ± | − | − |

EXAMPLE 12.5

Subcloning of pelD related genes into pBR322

Subclones of the hybridizing fragments which are obtained from λ clones described in Example 12.3 are made in the vector pBR322 which is digested by EcoRI, BamHI or HindIII and subsequently dephosphorylated. Fragment isolation, from LMP agarose gels, vector preparation, ligation, transformation of *E. coli* MH1, miniprep DNA isolation and large scale plasmid isolation is all done using standard procedures which have been described in Example 11.4.

Fragments are ligated into the proper vector as described in Example 11.4. Transformed *E. coli* MH1 cells are plated on LC+50 μg/ml Amp. Transformants are tested for tetracycline sensitivity. EcoRI clones are all resistent. Miniprep DNAs are then digested with appropriate enzymes to test for the right inserts and to determine the orientation of the fragments. The plasmids which have been selected are summarized in Table V. Cells harbouring them are stored on glycerol at −70° C.

TABLE V

Subclones of pel genes in pBR322.

| plasmid | gene | fragment | origin | orientation |
|---|---|---|---|---|
| pGW820 | pelA | 7.5 EcoRI | λ-PL113 | 2 |
| pGW821 | | 4.3 BamHI | | 2 |
| pGW822 | | 3.9 HindIII | | 2 |
| pGW823 | | 7.5 EcoRI | | 1 |
| pGW824 | | 4.3 BamHI | | 1 |
| pGW825 | | 3.9 HindIII | | 1 |
| pGW830 | pelB | 7.1 HindIII | λ-PL122 | 1 |
| PGW850 | pelC | 5.0 EcoRI | λ-PL109 | 1 |
| pGW851 | | 5.0 EcoRI | | 2 |
| PGW860 | pelF | 4.1 BamHI | λ-PL102 | 1 |
| pGW880 | pelE | 4.6 HindIII | λ-PL109 | 1 |
| pGW881 | | 4.6 HindIII | | 2 |

The plasmids pGW820, -830, -840, -850, -860 and -880 have been isolated on a large scale and subjected to restriction mapping. Maps of these plasmids are given in the FIGS. 9 to 14.

To determine gene location and orientation, Southern blots of plasmid digests are hybridized heterologously with the 1.6 kbp BamHI/PstI fragment of pGW840, and identical blots are hybridized heterologously with a N-terminal fragment of the same plasmid, which is the 649 bp BamHI/XhoI fragment for the mapping of pGW820 an -830, and the 766 bp BamHI/EcoRI fragment for pGW850 and -860.

The plasmids pGW820, pGW830, pGW850, pGW860 and pGW880 were cloned in *E. coli* HB101 and deposited on Feb. 1, 1988, at the Deutsche Sammlung für Mikroorganismen.

EXAMPLE 13

Sequence determination of the pelD, pelA, pelB and pelC gene

EXAMPLE 13.1

Partial sequence of the pelD gene from *A. niger* strain N400 and its identity with pel I from *A. niger* strain N756

Suitable restriction fragments are isolated from pGW840 after LMP agarose gel electrophoresis as described in Example 11.4. These are ligated into M13mp18RF and M13mp19RF vectors according to the BRL M13 cloning/dideoxy sequencing instruction manual (pp 26, 27; ref. 6). Transformation of *E. coli* JM103, plating on minimal X-gal indicator plates and isolation of single stranded DNA from recombinant phages are done according to the instructions in the same manual (pp 29–34). A few clones are sequenced using the Sanger dideoxy chain termination method described at pp 38–74 of the BRL manual.

The sequences determined between nucleotides -457 and +100 are identical to the corresponding sequence of the PLI gene derived from *A. niger* N756 and present in plasmid pCG3B11. The sequence determined from the BamHI at position -457 up to position +100 comprises 457 nucleotides of the promotor sequence, the 57 nucleotides encoding the signal sequence and 43 nucleotides encoding the first 13 N-terminal amino acids of the mature PLD protein.

From identical restriction maps of the N400 pelD gene in pGW840 and of the N756 pelD in pCG3B11 and the completely identical N-terminal sequence data it is assumed that both genes are identical. Accordingly it is assumed that the PLD protein is identical with the former PLI protein.

EXAMPLE 13.2

Sequence determination of the pelA, pelB and pelC gene

Fragments of pGW820, pGW830 and pGW850 are subcloned into M13 mp18RF and M13 mp19RF (see Example 13.1.) or into the plasmids pEMBL18 and pEMBL19 (Dente et al. ref. 7, 8). Single stranded DNAs of the plasmid clones are obtained by infection with helper phage R408 (Russell et al. ref. 9). Exonuclease III deletion clones were prepared of pGW850 by the method of Henikoff (ref. 28). The 3.0 kb SmaI-BglII fragment from pGW850 on which the pelC gene is situated is subcloned in pEMBL19. 50 μg of this clone is digested with SmaI and SacI and after phenol/-chloroform extraction and ethanol precipitation digested with exonuclease III. Samples are taken at different time intervals, the exonuclease III inactivated by adding NaCl and EDTA and incubation at 70° C. for 10 min. Protruding ssDNA ends are removed by $S_1$ nuclease and the sticky ends made blunt with T4 DNA polymerase. After selfligation and transformation of *E. coli* JM103 with these deletion clones single stranded DNAs are obtained by infection with helper phage R408. pGW820 is sequenced from the PvuII site at position 1000 until the ClaI site at position 4175 (see FIG. 9). In the case of pGW830 the 2774 bp XhoI fragment is sequenced (see FIG. 10). pGW850 is sequenced from the EcoRI site at position 0 until position 3168 (see FIG. 11).

Figure 15:
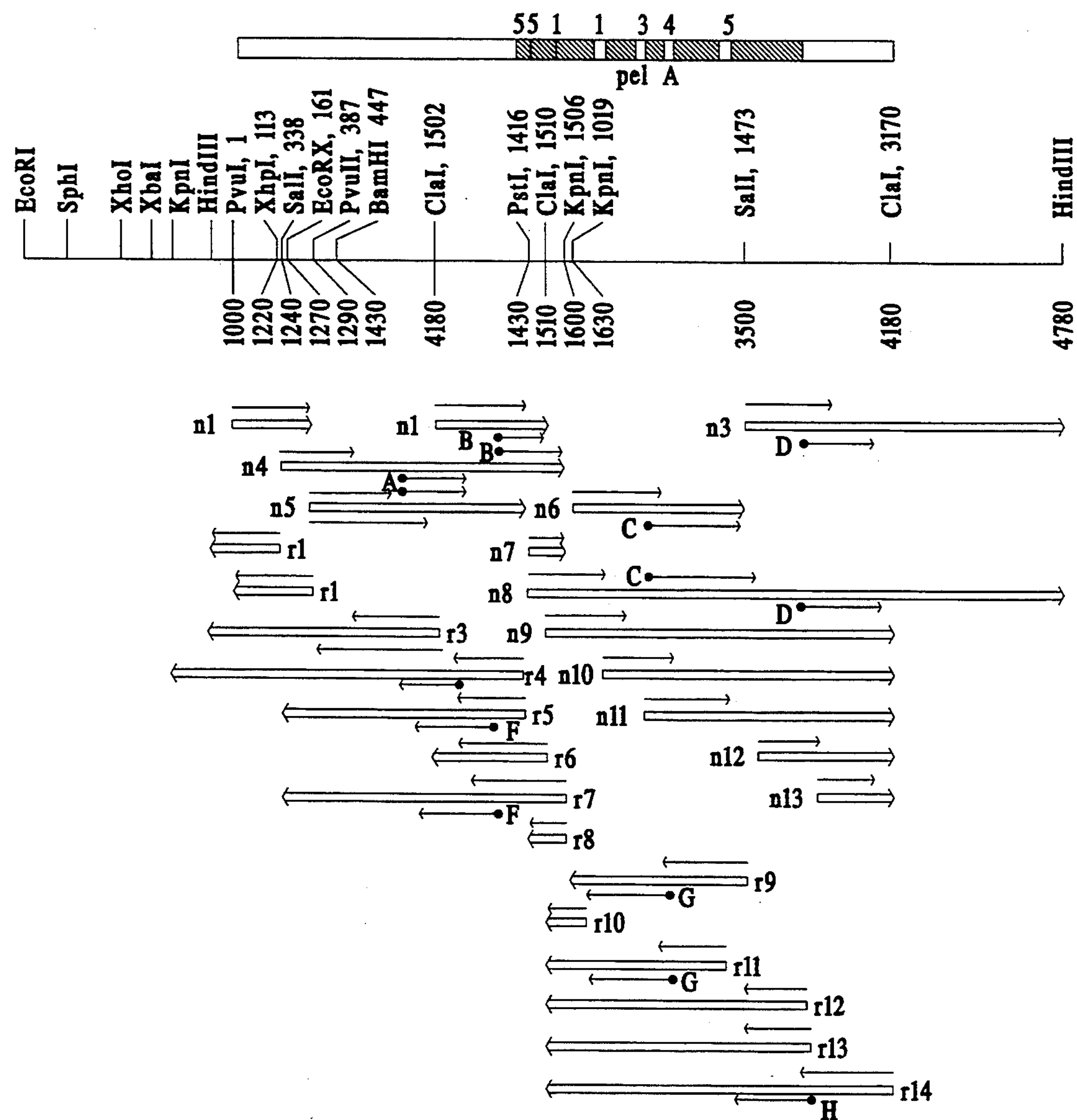
FIG. 15 shows the sequencing strategy for the pelA gene
Figure 16:
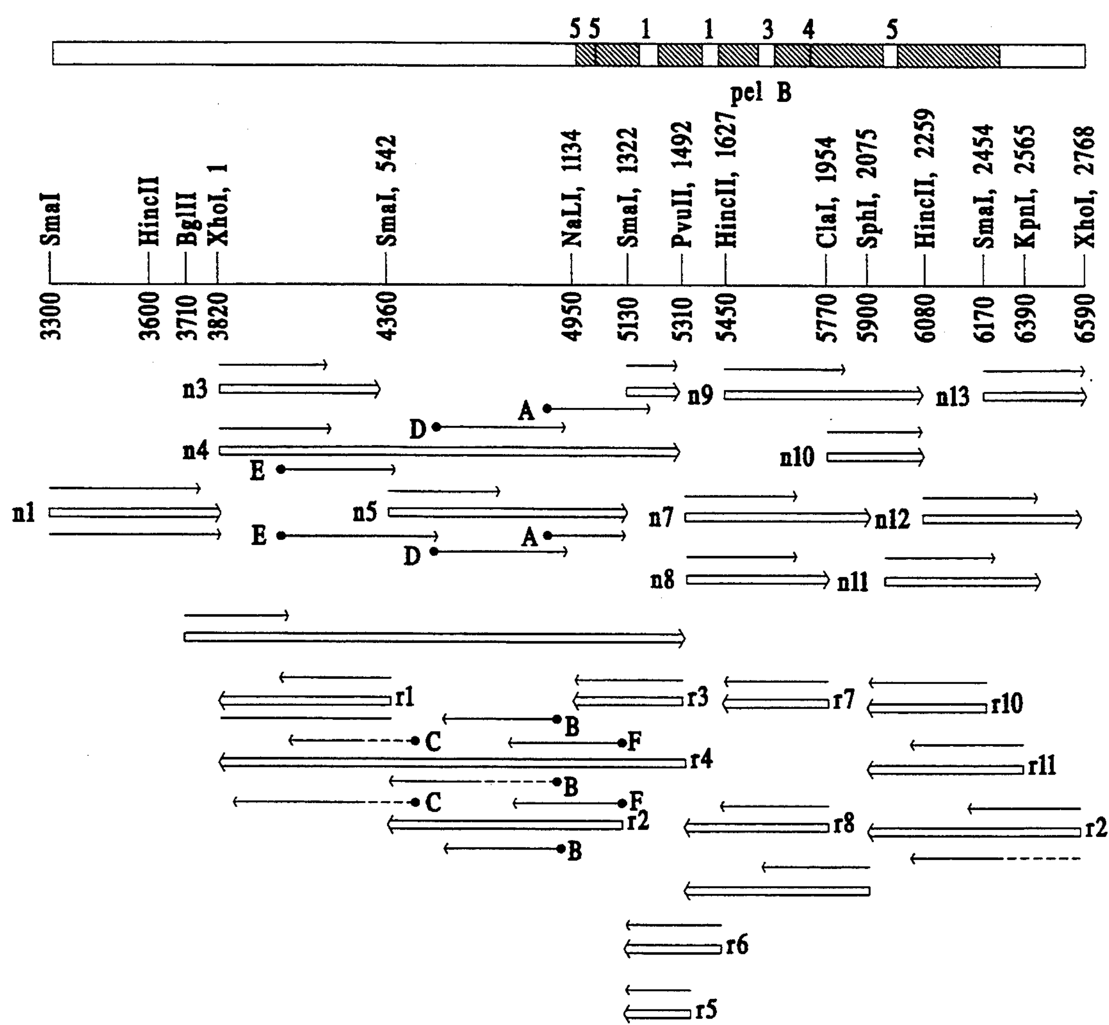
FIG. 16 shows the sequencing strategy for the pelB gene
Figure 17:
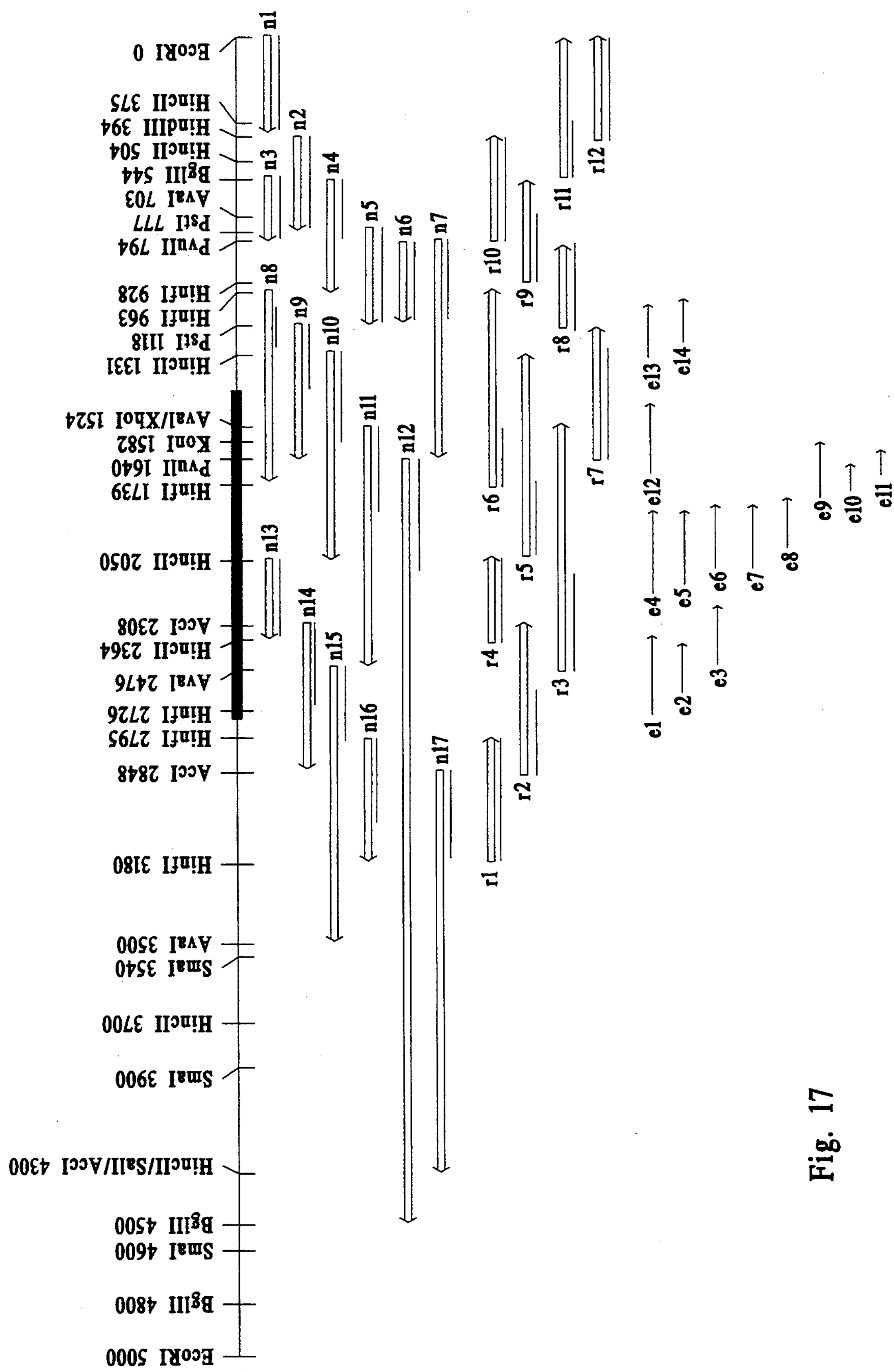
FIG. 17 shows the sequencing strategy for the pelC gene
Figure 19:
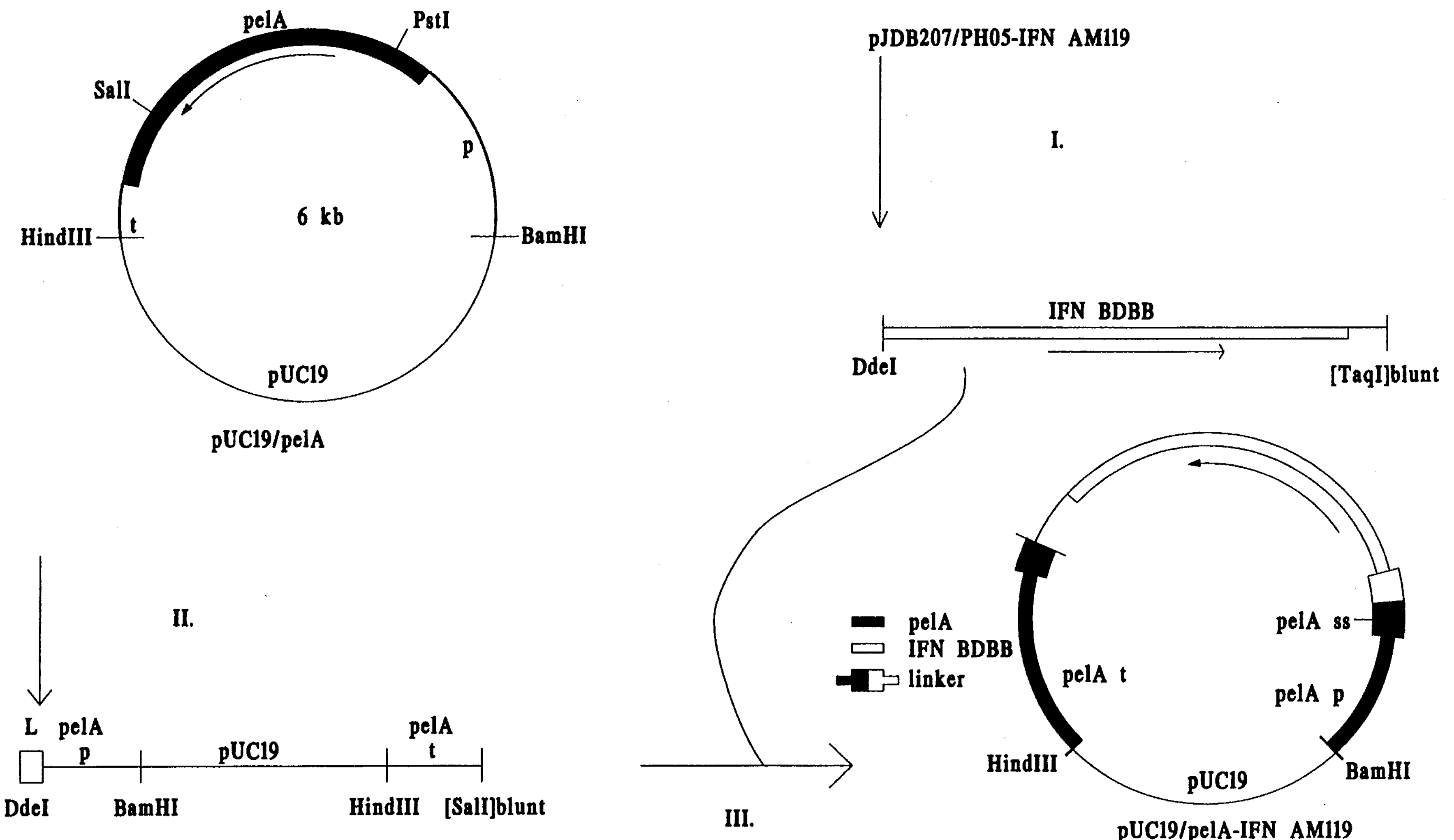
FIG. 19 shows the construction of the vector pUC19-/pelA-IFN AM119, containing the gene coding for the hybrid interferon BDBB.

The sequence strategies for these genes are indicated in FIG. 15 to 17. Several oligonucleotides are synthesized using the phosphoramidite method of Caruthers (ref. 10) using an Applied Biosystem (model 380B) oligonucleotide synthesizer. They are used as sequencing primers and their position is indicated in FIG. 15 and 16.

The entire sequence of the pelA gene is given in the sequence listing under SEQ ID NO. 2 in the 5'→3' direction. The 3175 bp sequence starts with the first nucleotide of the PvuII site at position 1000 in pGW820 and ends at the last nucleotide of the ClaI site at position 4175 in pGW820.

The pelA sequence comprises about 1360 nucleotides of the promoter region, about 1364 residues of the structural part and about 450 nucleotides of the terminator region.

The amino acid sequence of PLA (see SEQ ID No. 4) is preceded by a signal sequence of 20 amino acids as can be deduced from the nucleotide sequence.

The homology with the signal sequence of the pelD gene, also named pectin lyase I gene, is evident. Identical amino acids are in position 1 to 3, 9, 11, 12, 15, 18 to 20. Also, the first 5 residues of the mature protein have the same amino acid sequence in pelA and pelD (see SEQ ID No. 4 and SEQ ID NO:2.

The entire sequence of the pelB gene is given under SEQ ID NO. 3, also in the 5'→3' direction. The 2774 bp sequence starts with the first nucleotide of the XhoI site in pGW830 and ends at the last nucleotide of the second XhoI site.

The pelB sequence comprises about 1133 nucleotides of the promoter region, about 1368 residues of the structural part and about 270 of the terminator region. The pelB gene codes for a signal sequence of at least 20 amino acids.

The pelC sequence with SEQ ID NO.7 and 8 comprises 1367 nucleotides of the promoter region, 1340 residues of the structural part and 461 of the terminator region. The pelC gene codes for a signal sequence of 18 amino acids.

Searches for consensus sequences for fungal exon/intron splice junctions and intron internal sequence (Ballance, ref. 11) leads us to postulate the presence of four introns in the pelA, B and C gene. The positions at which the introns are located within the coding regions of these pel genes are conserved in the sense that there are potentially five intron positions but in each gene a different intron lacks. However, for the pelC gene only three introns are postulated. Of these only one is found in a position corresponding to the position of an intron in pelD and pelA (intron 5). The positions of these introns and their respective lengths are evident from the sequence listing.

The lengths of the exons between introns amongst the four pel genes, is the same in these cases. In FIG. 18 the aligned derived amino acid sequences of PLA, PLB, PLC, and PLD are shown. In the N-terminal part of the coding regions of pelA, pelB and pelD approx. 80% homology is observed on the basis of nucleotide sequence homology and over 80% on the basis of amino acid sequence homology. This percentage is much lower with pelC. In the C-terminal part of pelA, pelB and pelD beyond residue 285 of the mature protein (corresponding to residue 305 in FIG. 18) the homology is lost to a large extent and only returns near to the C-terminus.

Except for the consensus sequences of the splicing signal and of the 5'- and 3'-splicing sites no homology is found in the introns.

The derived amino acid sequences for the proteins PLA, PLB, PLC and PLD indicate a total of 359 residues for the first two proteins, 360 for PLC and 354 for PLD. With respect to N-glycosylation, one potential glycosylation site is present in all four proteins at position 109 (in the mature protein, i.e. without signal sequence) (for PLC this corresponds with position 105 in the non-aligned sequence). In PLB a second potential site is present at position 232 whereas in PLD two other potential glycosylation sites are present at residues 255 and 329.

EXAMPLE 14

Cotransformation of *A. niger* using the *A. niger* pyrA gene as selection marker and the various *A. niger* pel genes as cotransforming plasmids

EXAMPLE 14.1

Propagation and purification of plasmids used to transform *A. niger*

All plasmids are propagated in *E. coli* strain MH1 and plasmid DNA is recovered from 500 ml overnight cultures as described by Maniatis et al. pp 90–91; ref. 5). To 2.5 ml DNA solution in TE, containing up to 1 mg DNA, 2.2 g CsCl and 1 ml ethidium bromide (10 mg/ml in water) are added. The solution is taken to quick seal tubes, which are filled and sealed as recommended by the supplier (Beckman). Centrifugation takes place in a VTi 65.2 rotor at 20° C. for 16 hrs at 45.000 rpm. Of the two fluorescent bands visible under ultraviolet light, the lower one containing plasmid DNA is isolated by side-puncturing of the tube. The DNA solution (approx. 1 ml) is extracted 5 times with water-saturated butanol to remove ethidium bromide. Then the DNA is precipitated by ethanol, resuspended in TE, extracted once with phenol/chloroform and chloroform, precipitated again and stored at −20° C.

The plasmid pGW613 which carries the OMP-decarboxylase gene (pyrA) on a 5 kbp *A. niger* DNA fragment is used to select transformants (Goosen et al.; ref. 12). Plasmids pGW820, pGW830, pGW840, pGW850, pGW860 and pGW880 which are described in Example 12.5 are used as co-transforming plasmids.

EXAMPLE 14.2

Preparation of protoplasts and transformation of the uridine auxotrophic mutant *A. niger* strain N593

The *A. niger* strain N593 (cspA, pyrA) which is a derivative of the parental strain N400 has been obtained by positive selection against the toxic analogue 5-fluoro orotic acid like in yeast (Boeke et al.; ref. 13) in the presence of uridine as described by Goosen et al.; (ref. 12).

Liquid minimal medium supplemented with 0.5% yeast extract, 0,2 casamino-acids, 10 mM uridine (Janssen Chimica) and 50 mM glucose is inoculated with $10^6$ conidiospores of *A. niger* N593 per ml and incubated for 20 hrs at 30° C. in a New Brunswick orbital shaker. Mycelium is harvested by filtration, through Miracloth, washed with iso-osmotic (STS) minimal medium (STC) of the following composition: 1.33M sorbitol, 10 mM Tris-HCl pH 7.5, 50 mM $CaCl_2$ adjusted to 1.7 mOsm. An amount of 1 g of mycelium is resuspended in 20 ml STC. Protoplasts are released from the mycelium within 2 hrs by adding 250 mg of filter-sterilized Novozym 234 (Novo Industries, Denmark) and incubating the mixture at 30° C. in a shaker at 95 rpm. The protoplasts are separated from residual mycelium by filtration using a funnel with a plug of glasswool and purified by centrifugation (10 min, 2500 rpm) by pelleting and resuspending in STC.

For transformation $5\times10^6$ protoplasts are taken in 200 μl which are then incubated together with 1 μg pGW613 and 10 μg of one of the following plasmids pGW820, pGW830, pGW850, pGW860 or pGW880 (volume less than 20 Bl). For pGW840 a ratio of 1:3 is used taking 6 μgs of pGW613. After the addition of plasmid DNA to the protoplasts 50 μl PCT (10 mM Tris-HCl pH 7.5, 50 mM $CaCl_2$, 25% PEG6000) is added and the incubation mixture is kept on ice for 20 min.

Then another 2 ml PCT is added and the mixture is incubated for a further 5 min at room temperature. Finally, 4 ml STC are added and mixed. Aliquots of 1 ml of this final transformation solution are mixed with 4 ml liquified iso-osmotic MM top-agar stabilized by 0.95M sucrose (adjusted to 1.7 mOsm). The protoplast mixture is immediately plated on agar plates containing the same iso-osmotic minimal medium and these are incubated at 30° C. Appropriate control experiments include protoplasts treated similarly without plasmid DNA and on non-stabilized minimal medium with 2.5 mM uridine.

After 3 days of growth at 30° C. well growing transformants appear which sporulate (50–150 transformants/μg pGW613). Besides, a large number of presumably abortive transformants appear. Spores of individual transformants are then taken and plated out separately on 50 mM glucose minimal medium to obtain single colonies which are used to propagate spores for further transformant analysis.

In each case at least ten transformants are cultured on liquid minimal medium, the DNA is extracted and analyzed for the presence of co-transforming plasmid DNA. Fungal DNA is isolated by a slightly modified procedure used to isolate plant RNA (Slater, ref. 14). Mycelium is washed with saline, frozen in liquid nitrogen and 0.5 g is disrupted using a microdismembrator (Braun). The mycelial powder is extracted with freshly prepared extraction buffer. The extraction buffer is prepared as follows:

1 ml tri-isopropylnaphthalene sulphonic acid (TNS) 20 mg/ml is mixed with 1 ml p-aminosalicylic acid (PAS) (120 mg/ml) and 0.5 ml 5×RNB buffer (5× RNB contains 121.1 g Tris, 73.04 g NaCl and 95.1EGTA in 1 l, pH 8.5). After the addition of 1.5 ml phenol, the extraction buffer is equilibrated for 10 min at 55° C. The warm buffer is then added to the mycelial powder and the suspension thoroughly mixed for 1 min using a vortex mixer. Then 1 ml chloroform is added and mixed for 1 min.

By centrifugation (10 min, 10.000×g) the aqueous phase is separated and extracted once more with an equal volume of phenol/chloroform (1:1) and then twice with chloroform.

The aqueous phase contains both RNA and DNA. The DNA is precipitated with 2 vol ethanol at room temperature and collected by centrifugation (10 min, 10.000×g), washed twice by redissolving in distilled sterile water and precipitating it again with ethanol. RNA is removed by adding RNase A (20 μg/ml) to the final solution. The procedure results in high molecular weight DNA (100–200 kbp) with a yield of about 300 μg DNA/g mycelium which is further purified by CsCl/ethidium bromide density gradient centrifugation essentially according to Maniatis et al. μg 93; (ref. 5).

Digests of the chromosomal DNA (2 μgs) are made by incubating for 2 hrs at 37° C. with EcoRI for pelA (pGW820) and pelC (pGW850) transformants, Hind III for pelB (pGW830) transformants, EcoRI or Bgl II for pelD transformants. In all cases initially 20 U of restriction enzyme are used after which the incubation is prolonged for another 2 hrs by adding agains 20 U of the restriction enzymes. The digestions are carried out in the appropriate reaction buffers supplied by BRL.

Then the DNA is fractioned on 0.6% agarose, blotted on nitrocellulose and hybridized essentially as described by Maniatis et al. (ref. 5), pp 382–386 using the corresponding [$\alpha$-$^{32}$ p] labelled probes.

The following cotransformation frequencies are found: pGW820 (pelA) 70%; pGW830 (pelB), 70%; pGW840 (pelD) 15%; pGW850 (pelC) 60%. The mass ratio of pGW613 versus the cotransforming plasmid pGW820, pGW830, pGW850 (1:10) and pGW840 (1:3) leads in the majority of the cases observed to multicopy chromosomal integration of the cotransforming plasmids.

EXAMPLE 14.3

Genomic analysis of the pelA transformed *A. niger* strain A15

A number of the multicopy tranformants described in example 14.2 has been analyzed and the analysis of the pelA transformant A15 is given as a detailed example.

DNA of the *A. niger* strain N593 and of the multicopy transformant pelA strain A15 is isolated and analyzed by hybridization of Southern blots as described in Example 3.1. As a pelA probe the 7.5 kbp EcoRI fragment is used (see FIG. 3a). In the genomic blot an intense band of 7.4 kbp is found in the transformed strain A15 which results from type I and/or type II integration events (cf. Hinnen et al., ref. 14a). Also some minor bands of various lengths are found which represent border fragments of type II integration events of rearrangements.

The optical densities of the 7.4 kbp EcoRI bands in the *A. niger* pelA transformants A15 and *A. niger*. N593 autoradiograms are scanned using an Ultroscan XL (LKB). The values are corrected for slight differences in the DNA concentration between N593 and the transformant A15 by scanning the densities obtained with a second probe which hybridizes with the pyruvate kinase gene, present as single copy in both strains. From these data it is calculated that in the pelA transformant A15 approx. 19 intact copies of the pelA gene are present.

Using the HindIII insert of pGW830 (FIG. 10) as a probe, analysis of the Southern blot of the transformed strain A15 indicates that integration of pelA sequences has not occurred in the pelB locus. Similarly, analysis of the transformed pelB strain B13, the pelC strain C16 and the pelD strain D12 with the appropriate corresponding probes give copy numbers of approx. 15, 50 and 10.

EXAMPLE 14:4

Northern blot analysis of induced and non-induced mycelia of the pelA transformed *A. niger* strain A15 and of *A. niger* N400

Minimal medium (250 ml) containing 50 mM glucose or 1% (w/v) of apple pectin (Brown Ribbon, d.e. 72.8%, Obipektin AG, Bischofszell) is inoculated at a spore density of $10^6$ spores/ml with spores of transformant A15 or spores of the wild type strain N400 is harvested after 30 hrs of growth at 30° C. Samples of the culture medium (2 ml) are also collected, dialyzed against 2 1 10 mM sodium phosphate buffer pH 7.0 at 4° C. and stored at −20° C.

Nucleic acids are isolated from the mycelium as described in Example 14.2. The RNA is precipitated from the aqueous phase after chloroform extraction by adding ⅓ volume of 8M LiCl. The solution is thoroughly mixed and incubated overnight at 0° C. The RNA is collected by centrifugation (300 rpm for 30 min.) using a MSE Super-MInor centrifuge and then washed once with cold (−20° C.) 2M LiCl and once With cold (−20° C.) 96% ethanol. Finally the RNA is dissolved in distilled water at a concentration of about 1 mg/ml. The preparations essentially free of DNA with a yield of 1–2 mg RNA per g mycelium. Amounts of approx. 10 μg of RNA are run on denaturing formaldehyde 1% agarose gels according to Maniatis et al. pp 202–203; ref. 5) using Hind III digested lambda DNA or the RNA ladder from BRL as molecular weight markers. The gels are blotted and baked on Nytran (Schleicher and Schuell) as recommended by the manufacturer and hybridized at 68° C. for 16 hrs with the 7.4 kbp EcoRI pelA DNA probe. Hybridization and washing procedures are those described for DNA hybridization under homologous conditions according to Example 12.2.).

Both *A. niger* strains produce a pectin-inducible mRNA with a length of approx. 1.6 kbp. Scanning of the optical densities of the two autoradiograms indicates a 15–20 fold difference in intensity between the A15 transformant and the wild type strain which correlates with the increase in copy number calculated from the Southern blot analysis.

EXAMPLE 14.5

Pectin lyase production by the transformed *A. niger* strain D12

The *A. niger* pelD transformant D12 obtained according to Example 14.2 is grown in a 2-step cultivation procedure similar to the procedure described by Hermersdörfer et al (27) for the production of polygalacturonase. A mycelium layer is formed on top of a liquid culture by modulating $10^6$ spores per ml of Pre Cultivation Medium (PCM) consisting of sugar beet pulp (4%) and $NH_4NO_3$ (1%) pH 4.5. After 5 days growth period at 30° C. the mycelium grown in 30 ml of medium is washed with saline and transferred to 50 ml of Main Cultivation Medium (MCM). This culture is grown at 30° C. in an orbital shaker at 100 rpm. The composition of MCM is per liter of medium, glucose (5%), pectin (d.e. 72.8%; 0.1%), $NH_4N_3$ (0.75%), $KH_2PO_4$ (0.5%), $FeSO_4$ $7H_2O$ (0.03%), $MgSO_4$ $7H_2O$ (0.03%), $CaCO_3$ (0.03%), $NaNO_3$ *l* (0.03%) pH 4.5. Samples have been taken during 24 hours at different time intervals and are analyzed by SDS polyacrylamide gelelectrophoresis. Expression of pelD is already maximal within 7 hours of cultivation. The protein migrates identical to PLI used as a reference.

EXAMPLE 14.6

Pectin lyase A production by the transformed *A. niger* strain A15 and by *A. niger* N400

The dialyzed culture filtrates (Example 14.4.) are lyophilized, resuspended in 0.2 ml distilled water and subjected to SDS-polyacrylamide gel electrophoresis (10% gels), using standard methods (Laemmli, ref. 15). The separated proteins are transferred to nitrocellulose (Towbin et al. ref. 16). Blots are saturated for 5 hrs at room temperatures with a 1% BSA solution in 10 mM Tris-HCl buffer pH 7.5 with 0.35M NaCl. This is followed by an incubation for 16 hrs at room temperature with polyclonal antibody (0.1%) raised against two pectin lyases purified according to van Houdehoven (1975) in 50 ml of the same buffer containing 150 mM NaCl, 0.5% BSAm 1% Triton X100, 0.5% deoxycholate and 0.1% SDS. Blots are then rinsed 5 times with 200 ml PBS before incubation with 30 μl goat anti-rabbit IgG-HRP (Sigma) as 2nd antibody per 50 ml and washed again 5 times with PBS. The blots are finally stained using 4-chloro-1-naphthol as a substrate. 40 mgs of the substrate are solved in 0.5 ml 96% ethanol and mixed with 100 ml 50 mM Tris-HCl pH 7.5 and 30 μl 30% hydrogenperoxide and then added to the blots.

EXAMPLE 14.7

Screening of pelA transformed strains by halo-formation on pectin-containing solid media Conidia of pelA transformed strains are inoculated at a spore density of approx 40 colonies per Petridish on sterile paper filters (Schleicher and Schuell) which are put on top of 1% agar-solidified minimal medium containing 0.01% Triton-X100 and apple pectin (1%, d.e. 72.8% Obipektin) as carbon source. The incubation period is 72 hrs at 30° C. resulting in individual colonies (2–4 mm). The paper filter is transferred to another sterile Petridish and the medium containing dish is stained with at least 5 ml of a ruthenium red (0.1% w/v) solution in distilled water, incubated for 2 hrs and then washed several times with distilled water to remove the unadsorbed dye-stuff, following essentially a procedure described by Ried and Collmer (ref. 17) for polygalacturonate to characterize bacterial pectate lyase enzyme activities.

Transformants overproducing PL A protein are detected by an increase in halo-diameter around the individual colonies as compared to the parental strain N400.

EXAMPLE 15

Isolation, purification and characterization of pectin lyase A (PLA) from the *A. niger* pelA transformant A15

EXAMPLE 15.1

Culture conditions to prepare pectin lyase A

The *A. niger* pelA transformant A15 described in Example 14 is grown on complete medium in Petridishes for 3 days at 28° C. to produce conidia. The conidia are harvested from these plates by suspending the spores in 5 ml sterile saline containing 0.005% Tween 80. The suspension is heavily agitated on a Griffin shaker for 20 min. Minimal medium (ref. 21) containing 1% (w/v) of apple pectin (Brown Ribbon, d.e. 72.8%; Obipektin AG, Bischofzell) is inoculated at a spore density of $10^6$ spores/ml using 250 ml of medium in 1 l siliconized Erlenmeyer flasks. The mycelium is grown for 40 hrs at 30° C. using a Gallenkamp orbital shaker at 200 rpm. After cultivation the mycelium is removed by filtration over Miracloth using a Büchner funnel. The culture filtrate (ref. 21) is diluted with distilled water (ref. 21), the pH of the filtrate (pH 3.7) is taken to pH 6.0 using 1N NaOH and then filtered again using Whatman 1 filter paper.

EXAMPLE 15.2

Purification of PLA

The diluted culture filtrate (4 l) is applied to a DEAE-Sepharose Fast Flow (Pharmacia) column (10 cm×2.6 cm), pre-equilibrated with 20 mM sodium phosphate buffer pH 6.0. The column is eluted with the same buffer until the absorbance at 280 nm reaches a value <0.1 O.D. Pectin lyase activity is then eluted from the column by applying a linear gradient composed out of 20 mM sodium phosphate buffer (150 ml) and 20 mM sodiumphosphate buffer containing 1M NaCl (150 ml).

Fractions are assayed for the presence of active pectin lyase according to the procedure described by van Houdenhoven (ref., 18 p. 11) using Brown Ribbon pectin (d.e. 72.8%) as a substrate. The activity appears around a concentration of 0.43M NaCl in the salt gradient. Active fractions are then pooled and dialyzed twice against 1 l of 20 mM piperazine HCl buffer pH 5.5 (sample size: 45.5 ml).

In the next step the dialyzed sample is divided into 3 portions of equal size which are subjected to anionic exchange chromatography in three separate runs using a standard Pharmacia MONO Q column in combination with the Pharmacia FPLC system. The column is pre-equilibrated with 20 mM piperazine-HCl buffer pH 5.5. After loading of the enzyme sample the column is eluted with the same buffer at a flow rate of 1 ml/min until base-line absorbance is reached again. Then a linear salt gradient is applied. Within 22 ml of the elution buffer applied to the column, a final concentration of 0.6M NaCl is reached.

The active fraction (4.4 ml) are collected, diluted to 25 ml using equilibration buffer and the same chromatography procedure is repeated.

Two fractions containing the active enzyme (total volume 3 ml) are then dialyzed against a 25 mM piperazine buffer pH 5.0 and injected in 1 ml portions onto a MONO P column (Pharmacia), pre-equilibrated with the same buffer. After the injections a pH gradient is formed using a 5% solution of polybuffer TM 74 (in distilled water set at pH 3.0 using 4N HCl). The active enzyme (3.2 ml) appears around pH 3.2. The preparation is extensively dialyzed against 50 mM sodium phosphate buffer pH 6.0 and stored at −20° C. The purification results are summarized in Table VI and are compared with the data of a similar purification for pectin lyase produced by *A. niger* strain N400 (Table VII).

TABLE VI and VII

Purification scheme of pectin lyase A from the *A. niger* pelA N593 transformant and pectin lyase from *A. niger* strain N400.

| Step | Volume ml | Total activity (I.U.) | Specific pectin lyase activity (I.U./mg of protein) |
|---|---|---|---|
| | VI (transformant) | | |
| DFAE Sepharose | 45.5 | 39.8 | 4.9 |
| MONO Q chromatography (2 ×) | 2.3 | 19.9 | 18.4 |
| MONO P chromatography | 3.2 | 17.4 | 28.6 |
| | VII (wild type N400) | | |
| DEAE Sepharose | 43.0 | 10.1 | 0.9 |
| MONO Q chromatography (2 ×) | 1.1 | 2.5 | 6.3 |
| MONO P chromatography | 1.4 | 1.7 | 10.0 |

Protein concentrations have been determined using the BCA protein assay reagent (Pierce) according to the instructions of the manufacturer.

Compared to the wild type total activity the total activity of the *A. niger* N592 transformed with pGW820 has increased after purification about 10 times and the specific activity about 3 times.

EXAMPLE 15.3

Amino Acid sequence determination of the N-terminal part of pectin lyase A

500 μg of pectin lyase (PLA), purified according to Example 15.2. are dialyzed three times against 1 l Millipore filtered distilled water and lyophilized. Amino acid sequences are determined with an Applied Biosystems model 470A protein sequencer, on-line connected with a 120 A PTH analyzer, according to the method described by Hunkapiller (ref. 17).

The N-terminal amino acid sequence thus determined corresponds exactly with the one based on the nucleotide sequence of the pelA gene (see Example 13.2.).

EXAMPLE 15.4

Properties of pectin lyase A

Both the *A. niger* strain N400 and the pelA transformant A15 are cultivated as described in Example 15.1 and the enzyme is purified from the culture filtrate according to the procedure in Example 15.2. The two enzyme preparations thus obtained have been compared with pectin lyase II which is purified according to van Houdenhoven (ref. 18). SDS polyacrylamide gelelectrophoresis, using 10% gels, results in a single band of identical molecular weight in all three cases applying in each case 2–5 μg of protein.

Isoelectric focussing has been performed using standard procedures (see e.g. instruction leaflet of Pharmacia, Isoelectric Focussing, 1982). A FSBE-3000 apparatus and the corresponding power supply ECPS 3000/150 (Pharmacia) have been used. The obtained PLA is homogeneous upon isoelectric focussing and has a lower isoelectric point (0.2 pH units) than PLII reported to be 3.75 according to van Houdenhoven (ref. 18). The PLII purified from the N400 culture filtrate is heterogeneous upon isoelectric focussing. The major band corresponds in position with the PLA protein. Two minor bands are shifted slightly towards the cathode. Thus in the *A. niger* multicopy transformant A15 the minor enzyme forms seen in N400 are lacking.

A direct comparison of the kinetic parameters of PLA and of PLII, which in the latter case were established by van Houdenhoven (ref. 18), using 95% esterified apple pectin as substrate indicates identical $K_m$ and $V_{max}$ values for both enzymes.

EXAMPLE 16

Isolation, purification and characterization of pectin lyase D (PLD) from the *A. niger* pelD transformant D12

EXAMPLE 16.1

Culture conditions to prepare pectin lyase D

The *A. niger* pelD transformant D12 obtained according to Example 14.2 is initially grown according to Example 14.5, in 300 ml aliquots. After a 5 day growth period in PCM at 30° C., the mycelial mat is then transferred to 20 mM sodium phosphate buffer (pH 6.0), containing 0.1M sodium chloride. By shaking the mycelium in 150 ml on an orbital shaker at 200 rpm for 2 hr, most of the pectin lyase is released into the medium.

EXAMPLE 16.2

Purification of PLD

After removal of the mycelium by filtration, the enzyme solution is applied to a DEAE-Sepharose Fast Flow (Pharmacia) column (25 cm×1.25 cm) preequilibrated with 20 mM sodium phosphate buffer (pH 6.0), containing 0.2M sodium chloride. The column is eluted with the same buffer until the absorbance at 280 nm reaches a value <0.1. Pectin lyase activity is eluted from the column by applying a linear sodium chloride gradient (0.2 to 0.7M) in 20 mM sodium phosphate buffer (pH 6.0) (800 ml total volume). The fractions are screened for the presence of pectin lyase D by SDS-polyacrylamide gel electrophoresis and Western blotting (Towbin et al., ref. 16) as described in Example 14.6. Fractions containing pectin lyase D are pooled and dialyzed against 20 mM sodium phosphate buffer (pH 6.0) containing 0.15M sodium chloride, and subjected to anionic exchange chromatography using a standard Pharmacia MONO Q column in combination with the FPLC system. After loading, the column is waged with the same buffer before applying a 50 ml linear sodium chloride gradient in 20 mM sodium phosphate buffer (pH 6.0). Active fractions are collected and aliquots of 1 ml were applied to a 100 ml Superose-12 gel permeation column, equilibrated in 20 mM sodium phosphate (pH 6.0) containing 0.2M sodium chloride and connected to the FPLC system. Active enzyme fractions (1 ml each) obtained from the GPC column are analyzed by SDS polyacrylamide gel electrophoresis to check the purity of the pectin lyase obtained.

TABLE VIII

Purification scheme of pectin lyase D from *A. niger* pelD transformant D12

| Step | volume (ml) | Activity (I.U.) | Specific pectin lyase activity (I.U./mg protein) |
|---|---|---|---|
| culture filtrate | 1950 | 109 | 0.096 |
| DF-AE-Sepharose FF | 103 | 32.2 | 5.65 |
| MONO Q and GPC | 14.5 | 10.4 | 7.5 |

EXAMPLE 16.3

Amino acid sequence determination of the N-terminal part of pectin lyase D

500 μg of pectin lyase D, purified according to Example 15.2. are dialysed three times against 1 l Millipore filtered distilled water and lyophilized. Amino acid sequences are determined with an Applied Biosystems model 470A protein sequencer, on-line connected with 120A PTH analyser, according to the method described by Hunkapillar (ref. 19).

The amino acid sequence determined corresponds exactly with the one based on the nucleotide sequence of the pelD gene.

EXAMPLE 17

Isolation, purification and characterization of pectin lyase B (PLB) from the *A. niger* transformant B13

EXAMPLE 17.1

Culture conditions to prepare pectin lyase B

The *A. niger* pelB transformant B13, obtained according to Example 14.2 is analyzed for its multicopy character according to Example 14.3. Nothem blot analysis, according to the procedure described in Example 14.4, shows that a pectin-inducible mRNA with a length of approximately 1.6 kb is produced. Growth for 35 hr at 30° C. in minimal medium containing 1% (w/v) citrus pectin (d.e. 72.8%) and 1% of wheat bran is used to produce the enzyme as described in Example 14.4. The enzyme is also produced using a medium composed of 4% (w/v) sugar beet pulp and 1% $NH_4H_3$.

EXAMPLE 17.2

Purification of PLB

The culture filtrate is diluted two-fold with distilled water and pH is taken to pH 6.0 using 1N NaOH and then filtered again using Whatman 1 filter paper. The diluted filtrate (2 1) is then applied to a DEAE-Sepharose Fast Flow (Pharmarcia) column (9 cm×3.2 cm) which is preequilibrated with 50 mM sodium acetate buffer pH 5.0. Part of the pectin lyase activity is present in the eluate as can be assayed by the procedure described by van Houdenhoven (ref. 18, p. 11) using Brown Ribbon pectin (d.e. 72.8%) or highly esterified pectin (d.e. 94%). The majority of the pectin lyase activity can be eluted by applying a salt gradient. This activity appears in the salt gradient and is found to be identical to PLA on the basis of elution behaviour and apparent molecular weight on SDS-polyacrylamide gel electrophoresis as described in Example 15.

The eluate of the DEAE Fast Flow column is dialyzed against distilled water and applied to a MONO S column (Pharmarcia), which has been previously equilibrated with a 20 mM sodium acetate buffer pH 4.5. The enzyme is eluted from the column by applying a 0–1.0M sodium chloride salt gradient in the same buffer. The enzyme is eluted almost immediately from the column. Active fractions are pooled, and then diluted approximately four-fold with distilled water. Rechromatography of the enzyme solution results in fractions which on the basis of SDS-polyacrylamide gel electrophoresis contain the pure PLB protein.

EXAMPLE 17.3

Properties of pectin lyase B

The properties of the enzyme purified from the pelB transformant B13 according to Example 17.2. are determined and compared with pectin lyase A and D.

SDS polyacrylamide gel electrophoresis using 10% gels, results in a single band with an apparent molecular mass of 39.7 kDa. Under the same conditions the apparent molecular mass of PLA and PLD are 49.1 kDa and 52.3 kDa respectively.

Isoelectric focussing is performed as described in Example 6.4. The isoelectric point of PLB is 6.0 using a pH gradient between pH 3 and 7. The sample is approximately applied at a position corresponding to a pI of 5.0.

The purified enzyme PLB is also reactive with polyclonal antibodies prepared against PLI and PLII as tested by Western blot analysis. PLD, A and B can easily be discriminated this way by their apparent molecular mass values.

EXAMPLE 17.4

Kinetic properties of PLB

The enzyme purified according to Example 17.2 is characterized kinetically. The enzyme catalyses a pectin lyase reaction and is active over a wide pH range (pH 5–9.5) as tested in Mc Ilvaine buffer ($\mu$=0.5) of different pH values (van Houdenhoven, ref. 18). The pH optimum is broad (pH 7.5–8.5). At pH 6.0, the activity is approximately 55%; at pH 9.5 this is still 85% of the activity at pH 8.0. Both highly esterified pectin (d.e. 94%) as well as pectins with lower degree of esterification like Brown Ribbon apple pectin (d.e. 72.8%; Obipektin AG Bischoffzell) can be used as substrate. The highest activity is obtained with highly esterified pectin, however. The enzyme does not react with polygalacturonate.

The pectin lyase reaction catalyzed by PLB can be inhibited by adding EDTA to the reaction mixture (3 mM final concentration is used); the enzyme is reactivated by the addition of excess of $Ca^{2+}$-ions. Thus, pelB codes for a $Ca^{2+}$-depenent pectin lyase. At 25° C. the enzyme has an approximate turn-over number of 6500 and a Km value of 2.5 mM when using highly esterified pectin as a substrate. These values are determined according to the procedure of van Houdenhoven (ref. 18) using a Mc Ilvaine buffer of pH 8.0 ($\mu$=0.5).

EXAMPLE 18

Expression and secretion of foreign genes under the control of the pelA promoter The 3.9 kb HindIII fragment of plasmid pGW820 is subcloned into the HindIII site of pBR322. The plasmid DNA of ampicillin-resistant transformants is analysed by HindIII and SalI restriction digests. One clone which contains the pelA insert in clockwise orientation is referred to as pGW822. The inducible promoter of pelA is used to express foreign genes in *A. niger*. The complete pelA gene is present on plasmid pGW822. The promoter and the pelA signal sequence are on a 1 kb BamHI-PstI fragment. The PstI cleavage site at nucleotide position 1420 (FIG. 10) coincides with the 3′ end of the signal sequence and can be used for the in frame fusion to the coding sequence of a foreign protein. The transcription termination signals of pelA are on a 1.3 kb SalI-HindIII fragment.

EXAMPLE 18.1

Subcloning of the pelA gene in vetor pUC19

The 3.3 kb BamHI-HindIII fragment of plasmid pGW822 contains the pelA gene. The fragment is cloned in the vector pUC19 (Pharmacia) cut with BamHI and HindIII. The purified fragments are ligated. An aliquot of the ligation mixture is used to transform $Ca^{2+}$0 treated, competent JM109 cells. Successful cloning of the 3.3 kb BamHI-HindIII fragment into pUC19 is selected for on ampicillin plates in the presence of X-Gal and IPTG (T. Maniatis et al. in "Molecular Cloning, A Laboratory Manual", Cold Spring Harbor Laboratory, 1982, p. 52). White, ampicillin-resistant transformants are picked. Plasmid DNA of these colonies is analysed by BamHI/HindIII double digestion. One transformant with a correct insert is referred to as pUC19/pelA. An analogous construction with pUC18 results in pUC18/pelA.

EXAMPLE 18.2

Expression of human hybrid interferon BDBB under the control of the pelA promoter 18.2.1

Figure 14:
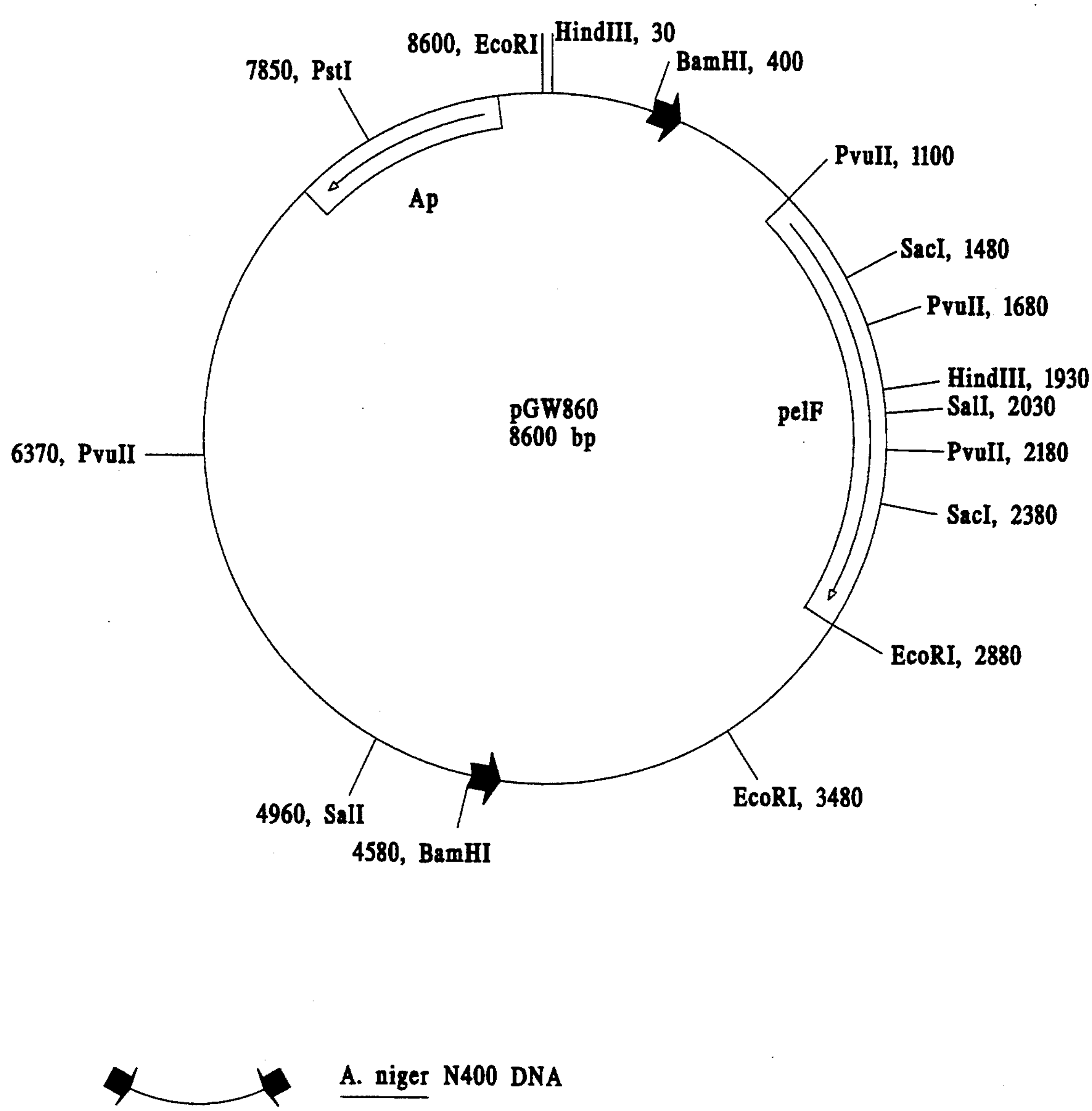
FIG. 14 shows the restriction map of pGW860 containing the pelF gene

Construction of plasmid pUC19/pelA-IFN AM119 (see FIG. 14)

Plasmid pUC19/pelA is digested with SalI. The sticky ends of the linear fragment are filled in a reaction with Klenow DNA polymerase I (BRL) in the presence of 0.1 mM each of dCTP, dGTP, dATP, dTTP, 60 mM Tris.HCl pH 7.5, 10 mM $MgCl_2$ for 30 min at room temperature. The reaction is stopped by the addition of EDTA to a final concentration of 12.5 mM. The DNA is ethanol precipitated. The linear DNA fragment is digested with PstI. After phenol/chloroform extraction the DNA is precipitated with ethanol.

An oligodesoxynucleotide linker shown under SEQ ID No. 16 is ligated to the PstI site of the linearized plasmid. The linker fills the 3' recessed end of the PstI site which coincides with the end of the pelA signal sequence and establishes the inframe fusion to the coding sequence of interferon BDBB. (I) represents the 5' terminal nucleotide sequence of the interferon BDBB gene up to the DdeI restriction site.

200 pmoles of each of the strands of the linker with SEQ ID No. 16 are phosphorylated and annealed. The PstI cut pUC19/pelA plasmid and a 100-fold molar excess of the double-stranded linker DNA are ligated in 60 mM Tris.HCl pH 7.5, 10 mM $MgCl_2$, 1 mM ATP, 5 mM DTT and 400 units of T4 DNA ligase for 16 hours at 15° C. The DNA ligase is inactivated for 10 min at 85° C. The excess linkers are removed by precipitation in the presence of 10 mM EDTA, 300 mM sodium acetate pH 6.0 and 0.54 volumes of isopropanol.

The large, 5 kb fragment is isolated on a preparative 0.6% agarose gel. The fragment comprises the pelA promoter and signal sequence (BamHI[PstI]/linker) and the pelA terminator ([SalI]blunt-HindIII) in vector pUC19.

Plasmid pJDB207/PHO5-IFN AM119 (EP 205404) contains the gene for hybrid α-interferon BDBB under the control of the regulated promoter of the yeast acid phosphatase (PHO5). The plasmid DNA is digested with BamHI and HindIII, The 1.3 kb BamHI-HindIII fragment is isolated, which contains the PHO5 promoter, the coding sequence of IFN BDBB and the PHO5 transcription termination sequences. The fragment is purified by DE52 chromatography and ethanol precipitation and is further digested with TaqI. The sticky ends of the TaqI restriction fragments are filled in a reaction with Klenow DNA Polymerase I (BRL) in the presence of 0.1 mM each of dCTP and dGTP, 60 mM Tris.HCl pH 7.5, 10 mM $MgCl_2$ for 30 min at room temperature. The reaction is stopped by the addition of EDTA to a final concentration of 12.5 mM. The DNA fragments are ethanol precipitated and further digested with DdeI. The DNA fragments are separated on a preparative 0.8% agarose gel. The 549 bp DdeI-[TaqI]-blunt fragment is electroeluted from the gel, purified by DE52 ion exchange chromatography and ethanol precipitation. The DNA fragment is resuspended in $H_2O$ at a concentration of about 0.1 pmoles/μl.

0.2 pmoles of the 549 bp DdeI-[TaqI]blunt fragment and 0.1 pmoles of the 5 kb vector fragment are ligated in 10 μl of 60 mM Tris.HCl pH 7.5, 10 mM $MgCl_2$, 3.5 mM ATP, 5 mM DTT and 200 units of T4 DNA ligase (Biolabs) for 16 hours at 15° C. An 1 μl aliquot of the ligation mixture is used to transform $Ca^{2+}$ treated, competent HB101 cells.

Plasmid DNA is prepared from 12 ampicillin-resistant transformed colonies and analysed by EcoRI, PvuII, ClaI and EcoRI/HindIII digestion. A clone with the expected restriction pattern is selected. The correct in frame fusion of the pelA signal sequence and the mature coding sequence of interferon BDBB is verified by DNA sequencing. The plasmid DNA of the selected clone is referred to as pUC19/pelA-IFN AM119.

An analogous construction with pUC18/pelA results in plasmid pUC18/pelA-IFN AM119.

EXAMPLE 18.2.2

Cotransformation of *Aspergillus niger* mutant An8 with pCG59D7 and pUC19/pelA-IFN AM119

The uridine anxotrophic mutant An8 (=DSM 3917) is transformed with plasmid pCG59D7 to yield uridine prototrophs. Together with the transforming plasmid the non-selective plasmid pUC19/pelA-IFN AM119 is added to give random cointegrants upon cotransformation.

Conidial spores of *A. niger* An8 are grown for 4 days at 28° C. in complete medium until fully sporulated. $2\cdot10^8$ conidiospora are used to inoculate 200 ml minimal medium supplemented with 1 g/l arginine and uridine.

After 20 hours growth at 28° C. and 180 rpm. the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm.) until maximum protoplast release can be detected microscopically (90–120 min). The protoplast suspension is filtrated through a glass wool plug in a funnel to remove mycelial debris. The protoplasts are pelleted by mild centrifugation (10 min, 2000 r.p.m.) at room temperature and washed twice with 10 ml 0.8M KCl, 50 mM CaCl. The protoplasts are finally resuspended in 200–500 μl 0.8M KCl, 50 mM $CaCl_2$ to give a concentration of $1\times10^8$/ml.

For transformation a 200 μl aliquot of the protoplast dispersion is incubated with 5 μg of pCG59D7 and 10 μg pUC19/pelA-IFN AM119 DNA, 50 μl PCT (10 mM Tris.HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with lignified minimal agar medium (Minimal medium+1 g/l arginine+10 g/l Bacto-Agar (Difco)), stabilised with 0.8M KCl. The mixtures are immediately poured on agar plates of the same medium and incubated at 28° C.

After 2–3 days of growth at 28° C., stable transformants appear as vigorously growing and sporulating colonies on a background growth of many hundred small presumably abortive transformants.

EXAMPLE 18.2.3

Expression of the Hybrid-Interferon BDBB gene under the control of the pelA promoter 37 transformants of the cotransformation experiment (Example 18.2.2.) are picked and analysed for interferon expression. Interferon activity is determined according to the procedure of Armstrong. (J. A. Armstrong, Appl. Microbiol. 21, 732 (1971)) using human CCL-23 cells and vesicular stomatitis virus (VSV) as the challenge virus.

Conidial spores from transformants are individually precultured into 50 ml of a preculture medium (Pectin Slow Set L (Unipectin, SA, Redon, France) 3 g/l, $NH_4Cl$ 2 g/l, $KH_2PO_4$ 0.5 g/l, NaCl 0.5 g/l, $Mg_2SO_4\times7H_2O$ 0.5 g/l, $Ca_2SO_4\times2H_2O$ 0.5 g/l, pH 7,0). The preculture is incubated for 72 hours at 250 rpm and 28° C. 10% of the preculture is used to inoculate 50 ml of main culture medium (Soybean fluor 20 g/l, pectin Slow Set 5 g/l). The culture is grown up for 72–96 hours at 250 rpm and 28° C. At various times (every 20 hours) samples are taken, the cells are pelleted by centrifugation and broken by ultrasonic desintegration. Supernatant and cell extracts are both tested for interferon activity as described (supra). The bulk of the interferon activity is found secreted into the medium.

EXAMPLE 19

Construction of plasmid M13(+)KS/pelAΔss-IFN AM119

The 2.8 kb expression cassette of plasmid M13(+)KS/pelAΔss-IFN AM119 comprises the inducible pelA promoter, the coding sequence of hybrid interferon BDBB and the pelA transcriptional terminator on the Bluescript M13(+)KS vector. Hybrid interferon BDBB will be expressed and located in the host cell. Plasmid M13(+)KS/pelAΔss-IFN AM119 is derived from pUC18/pelA-IFN AM119 (see Example 18.2.1). The pelA signal sequence (ss) is looped out by site-directed mutagenesis (see FIG. 20). Hybrid interferon expressed from the construct without signal sequence is expected to be located in the cytosol.

EXAMPLE 19.1

Subcloning of the pelA-IFN AM119 cassette into the Bluescript M13(+)KS vector

Plasmid pUC18/pelA-IFN AM119 (see Example 18.2.1.) is digested with BamHI and HindIII. The 2.8 kb BamHI-HindIII fragment contains the pelA promoter, signal sequence, the IFN BDBB coding sequence and the pelA terminator. The BamHI-HindIII fragment is isolated and ligated to the Bluescript M13(+)KS (Stratagene) vector, cut with BamHI and HindIII. An aliquot of the ligation mixture is used to transform $Ca^{2+}$ treated, competent JM109 cells. Successfull cloning of the 2.8 kb BamHI-HindIII fragment into M13(+)KS is selected for on ampicillin plates in the presence of X-Gal and IPTG. 12 white, ampicillin resistant colonies are picked. Plasmid DNA of these colonies is analysed by BamHI/BglII double digestion. One transformant with the correct insert is referred to as M13(+)KS/pelA-IFN AM119.

EXAMPLE 19.2

Recovery of single stranded DNA from cells containing the Bluescript M13(+)KS plasmid Plasmid M13(+)KS/pelA-IFN AM119 is used to transform competent E. Coli strain CJ236 (dut-1,ung-1, thi-1, relA-1;pCJ105($Cm^r$); BIO-RAD Muta-Gene M13 in vitro mutagenesis kit). This strain allows incorporation of uracil into the DNA. CJ236 is grown in 10 ml of LB medium containing 100 mg/l of ampicillin. At an $OD_{600}$ of 0.5 the cells are superinfected with phage M13K07 (Mead et al. ref. 29) at a multiplicity of infection of 50. After one hour at 37° C. kanamycin (50 mg/l) is added and the culture is incubated at 37° C. on a shaker for 5 to 6 hours. The non-coding strand with respect to the pelA-IFN AM119 insert of plasmid M13(+)KS/pelA-IFN AM119 is synthesized, packaged and released to the medium. Single stranded DNA is prepared from the culture supernatant according to Kunkel et al. (ref. 30).

EXAMPLE 19.3

Site-directed oligonucleotide mutagenesis on the single stranded DNA template

Figure 20:
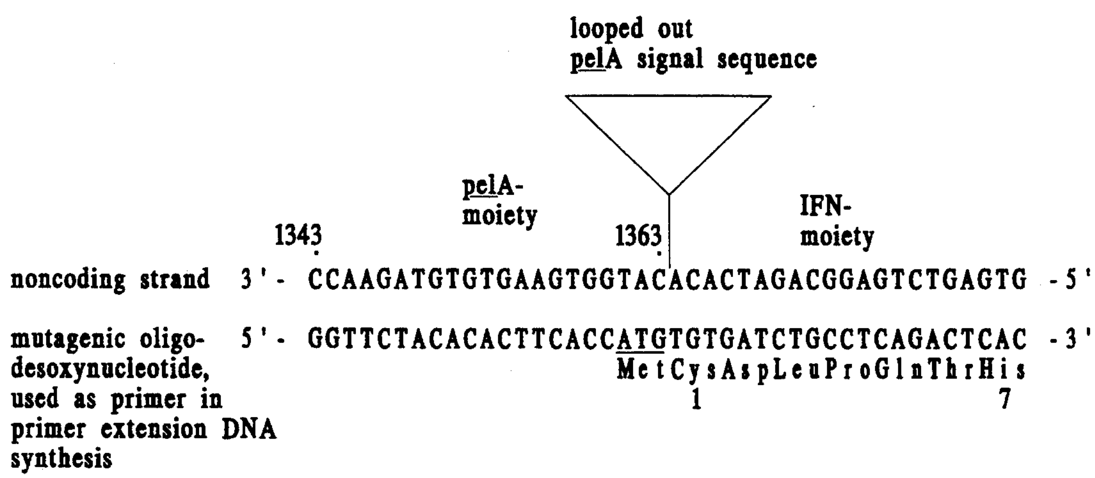
FIG. 20 shows the noncoding strand of part of the pelA-IFN fusion on plasmid pelA-IFN AM119 (SEQ ID NO:17) with looped out signal sequence aligned with the oligonucleotide primer (SEQ ID NO: 18; translation provided as SEQ ID NO: 19) used for deletion mutagenesis of the pelA signal sequence The following examples serve to illustrate the invention, however are in no way intended to restrict it.

Site-directed deletion mutagenesis is performed on the non-coding single stranded pelA-IFN AM119 template to loop out the pelA signal sequence (FIG. 20).

The mutagenic primer comprises part of the pelA promoter sequence including the ATG (nucleotide position 1343 to 1363 in FIG. 10) and 21 nucleotides coding for amino acids 1 to 7 of mature IFN BDBB.

For the mutagenesis 200 pmoles of the mutagenic primer are phosphorylated in 20 μl of 50 mM Tris.HCl pH 7.5, 10 mM $MgCl_2$, 5 mM DTT and 0.5 mM ATP using 8 units of $T_4$ polynucleotide kinase (Boehringer). After one hour at 37° C. the reaction is stopped by heating to 65° for 10 min.

0.2 pmoles of single stranded template is incubated with 10 pmoles of phosphorylated mutagenic oligodeoxyribonucleotide primer and 10 pmoles of universal M13 sequencing primer in 30 μl of 20 mM Tris. HCl pH 7.5, 10 mM $MgCl_2$, 50 mM NaCl, 1 mM DTT at 80° C. for 5 min. The solution is allowed to cool slowly to room temperature over a period of 30 min. To the annealed mixture 10 μl of enzyme-dNTP (dATP,dGTP,dCTP,dTTP) solution are added containing 1 μl of buffer [0.2M Tris. HCl pH 7.5, 0.1M $MgCl_2$], 5 μl of 2 mM dNTP mixture, 0.5 μl of 20 mM ATP, 1 μl of 0.2M DTT, 0.5 μl of $T_4$ DNA ligase (Biolabs, 400 U/μl) and 1.2 μl of Klenow DNA polymerase (BRL, 5 U/μl). The mixture is incubated at 15° C. for 16 hours. The reaction is stopped by incubating at 65° C. for 10 min.

1 μl and 3 μl of the ligation mixture are used to transform 0.2 ml of competent cells of the repair-minus strain *E. coli* MV1190 [Δ(lac-proAB), thi, supE, Δ(srl-recA)306::Tn10($tet^r$) (F':traD36, proAB, lac $I^qZ\Delta M15$)]. Strain MV1190 is described in the manual for the BIO-RAD MUTA-GENE M13 in vitro mutagenesis kit. 12 ampicillin resistant colonies are picked. Plasmid DNA is prepared and analysed by ScaI digestion. Successful loop-out of the pelA signal sequence removes a ScaI site. Correct plasmids are linearized at the ScaI site in the Bluescript vector. One plasmid is further analysed. The correct junction between the pelA promoter and the coding sequence for hybrid IFN BDBB with the ATG included is confirmed by DNA sequencing. One correct construct is referred to as M13(+)KS/pelAΔss-IFN AM119.

EXAMPLE 19.4

Cotransformation of *A. niger* and expression of hybrid interferon

Plasmids M13(+)KS/pelAΔss-IFN AM119 and pCG59D7 are used to cotransform *A. niger* mutant An8 according to Example 17.2.2. Transformants are cultivated as described in Example 17.2.3. At various times (every 20 hours) samples are taken, the cells are pelleted by centrifugation and broken by ultrasonic desintegration. The cell extracts are tested for interferon activity (supra). The bulk of the interferon activity is found intracellularly.

Deposition of Microorganisms

The following microorganisms were deposited under the Budapest Treaty with Deutsche Sammlung yon Mikroorganismen, Mascheroder Weg 1b, D-3300 Braunschweig:

| Microorganisms | Dep. Nr. | Date of Dep. |
|---|---|---|
| *Escherichia coli* BJ5183/pCG3B11 | DSM 3916 | December 11, 1986 |
| *Aspergillus niger* An8 | DSM 3917 | December 11, 1986 |
| *Escherichia coli* BJ5183/pCG59D7 | DSM 3968 | February 2, 1987 |
| *Escherichia coli* HB 101/pGW 820 | DSM 4388 | February 1, 1988 |
| *Escherichia coli* HB 101/pGW 830 | DSM 4389 | February 1, 1988 |
| *Escherichia coli* HB 101/pGW 850 | DSM 4390 | February 1, 1988 |
| *Escherichia coli* HB 101/pGW 860 | DSM 4391 | February 1, 1988 |
| *Escherichia coli* HB 101/pGW 880 | DSM 4392 | February 1, 1988 |

REFERENCES

1. Yelton, M. M., Hamer, J. E. and Timberlake, W. E. (1984 Proc. Natl. Acad. Sci. USA 81, 1470–1474.
2. Frischauf, A. M., Lehrach, H., Poustra, A. and Murray, N. (1983) J. Mol. Biol. 170, 827–842.
3. Karn, J., Brenner, S., Barneff, L. and Cesareni, G. (1980) Proc. Natl. Acad. Sci. USA 77, 5172–5176.
4. Benton, W. D. and Davis, R. W. (1977) Science 196, 180–182.
5. Maniatis, T., Fritsch, E. F. and Sambrook, J. (1982) in: Molecular cloning, a laboratory manual, Cold Spring Harbor Harbor, New York.
6. BRL. M13 cloning/dideoxy sequencing instruction manual.
7. Dente, L., Cesareni, G. and Cortese, R. (1983) Nucl. Acids Res. 11, 1645–1655.
8. Dente, L., Sollazzo, M., Baldari, C., G. Cesareni and R. Cortese. in: DNA Cloning vol. 1. a practical approach ed. D. M. Glover, IRL Press, Oxford 1985.
9. Russell, M., Kidd, S. and Kelley, M. R. (1986) Gene 4–5, 333–338.
10. Caruther, M. H. Chemical and Enzymatic Synthesis of Gene Fragments: a laboratory manual, Verlag Chemie (1982).
11. Ballance, D. J. (1986) Yeast 2, 229–236.
12. Goosen, T., Bloemheuvel, G., Gysler, Ch., de Bier, D. A., van den Broek, H. W. J. and Swart, K. (1987) Current Genetics 11, 499–503.
13. Boeke, J. D., Lacroute, F. and Fink, G. R. (1984) Mol. Gen. Genet. 197, 345–346.
14. Slater, R. J. (1984) in: Methods in Molecular Biology vol. 2 Ed. J. M. Walker, The Humana Press Inc.

14a. Hinnen A., Hicks J. B. & Fink G. R. (1978) Proc. Natl. Acad. Sci. USA 75, 1929–1933.

15. Laemmli, U. K. (1970) Nature 227, 681–682.
16. Towbin, H., Staehelin, T. and Gordon, J. (1979) Proc. Natl. Acad. Sci. USA 76, 4350–4354.
17. Ried, J. L. and Collmer, A. (1985) Applied and Environm. Microbiol. 50, 615–622.
18. F. E. A. van Houdenhoven. Ph.D. Thesius Agricultural University, Wageningen in Communications Agricultural University Wageningen, The Netherlands 75–13 (1975).
19. Hunkapiller, M. W. (1985) PTH Amino Acid Analysis, User Bulletin no. 14 Applied Biosystems.
20. Zissler, J. et al. (1971) in: The Bacteriophage Lambda, Cold Spring Harbor Labs, New York, A. D. Hersley editor.
21. Norrander, J., Kempe, T. and Messing, J. (1983) Gene 2–6, 101–106.
22. F. E. A. von Houdenhoven. Ph.D. Thesius Agricultural University, Wageningen in Communications Agricultural University Wageningen, The Netherlands 75–13 (1975).
23. Birnboim H. C. & Doly J. (1979). Nucleic Acids Res 7, 1513–1523.
24. Boel E., Hansen M. T., Hjort I., Hoegh I., Fiil N. P. (1984). EMBO J. 3, 1581–1585.
25. Mount S. M. (1982). Nucleic Acids Res.10. 459–472.
26. Ballance D. J. and Turner G. (1985), Gene 36, 321–331.
27. Hermersdörfer H, Leuchtenberger A, Wardsack Ch and Ruttloff H (1907) Influence of culture conditions on mycelial structure and polygalacturonase synthesis of *A. niger*. J. Basic Microbiol. 27, 309–315.
28. Henikoff, S. (1984) Gerne 28, 351–359.
29. Mead et al., (1986) Protein Engeneering 1, 67.
30. Kunkel et al., (1985) Proc. Natl. Acad. Sci. USA 82,485.
31. Edman P., and Begg G. (1967) Eur. J. Biochem. 1, 80–91.
32. J. M. Vereijken, J. Hofsteenge, H. J. Bak and J. J. Beintema. Eur. J. Biochem. 113, 151 (1980).
33. G. Frank and W. Strubert. Chromatographia 6, 522 (1973).
34. A. M. Crestfield, S. Moore and W. H. Stein. J. Biol. Chem. 238, 622 (1963).
35. Knecht et al., Anal. Biochem. 130, 65 (1983).
36. Nilsson B., Uhlen M., Josephson S., Gatenbeck S. and Philipson L. (1983). Nucleic Acids Research 11, 8019–8030.
37. Hanahan D., (1983). J. Mol. Biol. 166, 557–580.
38. Gergen J. P., Stern R. H., Wensink P. C. (1979). Nucleic Acids Research 7, 2115–2136.
39. Humphreys G. O., Willshaw G. A., Anderson E. S. (1975). Biochimica et Biophysica Acta, 383, 457–463.
40. Messing J. (1983), Methods in Enzymology 101, 21–78.
41. M13 cloning and sequencing handbook, Amersham International plc. Buckinghamshire, England
42. Zoller M. J. & Smith M. (1984). DNA 3, 479–488.
43. Itakura et al., J. Am. Chem. Soc. 103, 706 (1981).
44. Holmes D. S., Quigley M. (1981). Anal Biochem 114, 193–197.
45. Sanger T., Nickler S., Coulson A. R. (1977). Proc. Natl. Acad. Sci. USA 74, 5463–5467.
46. Bolivar F., Rodriguez R. L., Greene P. J., Betlach M. C., Heineker H. L., Boyer H., Crosa J. H., Falkow S. (1977). Gene 2, 95–113.
47. Yanish-Perron C., Vieira J., Messing J. (1984). Submitted to Gene.

What is claimed is:

1. A recombinant DNA molecule comprising an expression cassette, said expression cassette comprising a *Aspergillus niger* DNA sequence selected from the group of sequences consisting of: a promoter of pectin lyase pelA, pelB, pelC, pelE, pelF, or pelD; a terminator of pectin lyase pelA, pelD, pelC, pelE, pelF, or pelD; a DNA sequence coding for the signal peptide of pectin lyase PLA, PLB, PLC, PLD, PLE or PLF; and a DNA sequence coding for pectin lyase PLA, PLB, PLC, PLD, PLE or PLF.

2. A recombinant DNA molecule of claim 1, wherein said promoter is the pelA promoter.

3. A recombinant DNA molecule of claim 1, wherein said promoter is the pelD promoter.

4. A recombinant DNA molecule of claim 1, wherein said *Aspergillus niger* DNA sequence is from a structural gene selected from the group consisting of the structural genes of pelA, pelB, pelC, pelE, pelF and pelD.

5. A recombinant DNA molecule of claim 1, wherein said *Aspergillus niger* DNA sequence is from a structural gene selected from the group consisting of the structural genes of pelA, pelB, pelC, pelE, pelF and pelD without introns.

6. A recombinant DNA molecule of claim 1, comprising a DNA sequence selected from the group of DNA sequences encoding the pectin lyases PLA, PLB, PLC, PLD, PLE and PLF, respectively.

7. A recombinant DNA molecule of claim 1, comprising a DNA sequence selected from the group consisting of an Aspergillus pectin lyase structural gene, a pectin lyase promoter, a pectin lyase terminator and a pectin lyase signal sequence which is SEQ ID No. 1.

8. A recombinant DNA molecule of claim 1, comprising a DNA sequence selected from the group consisting of an Aspergillus pectin lyase structural gene, a pectin lyase promoter, a pectin lyase terminator and a pectin lyase signal sequence which is SEQ ID No. 2.

9. A recombinant DNA molecule of claim 1, comprising a DNA sequence selected from the group consisting of an Aspergillus pectin lyase structural gene, a pectin lyase promoter, a pectin lyase terminator and a pectin lyase signal sequence which is SEQ ID No. 3.

10. A recombinant DNA molecule of claim 1, comprising a DNA sequence selected from the group consisting of an Aspergillus pectin lyase structural gene, a pectin lyase promoter, a pectin lyase terminator and a pectin lyase signal sequence which is SEQ ID No. 4.

11. A purified *Aspergillus niger* DNA molecule selected from the group consisting of: a promoter of pectin lyase pelA, pelB, pelC, pelE, pelF, or pelD; a terminator of pectin lyase pelA, pelB, pelC, pelE, pelF, or pelD; a DNA sequence coding for the signal peptide of pectin lyase PLA, PLY, PLC, PLD, PLE or PLF; and a DNA sequence coding for pectin lyase PLA, PLB, PLC, PLD, PLE or PLF.

12. A purified DNA molecule of claim 11, wherein said promoter is the pelA promoter.

13. A purified DNA molecule of claim 11, wherein said promoter is the pelD promoter.

14. A purified DNA molecule of claim 11, wherein said *Aspergillus niger* DNA sequence is from a structural gene selected from the group consisting of the structural genes pelA, pelB, pelC, pelE, pelF and pelD, 15. A purified DNA molecule of claim 11, wherein said *Aspergillus niger* DNA sequence is from a structural gene selected from the group consisting of the structural genes pelA, pelB, pelC, pelE, pelF and pelD without introns.

16. A purified DNA molecule of claim 11, which encodes a pectin lyase selected from the group consisting of PLA, PLB, PLC, PLD, PLE and PLF.

17. A purified DNA molecule of claim 11, selected from the group consisting of an Aspergillus pectin lyase structural gene, a pectin lyase promoter, a pectin lyase terminator, and a pectin lyase signal sequence which is SEQ ID No. 1.

18. A purified DNA molecule of claim 11, selected from the group consisting of an Aspergillus pectin lyase structural gene, a pectin lyase promoter, a pectin lyase terminator and a pectin lyase signal sequence which is SEQ ID No. 2.

19. A purified DNA molecule of claim 11, selected from the group consisting of an Aspergillus pectin lyase structural gene, a pectin lyase promoter, a pectin lyase terminator and a pectin lyase signal sequence which is SEQ ID No. 3.

20. A purified DNA molecule of claim 11, selected from the group consisting of an Aspergillus pectin lyase structural gene, a pectin lyase promoter, a pectin lyase terminator and a pectin lyase signal sequence which is SEQ ID No. 4.

21. A recombinant DNA molecule of claim 1, which pCG3B11 or pGW840.

22. A recombinant DNA molecule of claim 1, which is pGW820.

23. A recombinant DNA molecule of claim 1, which is pGW830.

24. A recombinant DNA molecule of claim 1, which is pGW850.

25. A recombinant DNA molecule of claim 1, which is pGW880.

26. A recombinant DNA molecule of claim 1, which is pGW860.

27. A recombinant DNA molecule of claim 1, which comprises a fragment extending between two restriction sites of plasmids pCG3B11, pBS820, pGW830, pGW840, pGW850, pGW880 or pGW860, said fragment retaining a promoter, signal, structural or terminator function, or a combination of said fragments.

28. A recombinant DNA molecule of claim 1, which is a recombinant hybrid vector.

29. A vector of claim 28, comprising the marker gene pyrA.

30. A vector of claim 28, comprising a structural gene heterologous to *Aspergillus niger.*

31. A vector of claim 30, wherein said heterologous gene comprises a gene encoding the hybrid interferon BDBB.

32. A vector of claim 30, which is pUC19/pelA-IFN AM119.

33. A vector of claim 30, which is M13(+)KkS/pelA6ss-IFN AM119.

34. A vector of claim 30, which is M13(+)KS/pelA-IFN AM119.

35. A vector of claim 1, comprising a structural gene selected from the group consisting of the structural genes encoding PLD, PLA, PLB, PLC, PLE and PLF, respectively.

36. A vector of claim 35, which pLHL5.

37. A vector of claim 35, which is pLHLT7.

38. A host transformed with a recombinant DNA molecule of claim 1.

39. A host of claim 101, which is *E. coli* BJ5183/pG3B11 (DSM 3916).

40. A host of claim 38, which is *E. coli* HB 101/pGW820 (DSM 4388).

41. A host of claim 38, which is *E. coli* HB 101/pGW830 (DSM 4389).

42. A host of claim 38, which is *E. coli* HB 101/pGW850 (DSM 4390).

43. A host of claim 38, which is *E. coli* HB 101/pGW860 (DSM 4391).

44. A host of claim 38, which is *E. coli* HB 101/pGW880 (DSM 4392).

45. A host of claim 38, which is *A. niger* An8(DSM 3917), further transformed with the selection marker plasmid pCG59D7.

46. A host of claim 38, which is *A. niger* An8(DSM 3917), transformed with pLHK3, pLHL5 or PLHLT7, and the selection marker plasmid pCG59D7.

47. A host of claim 38, transformed with pUC19-/pelA-IFN AM119 and the selection marker plasmid pCG59D7.

48. A host of claim 38, which is *A. niger* An8 (DSM 3917), transformed with M13 (+)KS/pelA6ss-IFN AM119 and the selection marker plasmid pCG59D7.

49. A host of claim 38, which is *A. niger* An8(DSM 3917), transformed with M13(+)KS/pelA-IFN AM119 and the selection marker plasmid pCG59D7.

* * * * *

SEQUENCE LISTING ( 1 ) GENERAL INFORMATION:

( i i i ) NUMBER OF SEQUENCES: 19

-continued ( 2 ) INFORMATION FOR SEQ ID NO:1:

( i ) SEQUENCE CHARACTERISTICS:
( A ) LENGTH: 2717 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Aspergillus niger N756

( v i i ) IMMEDIATE SOURCE:
( B ) CLONE: Plasmid pCG3B11 (DSM 3916)

( i x ) FEATURE:
( A ) NAME/KEY: CDS
( B ) LOCATION: join(689..889, 955..1098, 1161..1286, 1350..1445, 1503..2054)
( D ) OTHER INFORMATION: /transl_except=(pos: 1096 .. 1098, aa: Tyr)

( i x ) FEATURE:
( A ) NAME/KEY: sig_peptide
( B ) LOCATION: 689..746

( i x ) FEATURE:
( A ) NAME/KEY: exon
( B ) LOCATION: 747..889

( i x ) FEATURE:
( A ) NAME/KEY: intron
( B ) LOCATION: 890..954

( i x ) FEATURE:
( A ) NAME/KEY: exon
( B ) LOCATION: 955..1097

( i x ) FEATURE:
( A ) NAME/KEY: intron
( B ) LOCATION: 1098..1159

( i x ) FEATURE:
( A ) NAME/KEY: exon
( B ) LOCATION: 1160..1286

( i x ) FEATURE:
( A ) NAME/KEY: intron
( B ) LOCATION: 1287..1349

( i x ) FEATURE:
( A ) NAME/KEY: exon
( B ) LOCATION: 1350..1445

( i x ) FEATURE:
( A ) NAME/KEY: intron
( B ) LOCATION: 1446..1502

( i x ) FEATURE:
( A ) NAME/KEY: exon
( B ) LOCATION: 1503..2054

( i x ) FEATURE:
( A ) NAME/KEY: promoter
( B ) LOCATION: 1..688

( i x ) FEATURE:
( A ) NAME/KEY: terminator
( B ) LOCATION: 2058..2717

( x i ) SEQUENCE DESCRIPTION: SEQ ID NO:1:

ACTAGTAGTC TAATCGCTAC AAAGTGCATC AGGGGAGCCA GCCATGGGAA CAAAGCTCGA 60

TGCAATCTGA CTTAATCAGT CTCCACATCG AGCTGGGCGT GAAACTGATG GACACTCCGC 120

CATCTACTCG AAACCATCTC TAATTAAGCA CTCACGGCTC CACTTCTTCT CTGGGCTTCC 180

TCCGTGCCGC TCGGACAGCT CACTGGATGC TCCCAGTGGA GTCGTTTCAC CGGATCCCCT 240

-continued

```
CAACGCTGAC GATCGCATTC CCAAGGCATC CACTAGCTCT CTCAAGCAGA CCAGGGCAGT    300

GAGGTGATCG GCGGTGGCCT CACGAGTCAC GACATTACTG TCGCCGGGAC CCAGATGTTT    360

ATTCTCCCTC CCTGTCGACC TAATGGCCCA CACCACATCC ACCGTCATAA CGCCGATATT    420

GGTCGAGATT GCGCTGGAGT CGCAGAGGGA GTCTTCGGCA TACCCACCGG CTCCGTAAAC    480

CTCCATCAGG AGAATTGTTC CAAACTTCCA TGAGCCATGG CTTCGAGGAC CACAGCCCTC    540

TATATAAGGG ACGAGCCCGT CGACCGTCTC GGATCCTTTC CTCTCTGGCT CAACACACAC    600

AACTTTGTCA TTCTTTCTCT TGTTTCTCTT TTGTTTCTAA TTGTAACCTT TGTCACTCTT    660

TTCTAAACCG ACTTGCAAAA CTTCCAGG ATG AAG TAC GCT GCT GCT CTC ACG    712
                               Met Lys Tyr Ala Ala Ala Leu Thr
                                1               5

GCT ATT GCC GCC CTC GCT GCC CGC GCC GCT GCT GTC GGT GTC TCC GGC    760
Ala Ile Ala Ala Leu Ala Ala Arg Ala Ala Ala Val Gly Val Ser Gly
     10                  15                  20

ACT CCC GTG GGT TTC GCC TCC TCC GCC ACT GGT GGT GGT GAT GCT ACC    808
Thr Pro Val Gly Phe Ala Ser Ser Ala Thr Gly Gly Gly Asp Ala Thr
 25                  30                  35                  40

CCC GTC TAC CCT ACC ACC ACC GAT GAG CTG GTC TCT TAC CTC GGT GAT    856
Pro Val Tyr Pro Thr Thr Thr Asp Glu Leu Val Ser Tyr Leu Gly Asp
                 45                  50                  55

GAC GAG GCC CGT GTC ATT GTC CTG TCC AAG ACG TGAGTTTTGA ATCCAAAGCA    909
Asp Glu Ala Arg Val Ile Val Leu Ser Lys Thr
             60                  65

ATGAACGAAT CGATTCCCGG CTGACCAGTG TCCGAATTTG CCAGT TTC GAC TTC    963
                                                   Phe Asp Phe
                                                            70

ACT GAC ACT GAG GGC ACT ACC ACG ACC ACC GGT TGC GCT CCC TGG GGT   1011
Thr Asp Thr Glu Gly Thr Thr Thr Thr Thr Gly Cys Ala Pro Trp Gly
                 75                  80                  85

ACT GCC TCC GGC TGC CAG CTG GCC ATC AAC AAG GAC GAC TGG TGC ACC   1059
Thr Ala Ser Gly Cys Gln Leu Ala Ile Asn Lys Asp Asp Trp Cys Thr
             90                  95                 100

AAC TAC GAG CCC GAT GCT CCC ACC ACC ACC GTC ACC TAG TAAGTTGCCT   1108
Asn Tyr Glu Pro Asp Ala Pro Thr Thr Thr Val Thr Tyr
        105                 110                 115

TCTGAGGTAT CCTCGAGTAT CAAGGAAGAG GAAATGCTGA CAAGAGGATA GC AAC   1163
                                                         Asn

ACT GCT GGT GAA CTC GGT ATC ACC GTC AAC TCC AAC AAG TCC TTG ATC   1211
Thr Ala Gly Glu Leu Gly Ile Thr Val Asn Ser Asn Lys Ser Leu Ile
            120                 125                 130

GGT GAG GGT ACC AGC GGT GTC ATC AAG GGC CGT GGT CTC CGC ATG GTC   1259
Gly Glu Gly Thr Ser Gly Val Ile Lys Gly Arg Gly Leu Arg Met Val
        135                 140                 145

AGC GGT GTC TCC AAC ATC ATC ATC CAG TATGCATCGT CCAGGACTAC   1306
Ser Gly Val Ser Asn Ile Ile Ile Gln
    150                 155

ATACATTACT CCCATCGCAA ACTAACCATG GAATTCCCAC AGG AAC ATT GCT GTC   1361
                                                Asn Ile Ala Val
                                                        160

ACC GAC ATC AAC CCC GAG TAC GTC TGG GGT GGT GAC GCC ATC ACC CTC   1409
Thr Asp Ile Asn Pro Glu Tyr Val Trp Gly Gly Asp Ala Ile Thr Leu
            165                 170                 175

GAC GAG GCT GAC TTG GTC TGG ATT GAC CAC GTT ACT GTAAGTCGCC   1455
Asp Glu Ala Asp Leu Val Trp Ile Asp His Val Thr
        180                 185

ATCCAGCATC ATGATTTTCA TCCTTCCACC ACTAATGAAT GCTTCAG ACT GCC CGC   1511
                                                     Thr Ala Arg
                                                     190

ATT GGT CGC CAG CAC TAC GTC CTC GGT ACC GAC GCC GAC AGC CGT GTC   1559
```

-continued

```
Ile Gly Arg Gln His Tyr Val Leu Gly Thr Asp Ala Asp Ser Arg Val
        195                 200                 205

TCC ATC ACC AAC AAC TAC ATC AAC GGC GAG TCT GAC TAC TCT GCT ACT    1607
Ser Ile Thr Asn Asn Tyr Ile Asn Gly Glu Ser Asp Tyr Ser Ala Thr
    210                 215                 220

TGC GAC GGC CAC CAC TAC TGG AAC GTG TAC CTT GAC GGC TCT AGC GAC    1655
Cys Asp Gly His His Tyr Trp Asn Val Tyr Leu Asp Gly Ser Ser Asp
225                 230                 235                     240

AAG GTC ACC TTC AGT GGC AAC TAC CTG TAC AAG ACC TCC GGC CGT GCC    1703
Lys Val Thr Phe Ser Gly Asn Tyr Leu Tyr Lys Thr Ser Gly Arg Ala
                245                 250                 255

CCC AAG GTC CAG GAC AAC ACC TAC CTC CAC ATC TAC AAC AAC TAC TGG    1751
Pro Lys Val Gln Asp Asn Thr Tyr Leu His Ile Tyr Asn Asn Tyr Trp
            260                 265                 270

GAG AAC AAC TCG GGC CAC GCT TTC GAG ATC GGC TCC GGT GGC TAC GTC    1799
Glu Asn Asn Ser Gly His Ala Phe Glu Ile Gly Ser Gly Gly Tyr Val
        275                 280                 285

CTC GCC GAG GGT AAC TAC TTC TCC AAC GTC GAC ACC GTC CTC GAG ACC    1847
Leu Ala Glu Gly Asn Tyr Phe Ser Asn Val Asp Thr Val Leu Glu Thr
    290                 295                 300

GAC ACC TTC GAG GGT GCT CTC TTC TCC TCT GAC AGC GCC TCC TCC ACC    1895
Asp Thr Phe Glu Gly Ala Leu Phe Ser Ser Asp Ser Ala Ser Ser Thr
305                 310                 315                     320

TGC GAG TCC TAC ATT GGC CGT TCC TGC GTT GCC AAC GTC AAC GGC GGT    1943
Cys Glu Ser Tyr Ile Gly Arg Ser Cys Val Ala Asn Val Asn Gly Gly
                325                 330                 335

GAC CTC ACC GGC ACC TCC ACC ACC GTC CTC TCC AAC CTC AGC GGC GAC    1991
Asp Leu Thr Gly Thr Ser Thr Thr Val Leu Ser Asn Leu Ser Gly Asp
            340                 345                 350

ACC CTC CCC TCT GCT GAT GCT GCC AGC ACC AGC CCC GCC TCC AAC GCT    2039
Thr Leu Pro Ser Ala Asp Ala Ala Ser Thr Ser Pro Ala Ser Asn Ala
        355                 360                 365

GGT CAG GGT AAC CTG TAAGCGGTAT CGCTCCGTCG GGCTCTTACT GCAGATCGCT    2094
Gly Gln Gly Asn Leu
    370

TTGGTGATGT TGTCGAGTTT GATGATTCAG ACAAGACGAG TTGAGTTTTC TCCTGTTGTA    2154

CAGCGGAAAA GTGTGTTCGC TTAGATTCTA TCTTAGCCTA ATCAATAATT CTAAGATGGA    2214

CTTGATCCAT AGTAATTCTC CATTCAATTG TGATTTAGTA AATTTGATTT TCTTTGCCTA    2274

GTCGCGCTTC TAAACTAGGA TCACAGCTGC TCTTAGATCC TCGATGCCCA AGGCCACTAA    2334

CGCTTTCTGC CTCAGGACTC CACAGTCCGA GACGGATGTA CTGCCTGAGG CCTAAGTGTG    2394

CTTCTGCCCA AGGCAACAAT GGGCATGATC ATACATTCAC TATACTTGTG CTCTAAGGAA    2454

TAGTAGGATC GGATGTGAAC CATTATATTT AACTGAGTGA TCTGTGGTCT TTTCATATTT    2514

GCAATGACTT GCTTAACTTA TTTGGCCGTT CTTCCATAGA TGCGATCATG TTCGGTAGAC    2574

TTCAAAAACA TGTGATTGCT GACATATTCT GCCTATTTCT GCTGCAAGGC GTATGAAAAA    2634

TGGCATTCCT GCCGTGGCTA ATGGCCAAAT GCTATGGCAT CACAATACTT TTTCTGCTGG    2694

CTATCACATT GCATCGAGCT AGC                                          2717
```

( 2 ) INFORMATION FOR SEQ ID NO:2:

( i ) SEQUENCE CHARACTERISTICS:
( A ) LENGTH: 373 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Lys Tyr Ala Ala Ala Leu Thr Ala Ile Ala Ala Leu Ala Ala Arg
```

-continued 1 5 10 15

Ala Ala Ala Val Gly Val Ser Gly Thr Pro Val Gly Phe Ala Ser Ser
20 25 30

Ala Thr Gly Gly Gly Asp Ala Thr Pro Val Tyr Pro Thr Thr Thr Asp
35 40 45

Glu Leu Val Ser Tyr Leu Gly Asp Asp Glu Ala Arg Val Ile Val Leu
50 55 60

Ser Lys Thr Phe Asp Phe Thr Asp Thr Glu Gly Thr Thr Thr Thr Thr
65 70 75 80

Gly Cys Ala Pro Trp Gly Thr Ala Ser Gly Cys Gln Leu Ala Ile Asn
85 90 95

Lys Asp Asp Trp Cys Thr Asn Tyr Glu Pro Asp Ala Pro Thr Thr Thr
100 105 110

Val Thr Tyr Asn Thr Ala Gly Glu Leu Gly Ile Thr Val Asn Ser Asn
115 120 125

Lys Ser Leu Ile Gly Glu Gly Thr Ser Gly Val Ile Lys Gly Arg Gly
130 135 140

Leu Arg Met Val Ser Gly Val Ser Asn Ile Ile Ile Gln Asn Ile Ala
145 150 155 160

Val Thr Asp Ile Asn Pro Glu Tyr Val Trp Gly Gly Asp Ala Ile Thr
165 170 175

Leu Asp Glu Ala Asp Leu Val Trp Ile Asp His Val Thr Thr Ala Arg
180 185 190

Ile Gly Arg Gln His Tyr Val Leu Gly Thr Asp Ala Asp Ser Arg Val
195 200 205

Ser Ile Thr Asn Asn Tyr Ile Asn Gly Glu Ser Asp Tyr Ser Ala Thr
210 215 220

Cys Asp Gly His His Tyr Trp Asn Val Tyr Leu Asp Gly Ser Ser Asp
225 230 235 240

Lys Val Thr Phe Ser Gly Asn Tyr Leu Tyr Lys Thr Ser Gly Arg Ala
245 250 255

Pro Lys Val Gln Asp Asn Thr Tyr Leu His Ile Tyr Asn Asn Tyr Trp
260 265 270

Glu Asn Asn Ser Gly His Ala Phe Glu Ile Gly Ser Gly Gly Tyr Val
275 280 285

Leu Ala Glu Gly Asn Tyr Phe Ser Asn Val Asp Thr Val Leu Glu Thr
290 295 300

Asp Thr Phe Glu Gly Ala Leu Phe Ser Ser Asp Ser Ala Ser Ser Thr
305 310 315 320

Cys Glu Ser Tyr Ile Gly Arg Ser Cys Val Ala Asn Val Asn Gly Gly
325 330 335

Asp Leu Thr Gly Thr Ser Thr Thr Val Leu Ser Asn Leu Ser Gly Asp
340 345 350

Thr Leu Pro Ser Ala Asp Ala Ala Ser Thr Ser Pro Ala Ser Asn Ala
355 360 365

Gly Gln Gly Asn Leu
370

( 2 ) INFORMATION FOR SEQ ID NO:3:

( i ) SEQUENCE CHARACTERISTICS:
( A ) LENGTH: 3164 base pairs
( B ) TYPE: nucleic acid
( C ) STRANDEDNESS: double
( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Aspergillus niger N400

( v i i ) IMMEDIATE SOURCE:
( B ) CLONE: Plasmid pGW820 (DSM 4388)

( i x ) FEATURE:
( A ) NAME/KEY: CDS
( B ) LOCATION: join(1361..1708, 1761..1886, 1935..2030, 2095..2328, 2383..2715)
( D ) OTHER INFORMATION: /transl_except=(pos: 1706 .. 1708, aa: Tyr)

( i x ) FEATURE:
( A ) NAME/KEY: sig_peptide
( B ) LOCATION: 1361..1420

( i x ) FEATURE:
( A ) NAME/KEY: exon
( B ) LOCATION: 1421..1707

( i x ) FEATURE:
( A ) NAME/KEY: intron
( B ) LOCATION: 1708..1759

( i x ) FEATURE:
( A ) NAME/KEY: exon
( B ) LOCATION: 1760..1886

( i x ) FEATURE:
( A ) NAME/KEY: intron
( B ) LOCATION: 1887..1934

( i x ) FEATURE:
( A ) NAME/KEY: exon
( B ) LOCATION: 1935..2030

( i x ) FEATURE:
( A ) NAME/KEY: intron
( B ) LOCATION: 2031..2094

( i x ) FEATURE:
( A ) NAME/KEY: exon
( B ) LOCATION: 2095..2328

( i x ) FEATURE:
( A ) NAME/KEY: intron
( B ) LOCATION: 2329..2382

( i x ) FEATURE:
( A ) NAME/KEY: exon
( B ) LOCATION: 2383..2715

( i x ) FEATURE:
( A ) NAME/KEY: promoter
( B ) LOCATION: 1..1360

( i x ) FEATURE:
( A ) NAME/KEY: terminator
( B ) LOCATION: 2719..3164

( x i ) SEQUENCE DESCRIPTION: SEQ ID NO:3:

```
CAGCTGGACC GGAAATATGA TTGATAGGGG CAACGTCACT CCATCTCCCC TGATTCGTGA    60
TAAAAATGAG TTATGATTGA TGCCTACGGA GTCCGAGATA CTCCCACCTT ATCGTGACCA   120
GTCACCCGTT CAGACTGGAT GACAAAATCA TCAGTCAACC AACTAGATCG GTGCTAAAAA   180
TGGACGGCTA AATTTCTGCA CTGGATTCGA AACTCGAGGA GCAATAGCTG CCCGGAGGTC   240
GACTTGATGG GTGGTGTCCT GATATCGCCG AAGCCCGAAG GTTCCACTGT GGGCCACTTG   300
ACCGGCGTTC CTGGCGCCTT ACCAAGAACG CCTAATTCGT GGCTTTTTTC TTTTCTTTTT   360
TTTTTCTTTA CTTTGCGCAG CTTTTCCAGC TGCTCTCATT TGACTAGAAG ACCGACTGGA   420
GATATAGAGA GGCGTGGGGA GATACTGGAT CCATTAATAA TCGAAACGGA AACGGTCTCA   480
```

-continued

```
GGTGGAGGCT AAACCTTTCA AAGAAGCTGG ATTCGTGATG CAAAATTGTT TCCCCCCCGG    540

TTCCCCTCTT GTTCTTCACC ACTGATGAAC AGCCCTAACT GTCGAGCACG TCCAGCCTTC    600

CATCCGTAAC ATCCTCAAAC TACTAGCTAC ACCCTGATGG TCGGATTCGG TATTTTCCCG    660

ACTATCATTG CCACAAGGAC TCTGCCAAGA CGGAGGAATT GCTTCTTTAC AGAATTTCAA    720

TCGCGAGGTC CACCAGCCCG AGTGGATGGA CTAGTTACTT TAGACTACCG TGACTAAGTC    780

GCCGGCGCGG GCATCATGAA ACGCCGTAAA TCCCCCGACT CCCTCCTAAG ATCCACCTAT    840

GACCTTCAAC AGCCTGCAAG ACAGTGGGCT GTCCAGCTCA GTGTCCACGA ACAGGGGCCA    900

TCACCGTGAT GGACAACCAT GTGGCTACGA CTCCTCCCTC CCCCTTCCAA TCTTGGTTGT    960

CATCGATGCC TATCACTCCA TCCATGGTCC GATACGATGG ACCCCCTTCA ATCTACTTGC   1020

TCGGCCAGTA CCGACTTTAG CGCCGGTGGA CTGACCGAGA AGAATCAACG GTTTTGCTCA   1080

ATCGCCCTTG GCTACTAATC AAAGATGCAC TTGGCCGTTT CATACCGATC ACCCGTCCAA   1140

TTTACCCAGA ATGGTCTGAG CCAGAGGGGA AGCTCTATCA GATTCTTGTC AAATGCTTCC   1200

GTCAACGAGT CAGTCTTCCC TATAAAAGGC CCCAATCCCA TCCGTATTGA CCTCTTCTCT   1260

GTATCAAACC ATTCCTTCCT TTTCTTTCCT TTTCTCTTCA TACCTCTATC TTCACCTTAG   1320

TCTTTCTTTC CCCTTCATAG CTGGTTCTAC ACACTTCACC ATG AAG TAC TCT ACT   1375
                                            Met Lys Tyr Ser Thr
                                              1               5

ATC TTC AGC GCT GCT GCC GCT GTT TTC GCT GGT TCC GCC GCT GCA GTC   1423
Ile Phe Ser Ala Ala Ala Ala Val Phe Ala Gly Ser Ala Ala Ala Val
                 10                  15                  20

GGC GTG TCC GGC TCT GCT GAG GGT TTC GCC GAG GGC GTC ACC GGT GGC   1471
Gly Val Ser Gly Ser Ala Glu Gly Phe Ala Glu Gly Val Thr Gly Gly
             25                  30                  35

GGT GAT GCC ACC CCC GTC TAC CCC GAC ACT ATC GAT GAG CTG GTC TCT   1519
Gly Asp Ala Thr Pro Val Tyr Pro Asp Thr Ile Asp Glu Leu Val Ser
         40                  45                  50

TAC CTT GGA GAC GAT GAG GCC CGC GTC ATT GTC CTG ACC AAG ACC TTC   1567
Tyr Leu Gly Asp Asp Glu Ala Arg Val Ile Val Leu Thr Lys Thr Phe
     55                  60                  65

GAC TTC ACC GAC AGC GAA GGT ACC ACC ACT GGC ACT GGT TGC GCT CCC   1615
Asp Phe Thr Asp Ser Glu Gly Thr Thr Thr Gly Thr Gly Cys Ala Pro
 70                  75                  80                  85

TGG GGT ACC GCT TCC GCC TGC CAG GTT GCT ATT GAC CAG GAC GAC TGG   1663
Trp Gly Thr Ala Ser Ala Cys Gln Val Ala Ile Asp Gln Asp Asp Trp
                 90                  95                 100

TGC GAG AAC TAC GAG CCC GAT GCT CCC TCT GTC AGC GTT GAA TAG       1708
Cys Glu Asn Tyr Glu Pro Asp Ala Pro Ser Val Ser Val Glu Tyr
            105                 110                 115

TATGTCCTTG GGGATTGTCA CCCGCTTCGA TCTTGTATCT AACTTGGATA GC TAC     1763
                                                          Tyr

AAC GCT GGT GTC CTC GGT ATC ACC GTC ACC TCC AAC AAG TCC CTC ATC   1811
Asn Ala Gly Val Leu Gly Ile Thr Val Thr Ser Asn Lys Ser Leu Ile
        120                 125                 130

GGT GAG GGC TCC TCT GGT GCA ATC AAG GGC AAG GGT CTC CGT ATT GTC   1859
Gly Glu Gly Ser Ser Gly Ala Ile Lys Gly Lys Gly Leu Arg Ile Val
    135                 140                 145

AGC GGT GCT GAG AAC ATC ATC ATC CAG TAGGTTATGC TCGGTGTCAT         1906
Ser Gly Ala Glu Asn Ile Ile Ile Gln
150                 155

TAGGAATTTG CTCTCTAACG AAATCAGG AAC ATC GCG GTT ACC GAC ATC AAC    1958
                               Asn Ile Ala Val Thr Asp Ile Asn
                                   160                 165

CCC AAG TAC GTC TGG GGT GGT GAT GCT ATT ACT CTT GAT GAC TGC GAC   2006
Pro Lys Tyr Val Trp Gly Gly Asp Ala Ile Thr Leu Asp Asp Cys Asp
```

-continued

```
                170                     175                     180

CTG GTC TGG ATC GAC CAT GTT ACT GTACGTCTTC ATCTTATTCA ACTACTACAT     2060
Leu Val Trp Ile Asp His Val Thr
        185                 190

TATATTTCAA GAGCATTGAG TTAACATATG ACAG ACC GCC CGC ATC GGT CGC        2112
                                      Thr Ala Arg Ile Gly Arg
                                                      195

CAG CAC TAC GTC CTT GGA ACC AGC GCC GAC AAC CGC GTC TCT CTC ACC      2160
Gln His Tyr Val Leu Gly Thr Ser Ala Asp Asn Arg Val Ser Leu Thr
            200                 205                 210

AAC AAC TAC ATT GAC GGT GTC TCC GAC TAC TCC GCC ACC TGC GAT GGC      2208
Asn Asn Tyr Ile Asp Gly Val Ser Asp Tyr Ser Ala Thr Cys Asp Gly
        215                 220                 225

TAC CAC TAC TGG GGC ATC TAC CTC GAT GGT GAC GCC GAC TTG GTC ACC      2256
Tyr His Tyr Trp Gly Ile Tyr Leu Asp Gly Asp Ala Asp Leu Val Thr
    230                 235                 240

ATG AAG GGC AAC TAC ATC TAC CAC ACC TCC GGC CGT AGC CCC AAG GTC      2304
Met Lys Gly Asn Tyr Ile Tyr His Thr Ser Gly Arg Ser Pro Lys Val
245                 250                 255                 260

CAG GAC AAC ACT CTC CTC CAC TGT GTAAGTTGCC TTTTCTCTGC TGGCCGCTTC     2358
Gln Asp Asn Thr Leu Leu His Cys
                265

CGACCTGACT AATCATTGTT GCAG GTC AAC AAC TAC TTC TAC GAC ATC TCC       2409
                           Val Asn Asn Tyr Phe Tyr Asp Ile Ser
                               270                 275

GGC CAC GCT TTT GAG ATC GGT GAG GGT GGC TAC GTC CTG GCT GAG GGC      2457
Gly His Ala Phe Glu Ile Gly Glu Gly Gly Tyr Val Leu Ala Glu Gly
            280                 285                 290

AAC GTT TTC CAG AAC GTC GAC ACC GTC CTT GAG ACC TAC GAG GGC GCG      2505
Asn Val Phe Gln Asn Val Asp Thr Val Leu Glu Thr Tyr Glu Gly Ala
    295                 300                 305

GCC TTC ACC GTC CCC TCC ACC ACC GCC GGT GAA GTC TGC TCC ACC TAC      2553
Ala Phe Thr Val Pro Ser Thr Thr Ala Gly Glu Val Cys Ser Thr Tyr
310                 315                 320                 325

CTT GGC CGT GAC TGT GTC ATC AAC GGC TTC GGC TGC TCC GGC ACT TTC      2601
Leu Gly Arg Asp Cys Val Ile Asn Gly Phe Gly Cys Ser Gly Thr Phe
                330                 335                 340

TCC GAG GAC AGC ACC TCT TTC CTC TCC GAC TTC GAG GGC AAG AAC ATT      2649
Ser Glu Asp Ser Thr Ser Phe Leu Ser Asp Phe Glu Gly Lys Asn Ile
            345                 350                 355

GCC TCT GCT TCC GCT TAC ACC TCT GTT GCC TCT CGC GTT GTT GCT AAC      2697
Ala Ser Ala Ser Ala Tyr Thr Ser Val Ala Ser Arg Val Val Ala Asn
            360                 365                 370

GCC GGT CAG GGC AAC CTG TAAATGAGTT GACTCATTTA TGGTAGATAG             2745
Ala Gly Gln Gly Asn Leu
    375

CAGTGGATGT AATCTAGGGG ATGCGGCGTG CTTGAGAAGT TACCTTTCTT GTATCTACTT    2805

CTATAATAAA TTATGGGGAG TGTTCACGAC CCTAATCTGG TTGAATAACC AGCCGACACA    2865

ATGACATTAT TGTCTACAGA GTTTTCAAGT AGATATGTTC CTTTCACATG TAGTAAGGAG    2925

TATACAGTGT TAACAATTGA TAAGATGGCG ATCGTGAACC AAACTTTCCC ACCCGATGTC    2985

CCAAGATAGG ACTAAAAGTC TAATCTGGAT AGCCGAGCCG GCTATACTTC ACACTCCCAA    3045

AAAGTCTTTT ATTAGTAGAG GCATCATCCT GGAATCGAAT ATTCTTTGCC ATTCAAACTA    3105

AGTTCCAGGA TTTTGACCCT TTCCTCTCTG AAGCCAGCAA AGTAGCAAAG CAACTTATC     3164
```

( 2 ) INFORMATION FOR SEQ ID NO:4:

( i ) SEQUENCE CHARACTERISTICS:

( A ) LENGTH: 379 amino acids ( B ) TYPE: amino acid

-continued ( D ) TOPOLOGY: linear ( i i ) MOLECULE TYPE: protein ( x i ) SEQUENCE DESCRIPTION: SEQ ID NO:4:

Met Lys Tyr Ser Thr Ile Phe Ser Ala Ala Ala Ala Val Phe Ala Gly
1 5 10 15

Ser Ala Ala Ala Val Gly Val Ser Gly Ser Ala Glu Gly Phe Ala Glu
20 25 30

Gly Val Thr Gly Gly Gly Asp Ala Thr Pro Val Tyr Pro Asp Thr Ile
35 40 45

Asp Glu Leu Val Ser Tyr Leu Gly Asp Asp Glu Ala Arg Val Ile Val
50 55 60

Leu Thr Lys Thr Phe Asp Phe Thr Asp Ser Glu Gly Thr Thr Thr Gly
65 70 75 80

Thr Gly Cys Ala Pro Trp Gly Thr Ala Ser Ala Cys Gln Val Ala Ile
85 90 95

Asp Gln Asp Asp Trp Cys Glu Asn Tyr Glu Pro Asp Ala Pro Ser Val
100 105 110

Ser Val Glu Tyr Tyr Asn Ala Gly Val Leu Gly Ile Thr Val Thr Ser
115 120 125

Asn Lys Ser Leu Ile Gly Glu Gly Ser Ser Gly Ala Ile Lys Gly Lys
130 135 140

Gly Leu Arg Ile Val Ser Gly Ala Glu Asn Ile Ile Ile Gln Asn Ile
145 150 155 160

Ala Val Thr Asp Ile Asn Pro Lys Tyr Val Trp Gly Gly Asp Ala Ile
165 170 175

Thr Leu Asp Asp Cys Asp Leu Val Trp Ile Asp His Val Thr Thr Ala
180 185 190

Arg Ile Gly Arg Gln His Tyr Val Leu Gly Thr Ser Ala Asp Asn Arg
195 200 205

Val Ser Leu Thr Asn Asn Tyr Ile Asp Gly Val Ser Asp Tyr Ser Ala
210 215 220

Thr Cys Asp Gly Tyr His Tyr Trp Gly Ile Tyr Leu Asp Gly Asp Ala
225 230 235 240

Asp Leu Val Thr Met Lys Gly Asn Tyr Ile Tyr His Thr Ser Gly Arg
245 250 255

Ser Pro Lys Val Gln Asp Asn Thr Leu Leu His Cys Val Asn Asn Tyr
260 265 270

Phe Tyr Asp Ile Ser Gly His Ala Phe Glu Ile Gly Glu Gly Gly Tyr
275 280 285

Val Leu Ala Glu Gly Asn Val Phe Gln Asn Val Asp Thr Val Leu Glu
290 295 300

Thr Tyr Glu Gly Ala Ala Phe Thr Val Pro Ser Thr Thr Ala Gly Glu
305 310 315 320

Val Cys Ser Thr Tyr Leu Gly Arg Asp Cys Val Ile Asn Gly Phe Gly
325 330 335

Cys Ser Gly Thr Phe Ser Glu Asp Ser Thr Ser Phe Leu Ser Asp Phe
340 345 350

Glu Gly Lys Asn Ile Ala Ser Ala Ser Ala Tyr Thr Ser Val Ala Ser
355 360 365

Arg Val Val Ala Asn Ala Gly Gln Gly Asn Leu
370 375

( 2 ) INFORMATION FOR SEQ ID NO:5:

( i ) SEQUENCE CHARACTERISTICS:

-continued ( A ) LENGTH: 2774 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Aspergillus niger N400

( v i i ) IMMEDIATE SOURCE:
( B ) CLONE: Plasmid pGW830 (DSM 4389)

( i x ) FEATURE:
( A ) NAME/KEY: CDS
( B ) LOCATION: join(1134..1337, 1400..1543, 1600..1725, 1783..2112, 2170..2502)
( D ) OTHER INFORMATION: /transl_except=(pos: 1541 .. 1543, aa: Tyr)

( i x ) FEATURE:
( A ) NAME/KEY: sig_peptide
( B ) LOCATION: 1134..1193

( i x ) FEATURE:
( A ) NAME/KEY: exon
( B ) LOCATION: 1194..1337

( i x ) FEATURE:
( A ) NAME/KEY: intron
( B ) LOCATION: 1338..1399

( i x ) FEATURE:
( A ) NAME/KEY: exon
( B ) LOCATION: 1400..1542

( i x ) FEATURE:
( A ) NAME/KEY: intron
( B ) LOCATION: 1543..1598

( i x ) FEATURE:
( A ) NAME/KEY: exon
( B ) LOCATION: 1599..1725

( i x ) FEATURE:
( A ) NAME/KEY: intron
( B ) LOCATION: 1726..1782

( i x ) FEATURE:
( A ) NAME/KEY: exon
( B ) LOCATION: 1783..2112

( i x ) FEATURE:
( A ) NAME/KEY: intron
( B ) LOCATION: 2113..2169

( i x ) FEATURE:
( A ) NAME/KEY: exon
( B ) LOCATION: 2170..2502

( i x ) FEATURE:
( A ) NAME/KEY: promoter
( B ) LOCATION: 1..1133

( i x ) FEATURE:
( A ) NAME/KEY: terminator
( B ) LOCATION: 2506..2774

( x i ) SEQUENCE DESCRIPTION: SEQ ID NO:5:

CTCGAGTCCA GTAGTTAGTA GTTGCGGATA ACAAGGATAG ATCATCCCCT TTGGTTATGT 60

GTGAGTCTGA CCAAGGAAGC ATTGGGGGAG AGACTATTGG GTCAATGGCA CTCACGGGAA 120

AAAGAGGCGA AAGGGATGGG AGAGGTGATG CCTGAGGCCG CATGAATATA TCATGTGAGA 180

GCAAAGAAGA TCAAACAAAC AATACAAACC CCAGCGTGAC CCCTCACTGC CACGTGATTT 240

-continued

```
CCCAGCTAAT CCTCTTCGGG GTGTTTTCCC CCCCAATCGG GGCTTCTTGG CAACCACTAA    300

TTTCCATAAT TTCCACTGGA CTCTTGAACG GTTCTTGCAA TGTCTCACTG TCAGACTGAG    360

AGTACCACTT TTCTCCCTCT ACCAAGCCTT GAAATAGGTC AGGGCCGTTC ATGGGACCCT    420

GACCTCCACC CCTTCGGAAG CCAGCCGGAT TGCTTCTAAG ACATCCTGAA GTGGGCCACC    480

ATCCGGCTCT CACCATTCCT ATGCTCTGCC AAGCGACTCG ACCTCGTTCT TCACCGGAGT    540

GCCCGGGTCC GCCCTGAACT CAAGGTCTGC ATGGGAAGAG ATTTCCGGCT GTTTCCCCCA    600

ACGGCGTCTA GGCAGATAGG CTAGGCGTTG TGTTCCTGGC TTGATCAGCA AGGTTTATCA    660

TAGTCCTCAT GACTCGTAAA ACCCAAGAAG ATAAAATGAA GATGTTGGGT CCGCGAGTCC    720

GGTGATGTCT GGGCAGCAGT AGTAACACTC TAAAATATAA GCCACCACAC CCACTGACAG    780

GTTAATCTCC GGTAGAAGAA CCAAGACCTA CCTGCCAAGC CACGTTGATT GGGTTCTCAT    840

CCATTTCAGG TCCTGTCCCC GGTCCCCTGG TGTCATTCCA GAACATGGTC AAGGAAATCA    900

AACGGCCACT GTCTGACTGC CAGCTCCACC ATCATGTAAT CCGGCTTCTC TATATAAACT    960

TGGGAATGTT CCCCTCTCCT GTGCCACCCA GAAGAAGACA TCACCTTCCT TGCTTCTACA   1020

AGCCTGTCAC TCTTTCCAGG CCGTCGTTCT TTGATATTTC TCACTAGACT TTCATTCTCT   1080

TGAATATTTT CTTTTTGTTT TCCCTCGTAT TTTCTGTGCT TTGAGAGCCC AAC ATG      1136
                                                           Met
                                                             1

CAT TAC AAA CTG CTT TTT GCT GCT GCC GCA GCA TCC TTG GCC AGC GCT     1184
His Tyr Lys Leu Leu Phe Ala Ala Ala Ala Ala Ser Leu Ala Ser Ala
             5                  10                  15

GTC AGT GCC GCC GGT GTT GTT GGT GCC GCC GAG GGT TTC GCC CAT GGT     1232
Val Ser Ala Ala Gly Val Val Gly Ala Ala Glu Gly Phe Ala His Gly
         20                  25                  30

GTC ACT GGC GGT GGC AGC GCT TCC CCC GTC TAT CCT ACG ACT ACT GAT     1280
Val Thr Gly Gly Gly Ser Ala Ser Pro Val Tyr Pro Thr Thr Thr Asp
     35                  40                  45

GAG CTG GTC TCT TAC CTC GGA GAT AAC GAG CCC CGG GTG ATT ATC CTG     1328
Glu Leu Val Ser Tyr Leu Gly Asp Asn Glu Pro Arg Val Ile Ile Leu
 50                  55                  60                  65

GAT AGA ACG TAGGTCGATC CTCAATTGGA AATGGATGGG TAGACGTGGG             1377
Asp Arg Thr

CCTAACAGGT TGATAATCCA GC TTC GAC TTC ACC GGC ACT GAG GGT ACT GAA    1429
                         Phe Asp Phe Thr Gly Thr Glu Gly Thr Glu
                                  70                  75

ACT ACC ACC GGA TGT GCC CCC TGG GGA ACT GCT TCC CAA TGC CAG GTG     1477
Thr Thr Thr Gly Cys Ala Pro Trp Gly Thr Ala Ser Gln Cys Gln Val
     80                  85                  90

GCC ATC AAC CTG CAC AGC TGG TGT GAC AAC TAC CAG GCT AGC GCC CCC     1525
Ala Ile Asn Leu His Ser Trp Cys Asp Asn Tyr Gln Ala Ser Ala Pro
 95                 100                 105                 110

AAG GTA TCC GTG ACT TAG TATGTTGTCC CCGTTCGATT GGTGACCCTG            1573
Lys Val Ser Val Thr Tyr
                115

TCTTTCCATG CTGATAGCCG TATAGT GAT AAG GCG GGT ATC CTC CCC ATT ACG    1626
                             Asp Lys Ala Gly Ile Leu Pro Ile Thr
                                         120                 125

GTC AAC TCC AAC AAA AGT ATC GTT GGT CAG GGC ACC AAG GGA GTC ATC     1674
Val Asn Ser Asn Lys Ser Ile Val Gly Gln Gly Thr Lys Gly Val Ile
                130                 135                 140

AAG GGC AAG GGT CTC CGT GTG GTC AGC GGT GCC AAG AAC GTC ATC ATC     1722
Lys Gly Lys Gly Leu Arg Val Val Ser Gly Ala Lys Asn Val Ile Ile
            145                 150                 155

CAG TGAGTGCAGA ACATCGGTCT TAGGATGTGA AAAAACCCTT TGCTAATAAA GGCCAGG  1782
Gln
```

-continued

```
AAC ATT GCC GTT ACC GAC ATC AAC CCC AAG TAT GTC TGG GGT GGT GAT       1830
Asn Ile Ala Val Thr Asp Ile Asn Pro Lys Tyr Val Trp Gly Gly Asp
    160                 165                 170

GCC ATT ACT GTC GAT GAC TCT GAT CTG GTC TGG ATC GAC CAT GTG ACC       1878
Ala Ile Thr Val Asp Asp Ser Asp Leu Val Trp Ile Asp His Val Thr
175                 180                 185                 190

ACT GCT CGC ATT GGT CGC CAG CAC ATC GTT CTG GGA ACC AGC GCC GAC       1926
Thr Ala Arg Ile Gly Arg Gln His Ile Val Leu Gly Thr Ser Ala Asp
                195                 200                 205

AAC CGC GTC ACC ATC TCC TAC TCC CTC ATC GAT GGT CGC TCC GAC TAC       1974
Asn Arg Val Thr Ile Ser Tyr Ser Leu Ile Asp Gly Arg Ser Asp Tyr
            210                 215                 220

TCT GCC ACC TGC AAC GGC CAC CAC TAC TGG GGC GTG TAC CTG GAC GGC       2022
Ser Ala Thr Cys Asn Gly His His Tyr Trp Gly Val Tyr Leu Asp Gly
        225                 230                 235

AGC AAC GAC ATG GTC ACC CTT AAG GGC AAC TAC TTC TAC AAC CTG AGC       2070
Ser Asn Asp Met Val Thr Leu Lys Gly Asn Tyr Phe Tyr Asn Leu Ser
    240                 245                 250

GGC CGC ATG CCC AAG GTT CAG GGT AAC ACT CTG CTG CAC GCC               2112
Gly Arg Met Pro Lys Val Gln Gly Asn Thr Leu Leu His Ala
255                 260                 265

GTATGTCGCC TTGAGCCTCC TATATGATTT GCACATTACT GACAAGTCTG ACTACAG        2169

GTG AAC AAC CTC TTC CAC AAC TTT GAC GGC CAC GCC TTC GAA ATC GGC       2217
Val Asn Asn Leu Phe His Asn Phe Asp Gly His Ala Phe Glu Ile Gly
    270                 275                 280

ACT GGT GGC TAC GTC CTG GCC GAG GGT AAC GTC TTC CAG GAC GTT AAC       2265
Thr Gly Gly Tyr Val Leu Ala Glu Gly Asn Val Phe Gln Asp Val Asn
285                 290                 295                 300

ATT GTG GTG GAG ACG CCC ATC AGC GGC CAG CTC TTC AGC TCC CCC GAC       2313
Ile Val Val Glu Thr Pro Ile Ser Gly Gln Leu Phe Ser Ser Pro Asp
                305                 310                 315

GCC AAC ACC AAC CAG CAG TGC GCC TCC GTC TTC GGT CGT TCC TGC CAG       2361
Ala Asn Thr Asn Gln Gln Cys Ala Ser Val Phe Gly Arg Ser Cys Gln
            320                 325                 330

CTC AAC GCC TTC GGC AAC TCC GGC TCG ATG TCC GGA TCG GAC ACC AGC       2409
Leu Asn Ala Phe Gly Asn Ser Gly Ser Met Ser Gly Ser Asp Thr Ser
        335                 340                 345

ATC ATC AGC AAG TTC GCT GGC AAG ACC ATT GCT GCG GCT CAC CCC CCG       2457
Ile Ile Ser Lys Phe Ala Gly Lys Thr Ile Ala Ala Ala His Pro Pro
    350                 355                 360

GGT AAC ATT GCC CAG TGG ACC ATG AAG AAC GCT GGC CAG GGC AAA           2502
Gly Asn Ile Ala Gln Trp Thr Met Lys Asn Ala Gly Gln Gly Lys
365                 370                 375

TAAGGTTTTA CAGCAGAACA ATTCTGTGAA GGAGGCTGGC CAAAGCCCAG ATGAGGATAG     2562

AGGGTACCTG CTTCGACATC TATAGTTCAA TAGTCCAGGA TTATAGACGA ATGATTATTG     2622

CTCCAGAATG GTGAAGTATT TCTAGCAGAC CATGACGCGT ACGCAACATA GACCGCTCCA     2682

TGTTACTGAC TGCGACTGTA TTTGGAGGAT TGAGGAAAGG TAGATAAAAG TATATACTAC     2742

AAAACCGCCA TAACAGCAAC CGACGCCTCG AG                                   2774
```

( 2 ) INFORMATION FOR SEQ ID NO:6:

( i ) SEQUENCE CHARACTERISTICS:
( A ) LENGTH: 379 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met His Tyr Lys Leu Leu Phe Ala Ala Ala Ala Ala Ser Leu Ala Ser
  1               5                  10                  15
```

-continued

```
Ala Val Ser Ala Ala Gly Val Val Gly Ala Ala Glu Gly Phe Ala His
            20                  25                  30

Gly Val Thr Gly Gly Gly Ser Ala Ser Pro Val Tyr Pro Thr Thr Thr
        35                  40                  45

Asp Glu Leu Val Ser Tyr Leu Gly Asp Asn Glu Pro Arg Val Ile Ile
    50                  55                  60

Leu Asp Arg Thr Phe Asp Phe Thr Gly Thr Glu Gly Thr Glu Thr Thr
65                  70                  75                  80

Thr Gly Cys Ala Pro Trp Gly Thr Ala Ser Gln Cys Gln Val Ala Ile
                85                  90                  95

Asn Leu His Ser Trp Cys Asp Asn Tyr Gln Ala Ser Ala Pro Lys Val
            100                 105                 110

Ser Val Thr Tyr Asp Lys Ala Gly Ile Leu Pro Ile Thr Val Asn Ser
        115                 120                 125

Asn Lys Ser Ile Val Gly Gln Gly Thr Lys Gly Val Ile Lys Gly Lys
    130                 135                 140

Gly Leu Arg Val Val Ser Gly Ala Lys Asn Val Ile Ile Gln Asn Ile
145                 150                 155                 160

Ala Val Thr Asp Ile Asn Pro Lys Tyr Val Trp Gly Gly Asp Ala Ile
                165                 170                 175

Thr Val Asp Asp Ser Asp Leu Val Trp Ile Asp His Val Thr Thr Ala
            180                 185                 190

Arg Ile Gly Arg Gln His Ile Val Leu Gly Thr Ser Ala Asp Asn Arg
        195                 200                 205

Val Thr Ile Ser Tyr Ser Leu Ile Asp Gly Arg Ser Asp Tyr Ser Ala
    210                 215                 220

Thr Cys Asn Gly His His Tyr Trp Gly Val Tyr Leu Asp Gly Ser Asn
225                 230                 235                 240

Asp Met Val Thr Leu Lys Gly Asn Tyr Phe Tyr Asn Leu Ser Gly Arg
                245                 250                 255

Met Pro Lys Val Gln Gly Asn Thr Leu Leu His Ala Val Asn Asn Leu
            260                 265                 270

Phe His Asn Phe Asp Gly His Ala Phe Glu Ile Gly Thr Gly Gly Tyr
        275                 280                 285

Val Leu Ala Glu Gly Asn Val Phe Gln Asp Val Asn Ile Val Val Glu
    290                 295                 300

Thr Pro Ile Ser Gly Gln Leu Phe Ser Ser Pro Asp Ala Asn Thr Asn
305                 310                 315                 320

Gln Gln Cys Ala Ser Val Phe Gly Arg Ser Cys Gln Leu Asn Ala Phe
                325                 330                 335

Gly Asn Ser Gly Ser Met Ser Gly Ser Asp Thr Ser Ile Ile Ser Lys
            340                 345                 350

Phe Ala Gly Lys Thr Ile Ala Ala Ala His Pro Pro Gly Asn Ile Ala
        355                 360                 365

Gln Trp Thr Met Lys Asn Ala Gly Gln Gly Lys
    370                 375
```

( 2 ) INFORMATION FOR SEQ ID NO:7:

( i ) SEQUENCE CHARACTERISTICS:

( A ) LENGTH: 3168 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Aspergillus niger N400

( v i i ) IMMEDIATE SOURCE:
( B ) CLONE: Plasmid pGW850 (DSM 4390)

( i x ) FEATURE:
( A ) NAME/KEY: CDS
( B ) LOCATION: join(1368..1853, 1932..1997, 2063..2233, 2297..2708)
( D ) OTHER INFORMATION: /transl_except=(pos: 2231 .. 2233, aa: Asn)

( i x ) FEATURE:
( A ) NAME/KEY: sig_peptide
( B ) LOCATION: 1368..1421

( i x ) FEATURE:
( A ) NAME/KEY: exon
( B ) LOCATION: 1422..1853

( i x ) FEATURE:
( A ) NAME/KEY: intron
( B ) LOCATION: 1854..1931

( i x ) FEATURE:
( A ) NAME/KEY: exon
( B ) LOCATION: 1932..1997

( i x ) FEATURE:
( A ) NAME/KEY: intron
( B ) LOCATION: 1998..2062

( i x ) FEATURE:
( A ) NAME/KEY: exon
( B ) LOCATION: 2063..2231

( i x ) FEATURE:
( A ) NAME/KEY: intron
( B ) LOCATION: 2232..2294

( i x ) FEATURE:
( A ) NAME/KEY: exon
( B ) LOCATION: 2295..2707

( i x ) FEATURE:
( A ) NAME/KEY: promoter
( B ) LOCATION: 1..1367

( i x ) FEATURE:
( A ) NAME/KEY: terminator
( B ) LOCATION: 2711..3168

( x i ) SEQUENCE DESCRIPTION: SEQ ID NO:7:

```
GAATTCGAAT CTGGAGGACA TTACGTGTGC CTGACTTCGG GGTACTTCTG TCTTCACTGT   60
AGCCAGGCAC TATCCCTGAC ACTCTGCCCC CTACGTGGTC TTACCTTTAT CGGATTTAGA  120
TAGTAACCAA TCTGATCCCA CATCCTGATA CCTGGATACT TTTCCCCATG GCATCGTGTA  180
ATCTATGATA CTCAAAGGAA CAAAGCAGAT ACTTGAAGCT GCATAGACCT TGTCTCAGAG  240
ATCGCAGCTT TGTTGTTTAG AAACACAGTC TGTCACCGGT TCGCCAGATT AAGTGTTAAA  300
CATGTGACAG GCACCTAAAA GCTGACAGCC TCGGCCTGAG CTCGTAGAGT ACCCTCTTCT  360
AGGTCTTTGT GGGTTGACTG CAAGCAAAGG ATCAAGCTTG TCGGAGAATT TGGAGCTTTT  420
GCATGTAATT TTTCCGACTG GGGTCCGAGT ATTTCCCGCG GTGTATGTTA GAATGGTTAG  480
TATGGATAGA TTGGTAGAAA AGTTGACCTG AAACATTGAG ATATCTGATT AGTAGTATGC  540
TATAGATCTG GATATACATT TCTGCAATGA AATGTGATCA TATGAACTTT TTGAAATGAA  600
GGAGATATAT GCATAGTTGT GAAATATGCG CGTGGCCTGT CCGTTCTCAG CCCTGACGGG  660
TGACATCCCG TTCGGCTGTT TAGTGGAAAG CCGCGTGGCT GTCTCGGGGG AGTGGGTCAG  720
```

-continued

```
GGTCCTCCAG GAATTTTCTT TTCTAGGTTA GTTCTTCCAG CCTTCCAGGG TCCTGCAGAC    780

CCGCCTCCAA ACAGCTGATT GTGGTGTAAC CGTTTACAAG ACTGGCCAGC ATATTTTTGT    840

ATATGTCACT ATCGTGAAGA TTATATTCAT CTTATATCAA TTGGAGCTTG AGGTCTATCT    900

CTTAGTGTGC GCACAAAAAG CCGATATGAT TCAATGCGTC TGTCAAATAA CCCGAACTGT    960

CCGAATCATC ACACCCACAG AGTGCTGCGA AGGTCGTGAT CCTTCCAAGT ATCTCAGAAA   1020

AGACCACTAC ACTGGACCCC CAACAAAGGT ACACAATAAC TTCGGGTAGA GAATTGTGCG   1080

ATGCAGAGCA TAGTATATCT GAAACAACTG TCACTGCAGA CCTTTCCTAC TTGTGCATCC   1140

GGTTCGCATT GCAGTGGGGC AGGGCAGTTC TTGGCCGAAG AACTATGATC ACTTTGTAAC   1200

AACGGTGGCC CCTGTAGCTA CCAGTGTTCT GTACTTCGGC AAAATTCAAT CCTTGGCTTC   1260

TATATGTCAC TAGGTGACTT TGAATACATA AAGATGAAAT GTTGGAACTT TGGACGATAC   1320

CTCTGTCTGT CAACACAATC TGTACTTTTC CAAAACCCTT ATCCATT ATG AAG GTC   1376
                                                    Met Lys Val
                                                     1

CCC TTC CTC CAA CTT CTC TGC CTA AAT GCC GCC TTG GCT AGT GCC AAT   1424
Pro Phe Leu Gln Leu Leu Cys Leu Asn Ala Ala Leu Ala Ser Ala Asn
     5                   10                  15

GTT GTT CAA GGT GCT GCC CAG GGT TTC GCA GCC GGC GTC ACT GGC GGC   1472
Val Val Gln Gly Ala Ala Gln Gly Phe Ala Ala Gly Val Thr Gly Gly
 20                  25                  30                  35

GGC GAT ATA ACT CCC AGC TAC CCC AAA ACC AAC GAG GAG CTT GTC TCC   1520
Gly Asp Ile Thr Pro Ser Tyr Pro Lys Thr Asn Glu Glu Leu Val Ser
                 40                  45                  50

CTG CTC GAG AGT GAC GAA CCC CAA GTC GTC GTA CTC ACC AAG ACC TTT   1568
Leu Leu Glu Ser Asp Glu Pro Gln Val Val Val Leu Thr Lys Thr Phe
             55                  60                  65

GAT TTC ATC GGT ACC GAG GGA ACC ACG ACC GAG GAT GGA TGC GCG CCC   1616
Asp Phe Ile Gly Thr Glu Gly Thr Thr Thr Glu Asp Gly Cys Ala Pro
         70                  75                  80

TGG GGT ACT GGG AAG TCC TGC CAG CTG GCC ATC AAC TCC AAT GGA TGG   1664
Trp Gly Thr Gly Lys Ser Cys Gln Leu Ala Ile Asn Ser Asn Gly Trp
     85                  90                  95

TGT GGT AAA AAT CCC GTC GTA ACC ATC ACG TAT GAT AAC GCC GCC AAG   1712
Cys Gly Lys Asn Pro Val Val Thr Ile Thr Tyr Asp Asn Ala Ala Lys
100                 105                 110                 115

AAT GGC ATT CAT ATC AAG TCC AAC AAG ACT CTT GTT GGT GAG GGA GAC   1760
Asn Gly Ile His Ile Lys Ser Asn Lys Thr Leu Val Gly Glu Gly Asp
                120                 125                 130

AAG GGC GTG CTC AGC GGA AAG GGT CTC TAC TTT GAG GGT GGT GTT TCC   1808
Lys Gly Val Leu Ser Gly Lys Gly Leu Tyr Phe Glu Gly Gly Val Ser
            135                 140                 145

AAT ATC ATC GTG CAG AAC ATT AAG ATT ACG AAC CTC AAC CCT GGG       1853
Asn Ile Ile Val Gln Asn Ile Lys Ile Thr Asn Leu Asn Pro Gly
        150                 155                 160

TATGTATCAT CCCAGTAACT AGGAGTTCTC GAATGCTTTG GGAGACACAC CATGTGTTCT   1913

AACGTCTTTC ACTACAGT TTT GTC TGG GGT GGC GAC GCG TTT ACT TTC TTT   1964
                    Phe Val Trp Gly Gly Asp Ala Phe Thr Phe Phe
                            165                 170

GGC GCT GAC CTG ATC TGG ATC GAC CAC TGC GAG GTAAGACAGA AATCTCCATC   2017
Gly Ala Asp Leu Ile Trp Ile Asp His Cys Glu
    175                 180

ATCTGATAAT CATGATTGAG TTTCTCACGT TGACTTATGG ATTAG ACC TCC CTC     2071
                                                  Thr Ser Leu
                                                  185

ACC GGA CGC CAA CAC TAC GTG ACC GGC TTC CAC CCC AAC ACC CGC ATG   2119
Thr Gly Arg Gln His Tyr Val Thr Gly Phe His Pro Asn Thr Arg Met
        190                 195                 200
```

-continued

```
ACT TGG TCC AAT AAC TTC CTT AAC GGC GTA ACC ACC CAC TCC GCA GGC      2167
Thr Trp Ser Asn Asn Phe Leu Asn Gly Val Thr Thr His Ser Ala Gly
    205                     210                 215

TGT GAT GAC CAC CAC TAC TGG ACA ATG GAG CTA GTT GGC CCT GGG GAC      2215
Cys Asp Asp His His Tyr Trp Thr Met Glu Leu Val Gly Pro Gly Asp
220                     225                 230                 235

GAG ATT ACC TTC CAG AGT ACGTGTCCCA TGAAAACCTA AAAGAAGCAT             2263
Glu Ile Thr Phe Gln Asn
                240

CTATTCAACT AACATACGTG TTCACTCACA GAC AAC TAC GTC TAC CAC ACC ACC     2317
                                     Asn Tyr Val Tyr His Thr Thr
                                                 245

GGC CGT GGA CCC GCT CTC TCC GGC ACG ACC CTC TTC CAC GCA GTC AAC      2365
Gly Arg Gly Pro Ala Leu Ser Gly Thr Thr Leu Phe His Ala Val Asn
    250                     255                 260

AGC GTC TGG TCT TCC ATC CCC GGA CAC GCC ATC GAG GGC GGT GAC AAG      2413
Ser Val Trp Ser Ser Ile Pro Gly His Ala Ile Glu Gly Gly Asp Lys
265                     270                 275                 280

GGC CGC GGT CTT TTC GAG GGA TGC TTC TTC GAA GAT GTT GTC GAG ATC      2461
Gly Arg Gly Leu Phe Glu Gly Cys Phe Phe Glu Asp Val Val Glu Ile
                285                 290                 295

GCC CCC GCC AAG CCC GAG AAC CAA CTC TTC AGC GCC AGT GAA GCC AAC      2509
Ala Pro Ala Lys Pro Glu Asn Gln Leu Phe Ser Ala Ser Glu Ala Asn
            300                 305                 310

GCC GCA TCT TGC AAG TCC GCC TTG GGA CGC GCT TGC CAG GCC AAT GGC      2557
Ala Ala Ser Cys Lys Ser Ala Leu Gly Arg Ala Cys Gln Ala Asn Gly
        315                 320                 325

TAT AGC AAA TCT GGT GCT TTT GGC AGT TCT GAA ACT GGC TTT TTC AAG      2605
Tyr Ser Lys Ser Gly Ala Phe Gly Ser Ser Glu Thr Gly Phe Phe Lys
    330                     335                 340

GAC TTT GCC GGA CTG ACT ATT GCA CCG GCC GGC TCT GCG ACC GAC GCT      2653
Asp Phe Ala Gly Leu Thr Ile Ala Pro Ala Gly Ser Ala Thr Asp Ala
345                     350                 355                 360

CTC GCT TAT GTT CCT AAG AAT TGT GGT ATT GGG CGT CTT GAA AGC TGC      2701
Leu Ala Tyr Val Pro Lys Asn Cys Gly Ile Gly Arg Leu Glu Ser Cys
                365                 370                 375

GAT GCTTAGGGTG GAGCTTGTTG AGTCTATATT TGACCAATAG GGTGTACTTT           2754
Asp Ala

ATTCTACTTC AGTCCGGTTA ATATATGTAA TATATTTGGA TTCTGCGCGC AACTTGTGCT    2814

TTCCTCAGTT CTGCAATATC CATTCAAGTA GTCTACGCAT CTCTATAGAC TATTGATCAA    2874

TATAACATAG CAGACAACAC TGCCAACCAA AATATAAGAC CCAGTATATA CTTTCCGTGA    2934

AGTATTTAAA ACAGATTACA TCTAGCTTGA AAATCATCCC TCTCTGGTTC AAGTATTCAC    2994

GTCAGTAGCT GAAAAGGGAA TAACGATGAC CGCGAATAAT TTGACAATCA TCTACCCGAT    3054

GAATACCAAT CAAGGAAAAC AAAAGTCGTG AGAAAAATGC AAGGGAGAAA GTTATATGTT    3114

ACAAAAGAAA CATACAACAG AAGGAATATG TCAGTGGTCA TTGAACATTA CAAA          3168
```

( 2 ) INFORMATION FOR SEQ ID NO:8:

( i ) SEQUENCE CHARACTERISTICS:
( A ) LENGTH: 378 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Lys Val Pro Phe Leu Gln Leu Leu Cys Leu Asn Ala Ala Leu Ala
1               5                   10                  15

Ser Ala Asn Val Val Gln Gly Ala Ala Gln Gly Phe Ala Ala Gly Val
            20                  25                  30
```

-continued

```
Thr Gly Gly Gly Asp Ile Thr Pro Ser Tyr Pro Lys Thr Asn Glu Glu
        35                  40                  45

Leu Val Ser Leu Leu Glu Ser Asp Glu Pro Gln Val Val Val Leu Thr
    50                  55                  60

Lys Thr Phe Asp Phe Ile Gly Thr Glu Gly Thr Thr Thr Glu Asp Gly
65                  70                  75                  80

Cys Ala Pro Trp Gly Thr Gly Lys Ser Cys Gln Leu Ala Ile Asn Ser
                85                  90                  95

Asn Gly Trp Cys Gly Lys Asn Pro Val Val Thr Ile Thr Tyr Asp Asn
            100                 105                 110

Ala Ala Lys Asn Gly Ile His Ile Lys Ser Asn Lys Thr Leu Val Gly
        115                 120                 125

Glu Gly Asp Lys Gly Val Leu Ser Gly Lys Gly Leu Tyr Phe Glu Gly
    130                 135                 140

Gly Val Ser Asn Ile Ile Val Gln Asn Ile Lys Ile Thr Asn Leu Asn
145                 150                 155                 160

Pro Gly Phe Val Trp Gly Gly Asp Ala Phe Thr Phe Phe Gly Ala Asp
                165                 170                 175

Leu Ile Trp Ile Asp His Cys Glu Thr Ser Leu Thr Gly Arg Gln His
            180                 185                 190

Tyr Val Thr Gly Phe His Pro Asn Thr Arg Met Thr Trp Ser Asn Asn
        195                 200                 205

Phe Leu Asn Gly Val Thr Thr His Ser Ala Gly Cys Asp Asp His His
    210                 215                 220

Tyr Trp Thr Met Glu Leu Val Gly Pro Gly Asp Glu Ile Thr Phe Gln
225                 230                 235                 240

Asn Asn Tyr Val Tyr His Thr Thr Gly Arg Gly Pro Ala Leu Ser Gly
                245                 250                 255

Thr Thr Leu Phe His Ala Val Asn Ser Val Trp Ser Ser Ile Pro Gly
            260                 265                 270

His Ala Ile Glu Gly Gly Asp Lys Gly Arg Gly Leu Phe Glu Gly Cys
        275                 280                 285

Phe Phe Glu Asp Val Val Glu Ile Ala Pro Ala Lys Pro Glu Asn Gln
    290                 295                 300

Leu Phe Ser Ala Ser Glu Ala Asn Ala Ala Ser Cys Lys Ser Ala Leu
305                 310                 315                 320

Gly Arg Ala Cys Gln Ala Asn Gly Tyr Ser Lys Ser Gly Ala Phe Gly
                325                 330                 335

Ser Ser Glu Thr Gly Phe Phe Lys Asp Phe Ala Gly Leu Thr Ile Ala
            340                 345                 350

Pro Ala Gly Ser Ala Thr Asp Ala Leu Ala Tyr Val Pro Lys Asn Cys
        355                 360                 365

Gly Ile Gly Arg Leu Glu Ser Cys Asp Ala
    370                 375
```

( 2 ) INFORMATION FOR SEQ ID NO:9:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO

-continued ( x i ) SEQUENCE DESCRIPTION: SEQ ID NO:9:

TGNGGNCTYC CRAARCG 17

( 2 ) INFORMATION FOR SEQ ID NO:10:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:10:

TGNGGNCTYC CYAARCG 17

( 2 ) INFORMATION FOR SEQ ID NO:11:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

AA W ATHATHA THCARA 16

( 2 ) INFORMATION FOR SEQ ID NO:12:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:12:

AGCGTCGACG CT 12

( 2 ) INFORMATION FOR SEQ ID NO:13:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
( A ) NAME/KEY: CDS
( B ) LOCATION: 1..33
( D ) OTHER INFORMATION: /note="from 1 to 27 PLI signal sequence; from 28 to 33 N-terminal amino acids of Desulfatohirudin"

( x i ) SEQUENCE DESCRIPTION: SEQ ID NO:13:

```
GCC GCC CTC GCT GCG CGC GCC GCT GCT GTT GTT    33
Ala Ala Leu Ala Ala Arg Ala Ala Ala Val Val
 1               5                  10
```

( 2 ) INFORMATION FOR SEQ ID NO:14:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:14:

```
Ala Ala Leu Ala Ala Arg Ala Ala Ala Val Val
 1               5                  10
```

( 2 ) INFORMATION FOR SEQ ID NO:15:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:15:

```
CGGCGGGAGC GACGCGCGCG GCGACGACAA CAA    33
```

( 2 ) INFORMATION FOR SEQ ID NO:16:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: DNA (synthetic)

( i i i ) HYPOTHETICAL: NO ( i v ) ANTI-SENSE: NO ( i x ) FEATURE:
( A ) NAME/KEY: PstI/DdeI-linker
( B ) LOCATION: complement (5..15)
( D ) OTHER INFORMATION: /note="Locations 1-4 and 16-18 are single stranded "sticky ends""

( x i ) SEQUENCE DESCRIPTION: SEQ ID NO:16:

```
ACGTACACTA GACGGAGT    18
```

( 2 ) INFORMATION FOR SEQ ID NO:17:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: misc_feature
( B ) LOCATION: 1..42

-continued ( D ) OTHER INFORMATION: /note="non-coding strand of part of the pelA- IFN fusion from Figure 20"

( x i ) SEQUENCE DESCRIPTION: SEQ ID NO:17:

```
GTGAGTCTGA GGCAGATCAC ACATGTGGAA GTGTGTAGAA CC                    42
```

( 2 ) INFORMATION FOR SEQ ID NO:18:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="mutagenic oligonucleotide used as primer in primer extension DNA synthesis as shown in Figure 20"

( i i i ) HYPOTHETICAL: NO ( i x ) FEATURE:
( A ) NAME/KEY: sig_peptide
( B ) LOCATION: 19..42
( D ) OTHER INFORMATION: /note="amino acid sequence used for deletion mutagenesis of the pelA signal sequence"

( i x ) FEATURE:
( A ) NAME/KEY: CDS
( B ) LOCATION: 19..42

( x i ) SEQUENCE DESCRIPTION: SEQ ID NO:18:

```
GGTTCTACAC ACTTCACC ATG TGT GAT CTG CCT CAG ACT CAC               42
                    Met Cys Asp Leu Pro Gln Thr His
                     1               5
```

( 2 ) INFORMATION FOR SEQ ID NO:19:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:19:

```
Met Cys Asp Leu Pro Gln Thr His
 1               5
```